(12) United States Patent
Zielinski et al.

(10) Patent No.: US 9,421,180 B2
(45) Date of Patent: Aug. 23, 2016

(54) ANTIOXIDANT COMPOSITIONS FOR TREATMENT OF INFLAMMATION OR OXIDATIVE DAMAGE

(71) Applicant: Perio Sciences, LLC, Dallas, TX (US)

(72) Inventors: Jan Zielinski, Vista, CA (US); Thomas Russell Moon, Dallas, TX (US); Edward P. Allen, Dallas, TX (US)

(73) Assignee: Perio Sciences, LLC, Dallas, TX (US)

( * ) Notice: Subject to any disclaimer, the term of this patent is extended or adjusted under 35 U.S.C. 154(b) by 19 days.

(21) Appl. No.: 14/347,724

(22) PCT Filed: Sep. 28, 2012

(86) PCT No.: PCT/US2012/057824
§ 371 (c)(1),
(2) Date: Mar. 27, 2014

(87) PCT Pub. No.: WO2013/049507
PCT Pub. Date: Apr. 4, 2013

(65) Prior Publication Data
US 2014/0378547 A1   Dec. 25, 2014

Related U.S. Application Data

(60) Provisional application No. 61/541,500, filed on Sep. 30, 2011, provisional application No. 61/562,262, filed on Nov. 21, 2011, provisional application No. 61/646,648, filed on May 14, 2012, provisional application No. 61/679,884, filed on Aug. 6, 2012.

(51) Int. Cl.
| | |
|---|---|
| *A61K 31/192* | (2006.01) |
| *A61K 31/05* | (2006.01) |
| *A61K 31/12* | (2006.01) |
| *A61K 31/357* | (2006.01) |
| *A61K 9/00* | (2006.01) |
| *A61K 9/06* | (2006.01) |
| *A61K 9/70* | (2006.01) |

(52) U.S. Cl.
CPC .......... *A61K 31/192* (2013.01); *A61K 9/006* (2013.01); *A61K 9/06* (2013.01); *A61K 9/7007* (2013.01); *A61K 31/05* (2013.01); *A61K 31/12* (2013.01); *A61K 31/357* (2013.01)

(58) Field of Classification Search
CPC .. A61K 2300/00; A61K 31/05; A61K 31/12; A61K 31/192; A61K 31/357; A61K 9/006; A61K 9/06; A61K 9/7007
See application file for complete search history.

(56) References Cited

U.S. PATENT DOCUMENTS

| | | | |
|---|---|---|---|
| 5,662,925 A | 9/1997 | Ebert et al. | 424/447 |
| 5,853,728 A | 12/1998 | Tanabe et al. | 424/195.1 |
| 5,994,413 A | 11/1999 | Tanabe et al. | 514/732 |
| 6,203,817 B1 | 3/2001 | Cormier et al. | 424/464 |
| 6,323,232 B1 | 11/2001 | Ke et al. | 514/408 |
| 6,521,668 B2 | 2/2003 | Anderson et al. | 514/679 |
| 6,572,882 B1 | 6/2003 | Vercauteren et al. | 424/451 |
| 6,805,873 B2 | 10/2004 | Gaudout et al. | 424/401 |
| 7,041,322 B2 | 5/2006 | Gaudout et al. | 424/765 |
| 7,179,841 B2 | 2/2007 | Zielinski et al. | 514/474 |
| 2003/0069302 A1 | 4/2003 | Zielinski | 514/452 |
| 2004/0037860 A1 | 2/2004 | Maillon | 424/401 |
| 2004/0091589 A1 | 5/2004 | Roy et al. | 426/265 |
| 2004/0224004 A1 | 11/2004 | Zielinski | 424/442 |
| 2005/0032882 A1 | 2/2005 | Chen | 514/456 |
| 2005/0137205 A1 | 6/2005 | Van Breen | 514/252.12 |
| 2005/0154054 A1 | 7/2005 | Zielinski et al. | 514/474 |
| 2005/0271692 A1 | 12/2005 | Gervasio-Nugent et al. | 424/401 |
| 2006/0173065 A1 | 8/2006 | Bezwada | 514/419 |
| 2006/0193790 A1 | 8/2006 | Doyle et al. | |
| 2007/0053849 A1 | 3/2007 | Doyle et al. | |
| 2007/0104808 A1 | 5/2007 | Rosenbloom | 424/729 |
| 2007/0116779 A1 | 5/2007 | Mazzio | 424/539 |
| 2007/0225360 A1 | 9/2007 | Pinnell et al. | 514/456 |
| 2007/0269576 A1 | 11/2007 | Barton et al. | 426/599 |

(Continued)

FOREIGN PATENT DOCUMENTS

| | | |
|---|---|---|
| CN | 1504215 | 6/2004 |
| EP | 1782701 | 5/2007 |

(Continued)

OTHER PUBLICATIONS

Olmedo et al., "The Issues of Corrosion in Dental Implants: A Review," Acta Odontol. Latinoam. 2009, 22(1): pp. 3-9.*
JP H05-117145—Hideko—Machine Translation by JPO.
Supplemental European Search Report; Patent Appl. No. 12835354.7-1464; 8 pages, Mar. 10, 2015.
A.L. Russell "Flouride Domestic Water and Periodontal Disease" (Am J Public Health. Jun. 1957; 47(6); 688-694), Jun. 1957.
National Institute of Dental and Craniofacial Research ("The Story of Fluoridation", National Institutes of Health, NIDCR, Feb. 26, 2014, http://www.nidcr.nih.gov/oralhealth/Topics/Fluoride/TheStoryofFluoridation.htm.), Feb. 26, 2014.

(Continued)

*Primary Examiner* — Sreeni Padmanabhan
*Assistant Examiner* — Jody Karol
(74) *Attorney, Agent, or Firm* — Baker Botts L.L.P.

(57) ABSTRACT

One embodiment of the invention is directed to a method of preventing, reducing, or eliminating at least one negative effect of oxidative damage, such as an oral disease, caused by a dental device in the mouth of a patient. Another embodiment relates to a method of preventing, reducing, or eliminating at least one negative effect of inflammation. The method may include applying topically to a soft oral tissue in the patient an oral antioxidant composition. The antioxidant composition may include between 0.0001% and 5.0% w/w or at least one antioxidant, wherein the at least one antioxidant includes a natural phytochemcial antioxidant, a flavonoid, an anthocyanidin, a dihydrochalcone, a phenylpropanoid, a chalcone, a curcuminoid, a tannin, a stilbenoid, a coumarin, a carotenoid, or a vitamin, and an orally pharmaceutically acceptable carrier. The pH of the oral antioxidant composition may be at least 5.0.

12 Claims, 24 Drawing Sheets

(56) References Cited

U.S. PATENT DOCUMENTS

| | | |
|---|---|---|
| 2008/0033027 A1 | 2/2008 | Bascomb et al. ............. 514/411 |
| 2008/0159970 A1 | 7/2008 | Willemin ......................... 424/59 |
| 2008/0227867 A1 | 9/2008 | Ley et al. ...................... 514/685 |
| 2009/0018200 A1 | 1/2009 | Willemin et al. .............. 514/576 |
| 2009/0092644 A1 | 4/2009 | Shiroyama et al. ........... 424/401 |
| 2009/0208431 A1 | 8/2009 | Bommarito ...................... 424/59 |
| 2009/0269395 A1 | 10/2009 | Lintner et al. ................. 424/450 |
| 2009/0286874 A1 | 11/2009 | Pinnell et al. ................. 514/474 |
| 2009/0311197 A1 | 12/2009 | Romanowski et al. |
| 2010/0150853 A1 | 6/2010 | Cassin et al. ................... 424/59 |
| 2010/0166897 A1 | 7/2010 | Laboureau et al. ........... 424/770 |
| 2010/0183524 A1* | 7/2010 | Zielinski ................ A61K 8/347 424/55 |
| 2010/0255079 A1 | 10/2010 | San Miguel et al. .......... 424/450 |
| 2011/0015463 A1 | 1/2011 | Legendre et al. .................. 600/9 |

FOREIGN PATENT DOCUMENTS

| | | | |
|---|---|---|---|
| EP | 1837056 | 9/2007 | ............. A61Q 19/08 |
| EP | 1925311 | 5/2008 | ............ A61K 36/185 |
| GB | 2 317 339 A | 3/1998 | ............... A61K 8/19 |
| JP | 5117145 | 5/1993 | ............. A61K 31/19 |
| JP | 2000016951 | 1/2000 | ............. C07B 63/00 |
| JP | 2003212774 | 7/2003 | |
| JP | 2004231602 | 8/2004 | |
| WO | WO 99/00106 A1 | 1/1999 | ............ A61K 31/195 |
| WO | WO 00/38620 | 7/2000 | |
| WO | WO 00/61162 | 10/2000 | ............. A61K 35/78 |
| WO | WO 02/081651 | 10/2002 | |
| WO | WO 2005/004630 | 1/2005 | |
| WO | WO 2005/084305 | 9/2005 | |
| WO | WO 2006/083666 | 8/2006 | |
| WO | WO 2007/042835 | 4/2007 | |
| WO | 2007/064755 A2 | 6/2007 | |
| WO | WO 2007/107596 | 9/2007 | ............. C07C 49/84 |
| WO | WO 2007/132190 | 11/2007 | ............ A61K 31/121 |
| WO | WO 2008/001325 | 1/2008 | |
| WO | WO 2008/058999 | 5/2008 | |
| WO | WO 2008/090489 | 7/2008 | |
| WO | WO 2008/120220 | 10/2008 | |

OTHER PUBLICATIONS

Bagramian et al., The global increase in dental caries. A pending public health crisis, (American Journal of Dentistry, vol. 22, No. 1, Feb. 2009, pp. 3-8, Feb. 2009.

Simple Steps: to Better Dental Health, Mar. 7, 2014, http:/www.simplestepsdental.com/SS/ihtSSPrint/r.==/st.31851/t.32544/pr.3/c.307683.html, Mar. 7, 2014.

American Academy of Periodontology ("Half of American Adults Have Periodontal Disease", http://www.perio.org/consumer/cdc-study.htm, Sep. 4, 2012.

National Institute of Dental and Craniofacial Research (NIDCR) "Treatment Outcomes of Oral Diseases in Medically Complex Patients", Center for Clinical Research Divisionof Extramural Research) http://www.nidcr.nih.gov/grantsandfunding/See$_L$ $_{Funding}$ Opportunities_Sorted_By/ConceptClearance/CurrentCC/TreatmentOutcomes.htm) Feb. 26, 2014.

Seattle Children's Hospital: Research Foundation (Chromosomal and Genetic Conditions: "Cleft Lip and Cleft Palate Treatment", http://www.seattlechildrens.org/medical-conditions/chromosomal-genetic-conditions/cleft-lip-palate-treatment/) Feb. 11, 2015.

Trisha Gura, "Cancer Models: Systems for identifying New Drugs Are Often Faulty" (Science, vol. 278, pp. 1041-1042, 1997.

Johnson et al., "Relationships between drug activity in NCI preclinical in vitro and in vivo models and early clinical trials", British Journal of Cancer, vol. 84(10), pp. 1424-1431, 2001.

Gupta et al., Angiogenesis: a curse or cure?, Postgrad. Med. J., vol. 81, pp. 236-242, 2005.

Ohri et al., Tumour necrosis factor-alpha expression in tumour islets confers a survival advantage in non-small cell lung cancer BMC Cancer 2010, 10:323, 9 pages, 2010.

Australian Office Action issued in Appl. No. 2012315782; 3 pages, Apr. 27, 2015.

International Preliminary Report on Patentability; PCT/US2012/057824; pp. 10, Apr. 10, 2014.

D. Sculley et al., "Salivary Antioxidants and Periodontal Disease Status", Proceedings of the Nutrion Society, vol. 61, Issue 1, pp. 137-143, 2002.

Hershkovich et al. Age-related changes in salivary antioxidant profile: possible implications for oral cancer. J Gerontol A Biol Sci Med Sci Apr. 2007;62(4):361-6, Feb. 2007.

M. Battino et al., "The Antioxidant Capacity of Saliva", Journal of Clinical Periodontology, vol. 29, Issue 3, pp. 189-194, Mar. 2002.

I. Chapple, "Low Antioxidant Levels Associated with Periodontal Disease", Journal of American Dental Association, vol. 134, No. 1, 2003.

I. Chapple et al., "Reactive Oxygen Species and Antioxidants in Inflammatory Diseases", Journal of Clinical Periodontology, vol. 24, Issue 5, pp. 287-296, May 2007.

N. Kinoshita et al., "Interaction between dental metals and antioxidants, assessed by cytotoxicity assay and ESR spectroscopy", International Journal of Cancer Research and Treatment, 2002.

Y. Tai et al., "Protective effect of lecithinized SOD on reactive oxygen species-induced xerostomia", Radiation Research, vol. 172, No. 3, pp. 331-338, Sep. 2009.

Balakrishnan et al.; "Effect of curcumin and ferulic acid on modulation of expression pattern of p53 and bcl-proteins in 7, 12-dimethylbenz[α]anthracene-induced hamster buccal pouch carcinogenesis"; Indian Journal of Biochemistry & Biophysics; vol. 47; pp. 7-12, 2010.

Specification of an invention patent application of China; Application No. 02150897.6; pp. 15, Nov. 29, 2002.

Nutrition Fights Gum Disease; http://www.quantumhealth.com/news/articlegums.html; Quantum Health, accessed Feb. 7, 2010; 3 pages, Feb. 7, 2010.

Sculley DV, Langley-Evans SC. Periodontal disease is associated with lower antioxidant capacity in whole saliva and evidence of increased protein oxidation, Clin Sci (Lond) Aug. 2003;105(2):167-72.

Borges I, Jr., Moreira EA, Filho DW, de Oliveira TB, da Silva MB, Frode TS. Proinflammatory and oxidative stress markers in patients with periodontal disease. Mediators Inflamm 2007;2007:45794.

M. Battino, M. S. Ferreiro, J. L. Quiles, S. Rompadre, L. Leone, and P. Billion, "Alterations in the oxidation products, antioxidant markers, antioxidant capacity and lipid patterns in plasma of patients affected by Papillon-Lefèvre syndrome," Free Radical Research, vol. 37, No. 6, pp. 603-609, 2003.

R. J. Waddington, R. Moseley, and G. Embery, "Reactive oxygen species: a potential role in the pathogenesis of periodontal diseases," *Oral Diseases*, 2000, vol. 6, No. 3, pp. 138-151, 2000.

H. Katsuragi, M. Ohtake, I. Kurasawa, and K. Saito, "Intracellular production and extracellular release of oxygen radicals by PMNs and oxidative stress on PMNs during phagocytosis of periodontopathic bacteria," Odontology, vol. 91, No. 1, pp. 13-18, 2003.

U. Sakallioğlu, E. Aliyev, Z. Eren, G. Akş imş ek, I. Keskiner, and Ü. Yavuz, "Reactive oxygen species scavenging activity during periodontal mucoperiosteal healing: an experimental study in dogs," Archives of Oral Biology, vol. 50, No. 12, pp. 1040-1046, 2005.

M. Takane, N. Sugano, H. Iwasaki, Y. Iwano, N. Shimizu, and K. Ito, "New biomarker evidence of oxidative DNA damage in whole saliva from clinically healthy and periodontally diseased individuals," Journal of Periodontology, vol. 73, No. 5, pp. 551-554, 2002.

B. Halliwell and J. M. C. Gutteridge, "Free radicals, other reactive species and disease," in *Free Radicals in Biology and Medicine*, pp. 617-783, Clarendon Press, Oxford, UK, 1998.

M. L. Wang, P. V. Hauschka, R. S. Tuan, and M. J. Steinbeck, "Exposure to particles stimulates superoxide production by human THP-1 macrophages and avian HD-11EM osteoclasts activated by tumor necrosis factor-α and PMA," Journal of Arthroplasty, vol. 17, No. 3, pp. 335-346, 2002.

I. L. Chapple, "Role of free radicals and antioxidants in the pathogenesis of the inflammatory periodontal diseases," Clinical Molecular Pathology, vol. 49, No. 5, pp. 247-255, 1996.

(56) References Cited

OTHER PUBLICATIONS

Honda, H. Domon, T. Okui, K. Kajita, R. Amanuma, and K. Yamazaki, "Balance of inflammatory response in stable gingivitis and progressive periodontitis lesions," Clinical and Experimental Immunology, vol. 144, No. 1, pp. 35-40, 2006.
H. Aebi, "Catalase in vitro," *Methods in Enzymology*, vol. 105, pp. 121-126, 1984.
L. Flohé and W. A. Gunzler, "Assays of glutathione peroxidase," *Methods in Enzymology*, vol. 105, pp. 114-121, 1984.
W. H. Habig, M. J. Pabst, and W. B. Jakoby, "Glutathione S-transferases: the first enzymatic step in mercapturic acid formation," *Journal of Biological Chemistry*, vol. 249, No. 22, pp. 7130-7139, 1974.
I. Carlberg and B. Mannervik, "Glutathione reductase," in *Methods in Enzymology*, A. Meiste, Ed., pp. 484-490, Academic Press, New York, NY, USA, 1993.
F. Tictzc, "Enzymic method for quantitative determination of nanogram amounts of total and oxidized glutathione: applications to mammalian blood and other tissues," Analytical Biochemistry, vol. 27, No. 3, pp. 502-522, 1969.
T. S. Rao, J. L. Currie, A. F. Shaffer, and P. C. Isakson, "Comparative evaluation of arachidonic acid (AA)- and tetradecanoylphorbol acetate (TPA)-induced dermal inflammation," Inflammation, vol. 17, No. 6, pp. 723-741, 1993.
R. P. Bird and H. H. Draper, "Comparative studies on different methods of malonaldehyde determination," Methods in Enzymology, vol. 105, pp. 299-305, 1984.
G. R. Brock, C. J. Butterworth, J. B. Matthews, and I. L. Chapple, "Local and systemic total antioxidant capacity in periodontitis and health," Journal of Clinical Periodontology, vol. 31, No. 7, pp. 515-521, 2004.
S. D. Ellis, M. A. Tucci, F. G. Serio, and R. B. Johnson, "Factors for progression of periodontal diseases," *Journal of Oral Pathology and Medicine*, vol. 27, No. 3, pp. 101-105, 1998.
K. Panjamurthy, S. Manoharan, and C. R. Ramachandran, "Lipid peroxidation and antioxidant status in patients with periodontitis," *Cellular & Molecular Biology Letters*, vol. 10, No. 2, pp. 255-264, 2005.
K. H. Cheeseman and T. F. Slater, "An introduction to free radical biochemistry," *British Medical Bulletin*, vol. 49, No. 3, pp. 481-493, 1993.
Y. Sagara, R. Dargusch, D. Chambers, J. Davis, D. Schubert, and P. Maher, "Cellular mechanisms of resistance to chronic oxidative stress," Free Radical Biology and Medicine, vol. 24, No. 9, pp. 1375-1389, 1998.
B. Halliwell and J. M. C. Gutteridge, "The chemistry of free radicals and related reactive species," in *Free Radicals in Biology and Medicine*, pp. 36-104, Clarendon Press, Oxford, UK, 1999.
G. Noctor and C. H. Foyer, "Ascorbate and gluthatione: keeping active oxygen under control," Annual Review of Plant Physiology and Plant Molecular Biology, vol. 49, pp. 249-279, 1998.
J. Carlsson, J. T. Larsen, and M. B. Edlund, "Peptostreptococcus micros has a uniquely high capacity to form hydrogen sulfide from glutathione," Oral Microbiology and Immunology, vol. 8, No. 1, pp. 42-45, 1993.
J. Carlsson, J. T. Larsen, and M. B. Edlund, "Utilization of glutathione (L-γ-glutamyl-L-cysteinylglycine) by *Fusobacterium nucleatum* subspecies *nucleatum*," Oral Microbiology and Immunology, vol. 9, No. 5, pp. 297 300, 1994.
I. L. C. Chapple, G. Brock, C. Eftimiadi, and J. B. Matthews, "Glutathione in gingival crevicular fluid and its relation to local antioxidant capacity in periodontal health and disease," Journal of Clinical Pathology, vol. 55, No. 6, pp. 367-373, 2002.
B. Halliwell and J. M. C. Gutteridge, "Detection of free radicals and other reactive species: trapping and fingerprinting," in *Free Radicals in Biology and Medicine*, pp. 393-412, Clarendon Press, Oxford, UK, 1999.
P.-F. Wei et al., "The investigation of glutathione peroxidase, lactoferrin, myeloperoxidase and interleukin-1β in gingival crevicular fluid: implications for oxidative stress in human periodontal diseases," Journal of Periodontal Research, vol. 39, No. 5, pp. 287-293, 2004.
Morita; Tobacco smoke causes premature skin aging.; The Journal of Dermatological Science, vol. 48, Issue 3, pp. 169-175 (Dec. 2007).
Dr. Maryam Sheikhi, "Lipid peroxidation caused by oxygen radicals for Fusobacterium-stimulated neutrophils as a possible model for the emergence of periodontitis", Oral Diseases, 7:41-46, 2001.
Dr. Masatomo Hirasawa, "Improvement of periodontal status by green tea catechin using a local delivery system: A clinical pilot study."; J. Periodont. Res. 37:433-438, 2002.
Tezal et al.; Jul. 2005 issue of *Journal of Periodontology*; Periodontal Disease and the incidence of Tooth Loss in Postmenopausal Women; pp. 6, 2005.
International Association for Dental Research meeting held Mar. 10-13, 2004 in Hawaii. Supplement Containing Vitamins C, E and Grape Seed Extract Improves Smokers' Response to Gum Disease Treatment presented by Sara Grossi, DDS, MS, 2004.
American Association of Dental Research and International Association of Dental Research held Mar. 13, 1999; University of Buffalo Oral Biologists Find Link Between Gum Disease and Passive Exposure to Tobacco Smoke, Dr. Sara Grossi.
Grossi et al.; Effects of Smoking and Smoking Cessation on healing After Mechanical Periodontal Therapy; JADA, vol. 128, May 1997.
Kushiyama et al., Relationship between intake of green tea and periodontal disease. Journal of Periodontology; 2009, vol. 80, No. 3, pp. 372-377.
J Dent Res. May 2008;87(5):456-60; "Effects of ethanol consumption on periodontal inflammation in rats"; Irie K, Tomofuji T, Tamaki N, Sanbe T, Ekuni D, Azuma T, Maruyama T, Yamamoto T.
Arch Immunol Ther Exp (Warsz). Nov.-Dec. 2007;55(6):417-22. Epub Dec. 3, 2007.; "Total antioxidant status and 8-hydroxy-2'-deoxyguanosine levels in gingival and peripheral blood of periodontitis patients."; Konopka T, Król K, Kopeć W, Gerber H.
J Periodontol. Nov. 2006;77(11):1894-900; "New evidence of premature oxidative DNA damage: mitochondrial DNA deletion in gingival tissue of patients with periodontitis"; Canakçi CF, Tatar A, Canakçi V, Cicek Y, Oztas S, Orbak R.
J Biomed Mater Res B Appl Biomater. Feb. 2007;80(2):499-504; "Induction of heme oxygenase-1 expression by root canal sealers in human gingival fibroblasts is augmented by oxidative stress"; Huang FM, Chang YC.
Biomaterials. Sep. 2005;26(25):5130-7; "TEGDMA induces mitochondrial damage and oxidative stress in human gingival fibroblasts"; Lefeuvre M, Amjaad W, Goldberg M, Stanislawski L.
"UV photoprotection by combination topical antioxidants vitamin C and vitamin E"; Jing-Yi Lin, M.Angelica Selim, Christopher R. Shea, James M. Grichnik, Mostafa M. Omar, Nancy A. Monteiro-Riviere, Sheldon R. Pinnell *Journal of the American Academy of Dermatology* Jun. 2003 (vol. 48, Issue 6, pp. 866-874).
"A topical antioxidant solution containing vitamins C and E stabilized by ferulic acid provides protection for human skin against damage caused by ultraviolet irradiation", Jul. 7, 2008 John C. Murry, James A. Burch, Robert D. Streilein, Mary Ann Iannacchione, Russell P. Hall, Sheldon R. Pinnell *Journal of the American Academy of Dermatology* Sep. 2008 (vol. 59, Issue 3, pp. 418-425).
"Cutaneous photodamage, oxidative stress, and topical antioxidant protection" Sheldon R. Pinnell *Journal of the American Academy of Dermatology* Jan. 2003 (vol. 48, Issue 1, pp. 1-19).
"Uses of vitamins A, C, and E and related compounds in dermatology: A review"; Karen Laszlo Keller, Neil A. Fenske *Journal of the American Academy of Dermatology* Oct. 1998 (vol. 39, Issue 4, pp. 611-625).
"Menopause: A review on the role of oxygen stress and favorable effects of dietary antioxidants", Jan. 30, 2006 Jaime Miquel, Ana Ramírez-Boscá, Juan V. Ramírez-Bosca, Joaquin Diaz Alperi Archives of Gerontology and Geriatrics May 2006 (vol. 42, Issue 3, pp. 289-306).
Goraca and Skibska, "Plasma antioxidant status in healthy smoking and non-smoking men"; Bratisl Lek Listy 2005 (vol. 106, Issue 10, pp. 301-306).

(56) References Cited

OTHER PUBLICATIONS

Frei B.; "Reactive oxygen species and antioxidant vitamins: Mechanisms of action"; Am J Med. 1994;97(Suppl 3A):5S-13S.

Sudheer et al. Protective effect of ferulic acid on nicotine induced DNA damage and cellular changes in cultured rat peripheral blood lymphocytes: A comparison with N-acetylcysteine; Toxicology in Vitro, vol. 21, Issue 4, Jun. 2007, pp. 576-585.

Ishida, M., Nambu, N., and Nagai, T., "Mucosal dosage form of lidocaine for toothache using hydroxypropyl cellulose and carbopol"; *Chem. Pharm. Bull.*, 30:980-984, 1982.

Collins, A.E.M., Deasy, P.B., Mac Carthy, D.J., and Shanley, D.B., "Evaluation of a controlled release compact containing tetracycline hydrochloride bonded to tooth for the treatment of periodontal disease"; *Int. J. Pharm.*, 51:103-114, 1989.

Elkayam, R., Friedman, M., Stabholz, A., Soskolne, A.w., Sela, M.N., and Golub, L., "Sustained release device containing minocycline for local treatment of periodontal disease"; *J. Control. Rel.*, 7:231-236, 1988.

Samaranayake, L. and Ferguson, M., "Delivery of antifungal agents to the oral cavity"; *Adv. Drug Del. Rev.*, 13:161-179, 1994.

Nagai, T., Adhesive topical drug delivery system, *J. Control. Rel.*, 2:121-134, 1985.

Galey, W.R., Lonsdale, H.K., and Nacht, S., The in vitro permeability of skin and buccal mucosa to selected drugs and tritiated water, *J. Invest. Dermat.*, 67:713-717, 1976.

Harris, D. and Robinson, J.R., Drug delivery via the mucous membranes of the oral cavity, *J. Pharm. Sci.*, 81:1-10, 1992.

Tabak, L.A., Levine, M.J., Mandel, I.D., and Ellison, S.A., "Role of salivary mucins in the protection of the oral cavity", *J. Oral Pathol.*, 11:1-17, 1982.

Rathbone, M., Drummond, B., and Tucker, I., Oral cavity as a site for systemic drug delivery, *Adv. Drug Del. Rev.*, 13:1-22, 1994.

"Chemical enhancement of percutaneous absorption in relation to stratum corneum structural alterations", Journal of Controlled Release vol. 59 Issue 2, May 20, 1999 pp. 149-161, T. Marjukka, Suhonen, Joke A Bouwstra and Arlo Urtti.

Bos and Meinardi, The 500 Dalton rule for the skin penetration of chemical compounds and drugs. Experimental Dermatology, vol. 9, No. 3, Jun. 2000, pp. 165-169.

Lin, F-H., Lin, J-Y., Gupta, R.D., Tournas, J.A., Burch, J.A., Selim, M.A., Monteiro-Riviere, N.A., Grichnik, J.M., Zielinski, J. and S.R. Pinnel; "Ferulic Acid Stablizes a Solution of Vitamins C and C and Doubles its Photoprotection of Skin"; J. Invest. Dermatol. 125:826 (2005).

Halliwell B.; "Antioxidants: the basics—what they are and how to evaluate them"; Adv Pharmacol 1997;38:3-20.

Carnelio S, Khan SA, Rodrigues G. Definite, probable or dubious: antioxidants trilogy in clinical dentistry. Br Dent J Jan. 12, 2008;204(1):29-32.

Chapple IL, Brock GR, Milward MR, Ling N, Matthews JB. Compromised GCF total antioxidant capacity in periodontitis: cause or effect? J Clin Periodontol Feb. 2007;34(2):103-10.

Hershkovich O, Shafat I, Nagler RM. Age-related changes in salivary antioxidant profile: possible implications for oral cancer. J Gerontol A Biol Sci Med Sci Apr. 2007;62(4):361-6.

Moore S, Calder KA, Miller NJ, Rice-Evans CA. Antioxidant activity of saliva and periodontal disease. Free Radic Res Nov.-Dec. 1994;21(6):417-25.

Nagler RM, Klein I, Zarzhevsky N, Drigues N, Reznick AZ. Characterization of the differentiated antioxidant profile of human saliva. Free Radic Biol Med Feb. 1, 2002;32(3):268-77.

Dayan D, Hirshberg A, Kaplan I, Rotem N, Bodner L. Experimental tongue cancer in desalivated rats. Oral Oncol Mar. 1997;33(2):105-9.

Wu HJ, Chi CW, Liu TY. Effects of pH on nicotine-induced DNA damage and oxidative stress. J Toxicol Environ Health A Sep. 2005;68(17-18):1511-23.

Nishioka H, Nishi K, Kyokane K. Human saliva inactivates mutagenicity of carcinogens. Mutat Res Oct. 1981;85(5):323-33.

Reznick et al. Saliva—a pivotal player in the pathogenesis of oropharyngeal cancer. Br J Cancer Jul. 5, 2004;91(1):111-8.

Giannobile WV. Host-response therapeutics for periodontal diseases. J Periodontol Aug. 2008;79(8 Suppl):1592-600.

Kinane DF, Mark Bartold P. Clinical relevance of the host responses of periodontitis. Periodontol 2000 2007;43:278-93.

Harvey et al. Subgingival bacteria—comparison of culture results in dogs and cats with gingivitis. J Vet Dent Dec. 1995;12(4):147-50.

DuPont GA. Understanding dental plaque; biofilm dynamics. J Vet Dent Sep. 1997;14(3):91-4.

Brecx et al. Morphological studies on periodontal disease in the cynomolgus monkey. III. Electron microscopic observations. J Periodontal Res Mar. 1986;21(2):137-5.

Izumita Don, The First International EM Medical Conference in Okinawa Japan; Clinical and Basic Medical Research on EM-X-A Collection of Research Papers, vol. 2, pp. 77-81, Nov. 2001.

Vertuani S, Angusti A, Manfredini S (2004). "The antioxidants and pro-antioxidants network: an overview". Curr Pharm Des 10 (14): 1677-94.

Battino M, Bullon P, Wilson M, Newman H. Oxidative injury and inflammatory periodontal diseases: the challenge of anti-oxidants to free radicals and reactive oxygen species. Crit Rev Oral Biol Med 1999;10(4):458-76.

Baltacioglu E, Akalin FA, Alver A, Deger O, Karabulut E. Protein carbonyl levels in serum and gingival crevicular fluid in patients with chronic periodontitis. Arch Oral Biol Aug. 2008;53(8):716-22.

Singer et al. Association of Systemic Oxidative Stress with Suppressed Serum IgG to Commensal Oral Biofilm and Modulation by Periodontal Infection. Antioxid Redox Signal, vol. 11, No. 12, pp. 2973-2984, 2009.

Giannopoulou C, Krause KH, Muller F. The NADPH oxidase NOX2 plays a role in periodontal pathologies. Semin Immunopathol Jul. 2008;30(3):273-8.

Tamaki N, Tomofuji T, Maruyama T, Ekuni D, Yamanaka R, Takeuchi N, et al. Relationship between periodontal condition and plasma reactive oxygen metabolites in patients in the maintenance phase of periodontal treatment. J Periodontol Nov. 2008;79(11):2136-42.

Tamaki N, Tomofuji T, Ekuni D, Yamanaka R, Yamamoto T, Morita M.J Periodontol. Jun. 2009;80(6):901-6. Links Short-term effects of non-surgical periodontal treatment on plasma level of reactive oxygen metabolites in patients with chronic periodontitis.

Patel SP, Pradeep AR, Chowdhry S. Crevicular fluid levels of plasma glutathione peroxidase (eGPx) in periodontal health and disease. Arch Oral Biol Jun. 2009;54(6):543-8.

Tuter G, Kurtis B, Serdar M. Interleukin-1 beta and thiobarbituric acid reactive substance (TBARS) levels after phase I periodontal therapy in patients with chronic periodontitis. J Periodontol Jul. 2001;72(7):883-8.

Soskolne. Epidemiological and clinical aspects of periodontal diseases in diabetics. Ann Periodontol. Jul. 1998;3(1):3-12.

Soskolne and Klinger, The relationship between periodontal diseases and diabetes: an overview. Ann Periodontol. Dec. 2001;6(1):91-8.

Mustapha IZ, Debrey S, Oladubu M, Ugarte R Markers of systemic bacterial exposure in periodontal disease and cardiovascular disease risk: a systematic review and meta-analysis. J Periodontol. Dec. 2007;78(12):2289-302.

Noack B, Genco RJ, Trevisan M, Grossi S, Zambon JJ, De Nardin E. Periodontal infections contribute to elevated systemic C-reactive protein level. J Periodontol. Sep. 2001;72(9):1221-7.

Seymour et al. Relationship between periodontal infections and systemic disease. Clin Microbiol Infect. Oct. 2007;13 Suppl 4:3.

Midori Kashima-Tanaka, Y Tsujimoto, Kohji Kawamoto, Naoki Sneda, Koichi Ito, Muneyoshi Yamazaki, Generation of Free Radicals and/or active Oxygen by Light or Laser Irradiation of Hydrogen peroxide or Sodium Hypochlorite, J Endod. Feb. 2003;29(2):141-3. 2003.

Ruyter IE. Physical and chemical aspects related to substances released from polymer materials in an aqueous environment. Adv Dent Res 1995;9:344-7.

(56) References Cited

OTHER PUBLICATIONS

Slaga TJ, Klein-Szanto AJ, Triplett LL, Yotti LP, Trosko KE. Skin tumor-promoting activity of benzoyl peroxide, a widely used free radical-generating compound. Science Aug. 28, 1981; 213 (4511):1023-5.

Bonfil RD, Momiki S, Conti CJ, Klein-Szanto AJ. Benzoyl peroxide enhances the invasive ability of a mouse epidermal carcinoma cell line. Int J Cancer Jul. 15, 1989;44(1):165-9.

Geurtsen W, Lehmann F, Spahl W, Leyhausen G. Cytotoxicity of 35 dental resin composite monomers/additives in permanent 3T3 and three human primary fibroblast cultures. J Biomed Mater Res Sep. 5, 1998;41(3):474-80.

Markowitz K, Moynihan M, Liu M, Kim S. Biologic properties of eugenol and zinc oxide-eugenol. A clinically oriented review. Oral Surg Oral Med Oral Pathol Jun. 1992;73(6):729-37.

Fujisawa S, Atsumi T, Kadoma Y, Sakagami H. Antioxidant and prooxidant action of eugenol-related compounds and their cytotoxicity. Toxicology Aug. 1, 2002;177(1):39-54.

Wahl Michael, Amalgam-Resurrection and Redemption Part 2: The Medical Mythology of Anti-Amalgam Dental Watch Home Page, http://www.dentalwatch.org/hg/myths200.html; 2 page, 2011.

Blaschke Christian, Metal-free dental implants—A new approach to implantology, The New Zealand Charter Journal, Spring 2004, p. 17-18.

Placko HE, Perry W, Mishra S, Lucas LC, Weimer JJ. Surface studies of titanium-based dental implant materials. J Dent Res 76 (1997), p. 1514.

Placko HE, Mishra S, Weimer JJ, Lucas LC. Surface characterization of titanium-based dental implant materials. Int J Oral Maxillofac Implants 2000; 15:355-63.

Ding HM, Ram MK, Nicolini C. Nanofabrication of organic and inorganic hybrids of $TiO_2$ with substituted phthalocyanine or polythiphene. J Nanosci Nanotechnol. Jun. 2001;1(2):207-13.

Ding RG, Lu GQ, Yan ZF, Wilson MA. Recent advances in the preparation and utilization of carbon nanotubes for hydrogen storage. J Nanosci Nanotechnol Mar. 2001;1(1):7-29.

Wu TX, Liu GM, Zhao JC, Hidaka H, Serpone N. Photoassisted degradation of dye pollutants V. Self-photosensitized oxidative transformation of Rhodamine B under visible light irradiation in aqueous $TiO_2$ dispersions. Environ. Sci. Technol., 1998, 32 (16), pp. 2394-2400.

Wu TX, Liu GM, Zhao JC, Hidaka H, Serpone N. Evidence for $H_2o_2$ generation during the $TiO_2$-assisted photodegradation of dyes in aqueous dispersions under visible light illumination J Phys Chem B 1999;103;4862-7.

Ohko Y, Utsumi Y, Niwa C, Tatsuma T, Kobayakawa K, Satoh Y, et al. Self-sterilizing and self-cleaning of silicone catheters coated with $TiO(2)$ photocatalyst thin films: a preclinical work. J Biomed Mater Res 2001;58(1):97-101.

Tatsuma T, takeda, S, Saitoh, S, Ohko Y, Fujishima A. bactericidal Effect of an energy storage $TiO_2$-$Wo_3$ photocatalyzt in dark. Electrochem Commun 2003; 5: 793-6.

Riley DJ, Bavastrello V, Covani U, Barone A, Nicolini C. An in-vitro study of the sterilization of titanium dental implants using low intensity UV-radiation. Dent Mater Aug. 2005;21(8):756-60.

Gonzalez R, Arancibia R, Cáceres M, Martínez J, Smith PC. Cigarette smoke condensate stimulates urokinase production through the generation of reactive oxygen species and activation of the mitogen activated protein kinase pathways in human gingival fibroblasts. J Periodontal Res. Jun. 2009;44(3):386-94.

Dietrich T, Bernimoulin JP, Glynn RJ The effect of cigarette smoking on gingival bleeding J Periodontol. Jan. 2004;75(1):16-22.

Baljoon M, Tobacco smoking and vertical periodontal bone loss. Swed Dent J Suppl. 2005;(174):1-62.

Johnson Georgia K. Cigarette Smoking and the Periodontal Patient, Journal of Periodontology, Feb. 2004, vol. 75, No. 2, pp. 196-209.

Wan CP, et al. Effects of smoking on healing response to non-surgical periodontal therapy: a multilevel modelling analysis . . . J Clin Periodontol. Mar. 2009;36(3):229-39.

Chang YC, Huang FM, Tai KW, Yang LC, Chou MY Mechanisms of cytotoxicity of nicotine in human periodontal ligament fibroblast cultures in vitro . . . J Periodontal Res. Aug. 2002;37(4):279-85.

Griannopoulou C, Geinoz A, Cimasoni G. Effects of nicotine on periodontal ligament fibroblasts in vitro. J Clin Periodontol. Jan. 1999;26(1):49-55.

James JA, Sayers NM, Drucker DB, Hull PS. J Effects of tobacco products on the attachment and growth of periodontal ligament fibroblasts. Periodontol. May 1999;70(5):518-25.

Eggert Michael F. Effects of Smoking and Treatment Status on Periodontal Bacteria: Evidence That Smoking Influences Control of Periodontal Bacteria at the Mucosal Surface of the Gingival Crevice , Journal of Periodontology, Sep. 2001, vol. 72, No. 9, pp. 1210-1220.

Papantonopoulos George H. Smoking Influences Decision Making in Periodontal Therapy: A Retrospective Clinical Study, Journal of Periodontology; Oct. 1999, vol. 70, No. 10, pp. 1166-1173.

Albandar Jasim M. , Charles F. Streckfus Margo R. Adesanya Deborah M. Winn Cigar, Pipe, and Cigarette Smoking as Risk Factors for Periodontal Disease and Tooth Loss, Journal of Periodontology Dec. 2000, vol. 71, No. 12, pp. 1874-1881.

Agnihotri R, Pandurang P, Kamath SU, Goyal R, Ballal S, Shanbhogue AY, et al. Association of cigarette smoking with superoxide dismutase enzyme levels in subjects with chronic periodontitis. J Periodontol Apr. 2009;80(4):657-62.

González YM, De Nardin A, Grossi SG, Machtei EE, Genco RJ, De Nardin E. Serum cotinine levels, smoking, and periodontal attachment loss. J Dent Res. Feb. 1996;75(2):796-802.

Song SM, Park YS, Lee A, Cho YG, Kim DS, Lee HS, et al. [Concentrations of blood vitamin a, C, e, coenzyme q10 and urine cotinine related to cigarette smoking exposure.]. Korean J Lab Med Feb. 2009;29(1):10-6.

Alpar B, Leyhausen G, Sapotnick A, Gunay H, Geurtsen W. Nicotine-induced alterations in human primary periodontal ligament and gingiva fibroblast cultures. Clin Oral Investig Mar. 1998;2(1):40-6.

Fang Y ,Svoboda KKH. Nicotine inhibits myofibroblast differentiation in human gingival fibroblasts. J Cell Biochem 2005;95;1108-19.

Fang Y ,Svoboda KKH. Nicotine inhibits human gingival fibroblast migration via modulation of rac signalling pathways. J Clin Periodontol 2005;32; 1200-7.

Xu, 2003 Effects of tobacco on proliferation and attachment of human periodontal ligament fibroblast Zhonghua Kou Qiang Yi Xuc Za Zhi. Sep. 2003;38(5):367-9.

Gamal AY, Bayomy MM. Effect of cigarette smoking on human PDL fibroblasts attachment to periodontally involved root surfaces in vitro. J Clin Periodontol Aug. 2002;29(8):763-70.

Figuero E, Soory M, Cerero R, Bascones A. Oxidant/antioxidant interactions of nicotine, Coenzyme Q10, Pyenogenol and phytoestrogens in oral periosteal fibroblasts and MG63 osteoblasts. Steroids Dec. 2006;71(13-14):1062-72.

Cabrera C, Artacho R, Gimenez R. Beneficial effects of green tea—a review. J Am Coll Nutr. Apr. 2006;25(2):79-99.

Abebe W. An overview of herbal supplement utilization with particular emphasis on possible interactions with dental drugs and oral manifestations. J Dent Hyg. 2003 Winter;77(1):37-46.

Babich H, Gottesman RT, Liebling EJ, Schuck AG. Theaflavin-3-gallate and theaflavin-3'-gallate, polyphenols in black tea with prooxidant properties. Basic Clin Pharmacol Toxicol Jul. 2008;103(1):66-74.

Houde V, Grenier D, Chandad F. Protective effects of grape seed proanthocyanidins against oxidative stress induced by lipopolysaccharides of periodontopathogens. J Periodontol Aug. 2006;77(8):1371-9.

Mallery SR, Zwick JC, Pei P, Tong M, Larsen PE, Shumway BS, et al. Topical application of a bioadhesive black raspberry gel modulates gene expression and reduces cyclooxygenase 2 protein in human premalignant oral lesions. Cancer Res Jun. 15, 2008;68(12):4945-57.

(56) References Cited

OTHER PUBLICATIONS

Gutierrez-Venegas G, Kawasaki-Cardenas P, Arroyo-Cruz SR, Maldonado-Frias S. Luteolin inhibits lipopolysaccharide actions on human gingival fibroblasts. Eur J Pharmacol Jul. 10, 2006;541(1-2):95-105.
Srinivasan M, Sudheer AR, Menon VP. Ferulic Acid: therapeutic potential through its antioxidant property. J Clin Biochem Nutr. Mar. 2007;40(2):92-100.
Balakrishnan S, Menon VP, Manoharan S. Ferulic acid inhibits 7,12-dimethylbenz[a]anthracene-induced hamster buccal pouch carcinogenesis. J Med Food. Dec. 2008;11(4):693-700.
Graf E. Antioxidant potential of ferulic acid. Free Radic Biol Med Oct. 1992;13(4):435-48.
Tanaka T, Kohno H, Nomura E, Taniguchi H, Tsuno T, Tsuda H. A novel geranylated derivative, ethyl 3-(4'-geranyloxy-3'-methoxyphenyl)-2-propenoate, synthesized from ferulic acid suppresses carcinogenesis and inducible nitric oxide synthase in rat tongue. Oncology 2003;64(2):166-75.
Ogiwara T, Satoh K, Kadoma Y, Murakami Y, Unten S, Atsumi T, et al. Radical scavenging activity and cytotoxicity of ferulic acid. Anticancer Res Sep.-Oct. 2002;22(5):2711-7.
Chapple IL, Matthews JB. The role of reactive oxygen and antioxidant species in periodontal tissue destruction. Periodontol 2000. 2007;43:160-232.
Royack GA, Nguyen MP, Tong DC, Poot M, Oda D. Response of human oral epithelial cells to oxidative damage and the effect of vitamin E. Oral Oncol Jan. 2000;36(1):37-41.
Yu YH, Kuo HK, Lai YL. The association between serum folate levels and periodontal disease in older adults: data from the National Health and Nutrition Examination Survey Feb 2001. J Am Geriatr Soc Jan. 2007;55(1):108-13.
Battino M, Bompadre S, Politi A, Fioroni M, Rubini C, Bullon P. Antioxidant status (CoQ10 and Vit. E levels) and immunohistochemical analysis of soft tissues in periodontal diseases. Biofactors 2005;25(1-4):213-7.
Guerrero RF, García-Parrilla MC, Puertas B, Cantos-Villar E. Wine, resveratrol and health: a review. Nat Prod Commun. May 2009;4(5):635-58.
ElAttar TM, Virji AS. Modulating effect of resveratrol and quercetin on oral cancer cell growth and proliferation. Anticancer Drugs Feb. 1999;10(2):187-93.
Rezk BM, Haenen GR, van der Vijgh WJ, Bast A. The antioxidant activity of phloretin: the disclosure of a new antioxidant pharmacophore in flavonoids. Biochem Biophys Res Commun Jul. 5, 2002;295(1):9-13.
Valenta C, Cladera J, O'Shea P, Hadgraft J. Effect of phloretin on the percutaneous absorption of lignocaine across human skin. J Pharm Sci. Apr. 2001;90(4):485-92.
Bonté F, Noel-Hudson MS, Wepierre J, Meybeck A Protective effect of curcuminoids on epidermal skin cells under free oxygen radical stress. Planta Med. Jun. 1997;63(3):265-6.
Phan TT, See P, Lee ST, Chan SY. Protective effects of curcumin against oxidative damage on skin cells in vitro: its implication for wound healing. J Trauma. Nov. 2001;51(5):927-31.
Nakamura Y, Ohto Y, Murakami A, Osawa T, Ohigashi H. Inhibitory effects of curcumin and tetrahydrocurcuminoids on the tumor promoter-induced reactive oxygen species generation in leukocytes in vitro and in vivo. Jpn J Cancer Res. Apr. 1998;89(4):361-70.
Holder GM, Plummer JL, Ryan AJ. The metabolism and excretion of curcumin (1,7-bis-(4-hydroxy-3-methoxyphenyl)-1,6-heptadiene-3,5-dione) in the rat. Xenobiotica Dec. 1978;8(12):761-8.
Osawa T, Sugiyama Y, Inayoshi M, Kawakishi S. Antioxidative activity of tetrahydrocurcuminoids . Biosci Biotechnol Biochem. Sep. 1985;59(9):1609-12.
Pan et al., "Reactivity of Ferulic Acid and Its Derivatives toward Hydrogen Peroxide and Peracetic Acid", J Agric Food Chem. Aug. 1999;47(8):3325-31.
Oresajo et al.; "A multicenter, controlled clinical study to evaluate the efficacy and tolerance of an antioxidant composition containing vitamin C, ferulic acid, and phloretin on photodamaged skin"; J Am Acad Dermatol; pp. 1, 2009.
Oresajo et al.; "Effect of a topical antioxidant composition containing vitamin C, ferulic acid, and phloretin in protecting human skin from ultraviolet light-induced skin damage and oxidative stress"; J Am Acad Dermatol; pp. 1, 2009.
Oresajo et al.; "Protective effects of a topical antioxidant mixture containing vitamin C, ferulic acid, and phloretin against ultraviolet-induced photodamage in human skin"; Joural of Cosmetic Dermatology; vol. 7; pp. 290-297, 2008.
San Miguel et al.; "Antioxidants counteract nicotine and promote migration via RacGTP in Oral Fibroblast Cells"; J Periodontol; pp. 1675-1690, 2010.
Zhang et al.; "A comparison of skin delivery of ferulic acid and its derivatives: Evaluation of their efficacy and safety"; International Journal of Pharmaceutics; vol. 399; pp. 44-51, 2010.
Dahl et al.; "Clinical evaluation of antioxidant gel cream containing vitamin C, ferulic acid, and phloretin on photodamaged skin"; J Am Acad Dermatol; pp. 1, 2011.
Ohkawa et al., "Assay for lipid peroxides in animal tissues by thiobarbituric acid reaction," Analytical Biochemistry, vol. 95, No. 2, pp. 351-358, 1979.
A. Gupta et al., "Lipid peroxidation and antioxidant status in head and neck squamous cell carcinoma patients", Oxidative Medicine and Cellular Longevity, vol. 2, Issue 2, pp. 68-72, Apr.-Jun. 2009.
G. Bahar et al., "Salivary Analysis in Oral Cancer Patients: DNA and protein oxidation, reactive nitrogen species, and antioxidant profile", Cancer, vol. 109, Issue 1, p. 54-59, Jun. 2007.
D. Rodriguez de Sotillo et al., "Evidence of Oxidative Stress in Temporomandibular Disorders: A Plot Study", Journal of Oral Rehabilitation, vol. 39, No. 10, pp. 722-728, Apr. 2011.
K. Ruchi et al., "Antioxidant activity in children with ADHD—a comparison in untreated and treated subjects with normal children", International Medical Journal Malasica, vol. 10, No. 1, pp. 31-35, Jun. 2011.
D. Miricescu et al., "The Antioxidant Potential of Saliva: Clinical Significance in Oral Disease", Therapeutics, Pharmacology and Clincial Toxicology, vol. 15, No. 2, pp. 139-143, Jun. 2011.
International Search Report and Written Opinion; PCT/US2009/065318; pp. 13, May 7, 2010.
Danish State of the Art Search; Application No. SE 2008 02591; pp. 10, Aug. 26, 2008.
Danish State of the Art Search; Application No. SE 2008 02591; pp. 9, Aug. 27, 2008.
Appeal under 35 U.S.C. § 134; U.S. Appl. No. 09/871,318; pp. 12, Aug. 27, 2008.
American Dental Association, "Researchers concluded that glutathione might be beneficial when used as a supplement to help prevent chronic periodontitis and might be able to assist in the healing process." JADA, vol. 134, Jan. 2003; pp. 20-24.
Pinnell et al.; "Topical L-Ascorbic Acid: Percutaneous Absorption Studies", Dermatol Surg. 2001; 27:137-142, Feb. 2001.
Touger-Decker and Van Loveren; "Sugars and Dental Carriers", Am. J. Clin. Nutr.; Oct. 2003, vol. 78, No. 4:881S-892S.
Shannon et la., "Phenotypic differences between oral and tkin fibroblasts in wound contraction and growth factor expression", Wound Repair and Regeneration; Mar.-Apr. 2006, vol. 14, No. 2:172-178.
Bay et al., "Response of human oral mucosa and skin t2 histamine provocation: laser Doppler perfusion imaging discloses differences in the nociceptive nervouse system", Acta Odontologica Scandinavica, 2009; 64; p. 99-105.
McKeown et al., "Matrix Matalloproteinase-3 Differences in Oral and Skin Fibroblasts", Journal of Dental Research, 86(5), pp. 456-462, May 1, 2007.

\* cited by examiner

ANTIOXIDANT COMPOSITIONS FOR TREATMENT OF INFLAMMATION OR OXIDATIVE DAMAGE

RELATED APPLICATIONS

This application is a U.S. National Stage Application of International Application No. PCT/US2012/057824 filed Sep. 28, 2012, which claims the benefit under 35 U.S.C. §119(e) of U.S. Provisional Application Ser. No. 61/541,500 filed Sep. 30, 2011, U.S. Provisional Application Ser. No. 61/562,262 filed Nov. 21, 2011, U.S. Provisional Application Ser. No. 61/646,648 filed May 14, 2012, and U.S. Provisional Application Ser. No. 61/679,884 filed Aug. 6, 2012. The contents of which are incorporated herein in its entirety by this reference.

TECHNICAL FIELD

The current invention, according to some embodiments, relates to methods of using antioxidant compositions to prevent, reduce, or eliminate the negative effects of oxidative damage or inflammation. In particular embodiments, the antioxidant compositions may be used with soft oral tissues, such as the lips, oral mucosa, tongue, soft and hard palates, periodontal ligament, or gingiva. The current invention, according to other embodiments, also relates to methods of treating or preventing one or more diseases or inflammation of such tissues.

BACKGROUND

Oxidative damage of soft oral tissues may be caused by dental devices in a number of ways. In some situations, this can occur as materials leech out of dental devices and directly cause oxidative damage. Damage can also take place if materials associated with a dental device participate in other reactions that cause or increase oxidative damage, for instance by creating free radicals or other reactive species. Free radicals may also be released by dental devices or produced in the mouth as a result of dental devices, and these are often the cause of oxidative damage to the body. Free radicals and other reactive species are also known to cause oxidative damage to organisms. As this oxidative damage occurs, it may result in inflammation, periodontal disease, and related problems, such as cardiovascular disease or increased susceptibility to formation of cancerous lesions in the mouth.

Periodontal disease often begins with oxidative damage to a few oral cells. The body recognizes and tries to clear away these damaged cells in part through the actions of inflammation pathways. Inflammatory pathways, however, are typically not able to only clean up the damaged cells. Other, healthy cells are damaged in the process, often causing much more harm than the original oxidative damage.

The inflammatory response is triggered by some injurious stimuli such as pathogens, damaged cells, or irritants. In a typical inflammation response, a cascade of biochemical events propagates and matures the inflammation response. Circulating peripheral blood mononuclear cells (PBMCs) such as Leukocytes are important cells in these biochemical cascades. These cells express a range of pathogen-recognition receptors (PRRs) which recognize highly conserved pathogen-associated molecular patterns (PAMPs) present with bacteria, viruses, fungi, mycoplasma, and parasitic protozoa. The largest family of PRRs are the Toll-like receptors (TLRs), the most well-known being TLR4 which is capable of ligating the lipopolysaccharide (LPS) present in the cell wall of many Gram-negative bacteria such as *Escherischia coli* (*E. coli*) and *Actinobacillus actinomycetemcomitans* (Aa). TLR4 is highly expressed by monocytes, marcophages, and neutrophils. The ligation of LPS results in a gene expression program that results in the induction of local inflammation.

Several biochemical molecules may be involved with inflammation or an immune response, and a number of examples follow. Tumor necrosis factor-alpha (TNF-α) is a cytokine involved in systemic inflammation and is used in the initiation of inflammation. C—X—C motif chemokine 5 (CXCL5) is produce during inflammation to stimulates chemotaxis of neutrophils possessing angiogenic properties. Interleukin 8 (IL-8) is a chemokine that is a chemoattractant for certain inflammatory molecules and induces chemotaxis in its target cells. Interleukin 4 (IL-4) induces differentiation of naïve helper T cells to Th2 cells and the stimulation of B-cells. Interleukin 2 (IL-2) is a cytokine that attracts lymphocytes or leukocytes. Interleukin-1 alpha (IL-1α) and Interleukin-1 beta (IL-1β) are cytokines involved in the initial production of inflammation. Granulocyte colony-stimulating factor (G-CSF) is a cytokine that stimulates the bone marrow to produce granulocytes. Granulocyte macrophage colony-stimulating factor (GM-CSF) is a cytokine that stimulates stem cells to produce granulocytes and monocytes. Interferon-gamma (IFN-γ) is a cytokine that increase lysosome activity of macrophages and promotes leukocyte migration. Interleukin 6 (IL-6) is a cytokine involved in acute phase protein synthesis and the production of neutrophils in the bone marrow. Interleukin 10 (IL-10) is an anti-inflammatory cytokine. Interleukin 5 (IL-5) is a cytokine involved with B cell growth and eosinophil granulocyte activation. Interleukin 17 (IL-17) is a cytokine involved in recruiting monocytes and neutrophils to the site of inflammation. Vascular endothelial growth factor (VEGF) is a signal protein involved in vasculogensis. Monocyte chemotactic protein-1 (MCP-1) or chemokine (C-C motif) ligand 2 (CCL2) is involved with recruiting monocytes and other cells to the site of inflammation. Chemokine (C-C motif) ligand 5 (CCL5) is a protein involved in recruiting leukocytes to the site of inflammation and the activation of certain natural-killer (NK) cells. Macrophage inflammatory proteins 1-alpha and beta (MIP-1α and MIP-1β, also known as chemokine (C-C) motif ligand 3 and 4 (CCL3 and CCL4 respectively) are chemokines released by macrophages which activate granulocytes and induce the synthesis and release of other pro-inflammatory cytokines. Interleukin 1 receptor antagonist (IL-1RA) is a protein that binds to the IL-1 receptor, preventing IL-1 from signaling that cell, thus inhibiting inflammation. Thrombopoietin is a glycoprotein that regulates the production of platelets by the bone marrow. Nuclear factor kappa-light-chain-enhancer of activated B cells (NF-κB) is a protein complex that plays a key role in regulating the immune response to infection, particularly by controlling many genes involved. IκB-α is a protein that functions to inhibit the NF-κB transcription factor.

Current treatments for periodontal disease involve surgery in the local area or antibiotics if the periodontal disease has progressed far enough to allow infection to set in. These treatments do not address the underlying systemic nature of periodontal disease and instead merely address very specific and local problems. Further, they have limited or no ability to cause regrowth and healing of the diseased tissue. Other problems resulting from oxidative damage of soft oral tissues similarly do not have effective treatments. Accordingly, a need exists for effective methods to treat periodontal disease and other soft oral tissue diseases resulting from oxidative damage or to prevent such disease or damage all together.

Antioxidants are known to protect organisms, such as humans, from oxidative damage, but their effective administration is a problem. For example, antioxidants ingested in food or as a pill have a limited effect on periodontal disease because the uptake and management of antioxidants is tightly regulated by body mechanisms such that antioxidants are distributed to all body parts, resulting in only a minimal portion of the ingested amount reaching the soft oral tissues and thus limiting the antioxidant effect in that tissue. Similarly, previous antioxidant compositions have been developed for use in specific areas, such as the skin, but these compositions are not suitable for use on soft oral tissue due to the many differences between skin and soft oral tissue. For example, commonly used skin antioxidant compositions are formulated at a pH far too low for use in the oral environment, and will demineralize tooth enamel. There are other issues of compatibility with formulations intended for use on the skin, which frequently contain oils, lipids and detergents that are inappropriate or ineffective in the moist environment of the mouth.

Accordingly, a need exists for antioxidant compositions able to topically treat or prevent soft oral tissue diseases resulting from oxidative damage caused by dental devices.

SUMMARY

The current invention, according to some embodiments, relates to methods of using antioxidant compositions to prevent, reduce, or eliminate the negative effects of oxidative damage or inflammation.

One embodiment of the invention is directed to a method of preventing, reducing, or eliminating at least one negative effect of inflammation. The method may include applying to a soft oral tissue in the patient an antioxidant composition. The antioxidant composition may include between 0.0001% and 5.0% w/w or at least one antioxidant, wherein the at least one antioxidant includes a natural phytochemcial antioxidant, a flavonoid, an anthocyanidin, a dihydrochalcone, a phenylpropanoid, a chalcone, a curcuminoid, a tannin, a stilbenoid, a coumarin, a carotenoid, or a vitamin, and an orally pharmaceutically acceptable carrier. The pH of the oral antioxidant composition may be at least 5.0.

One embodiment of the invention is directed to a method of preventing, reducing, or eliminating at least one negative effects of oxidative damage, such as an oral disease, particularly oxidative damage caused by a dental device in the mouth of a patient. The method may include applying topically to a soft oral tissue in the patient an oral antioxidant composition. The antioxidant composition may include between 0.0001% and 5.0% w/w or at least one antioxidant, wherein the at least one antioxidant includes a natural phytochemcial antioxidant, a flavonoid, an anthocyanidin, a dihydrochalcone, a phenylpropanoid, a chalcone, a curcuminoid, a tannin, a stilbenoid, a coumarin, a carotenoid, or a vitamin, and an orally pharmaceutically acceptable carrier. The pH of the oral antioxidant composition may be at least 5.0.

BRIEF DESCRIPTION OF THE DRAWINGS

Embodiments of the present invention may be better understood through reference to the following figures in which.

DETAILED DESCRIPTION

Figure 1:
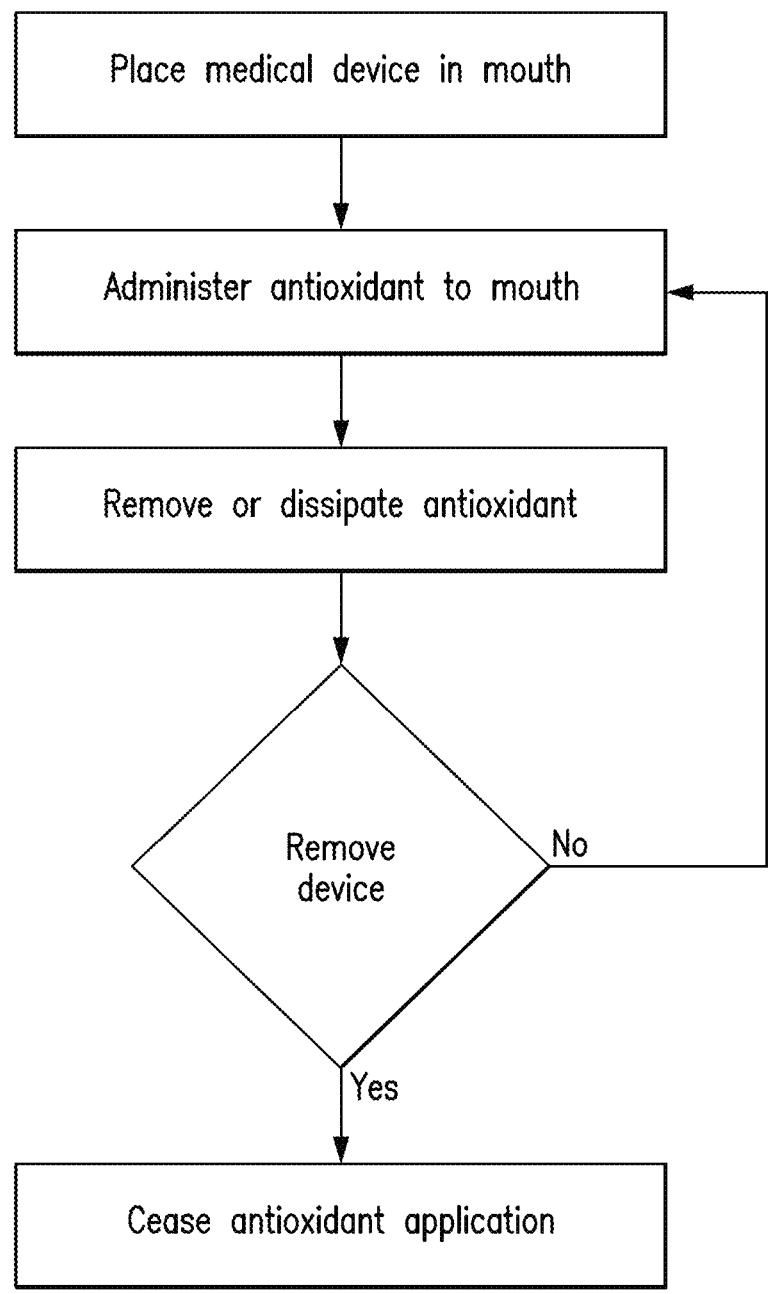
FIG. 1 shows an administration method in which an antioxidant is provided concurrently and/or recurrently with a dental device, according to an embodiment of the current disclosure.
Figure 2:
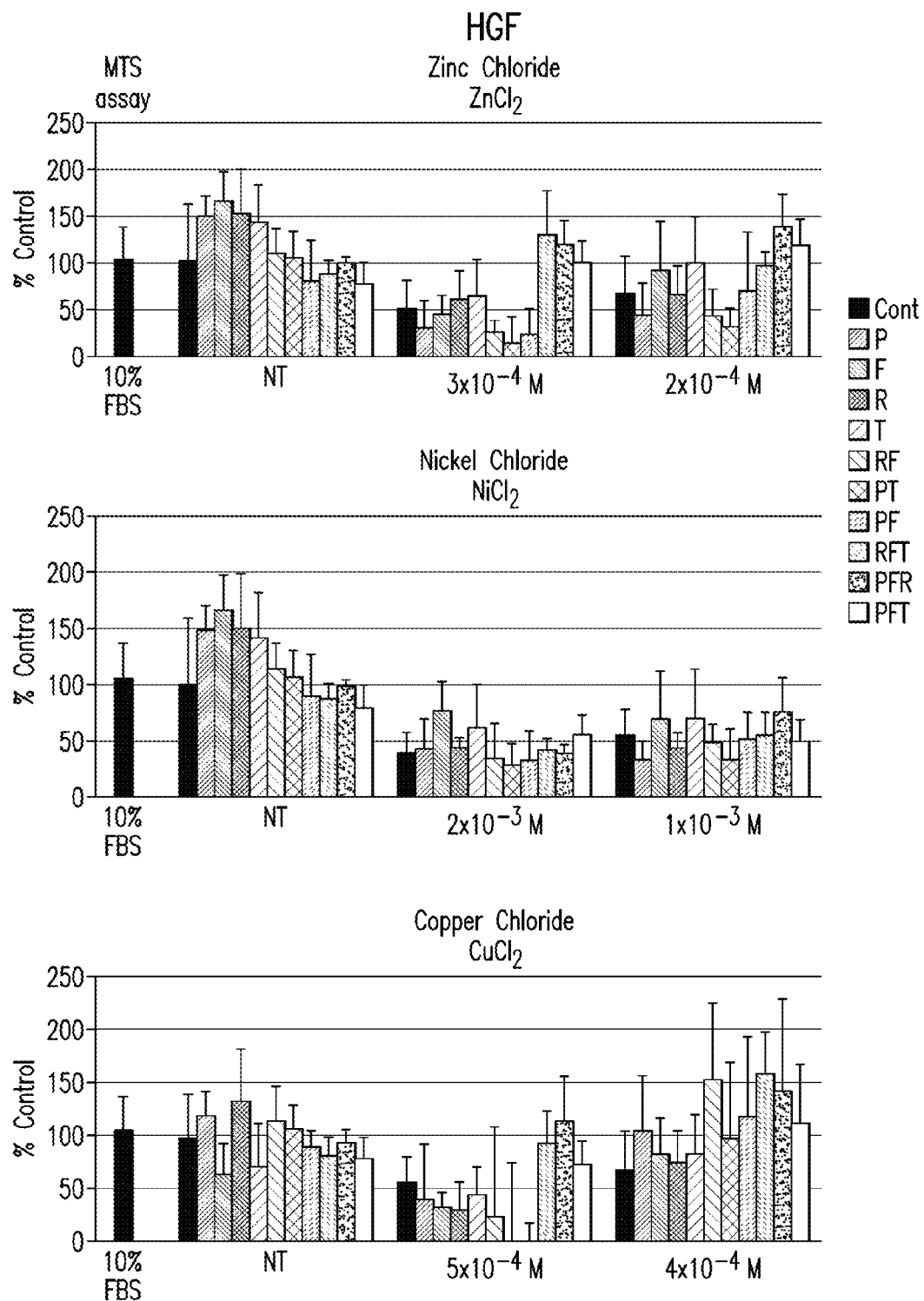
FIG. 2 shows results from an MTS assay of human gingival fibroblasts being treated with antioxidants.
Figure 3:
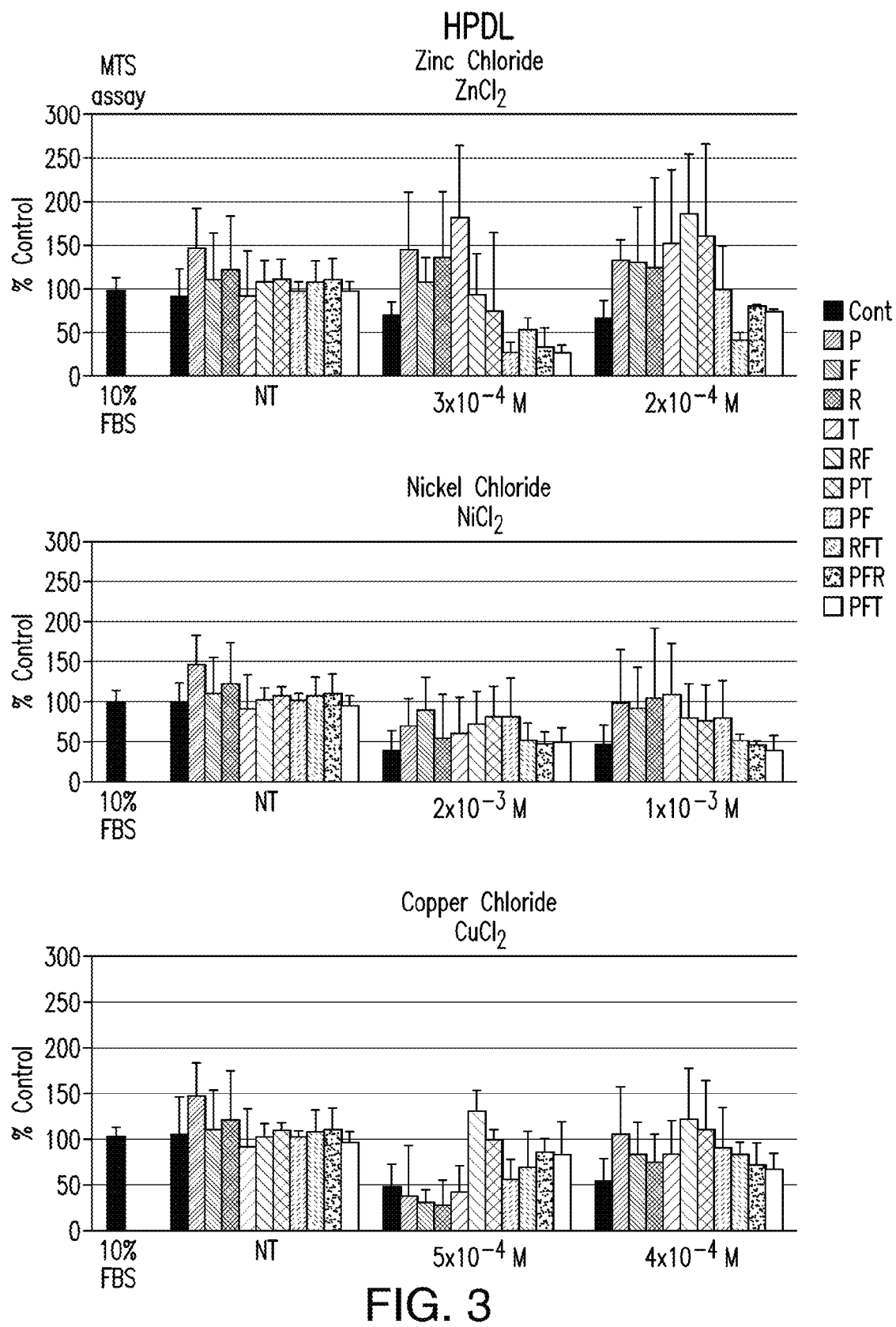
FIG. 3 shows results from an MTS assay of human periodontal ligament fibroblasts being treated with antioxidants.
Figure 4:
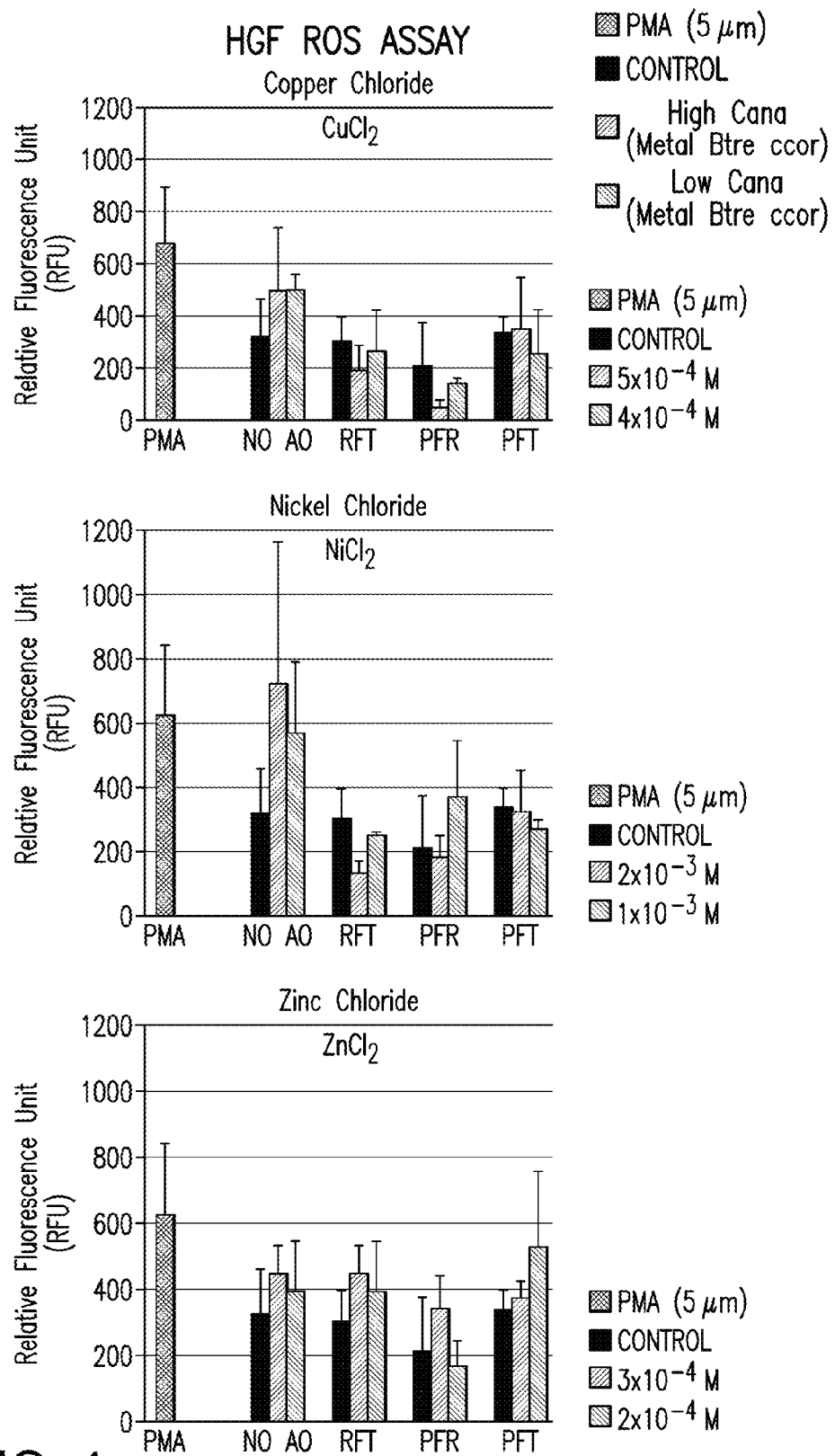
FIG. 4 shows results from an ROS assay of human gingival fibroblasts being treated with antioxidants.
Figure 5:
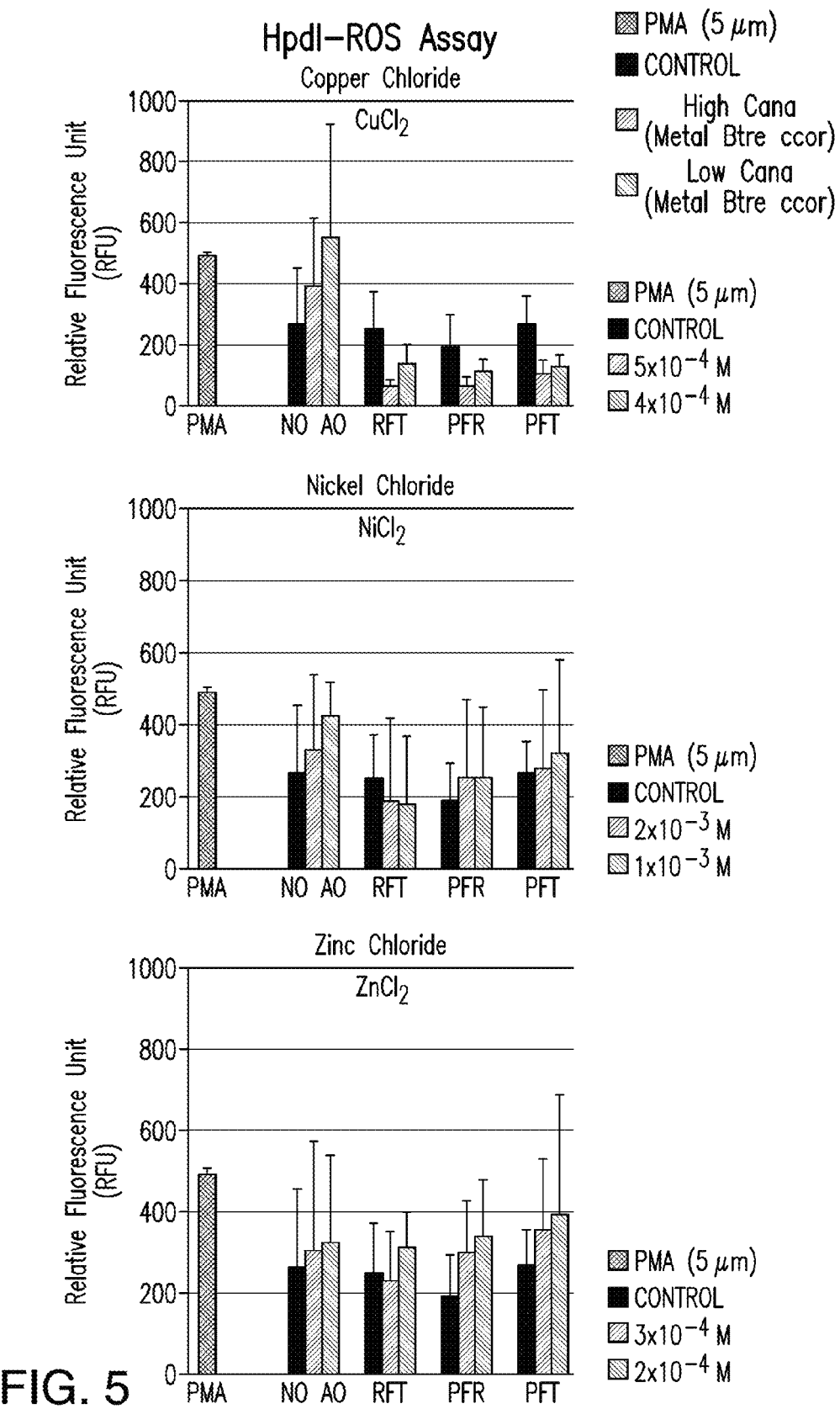
FIG. 5 shows results from an ROS assay of human periodontal ligament fibroblasts being treated with antioxidants.
Figure 6:
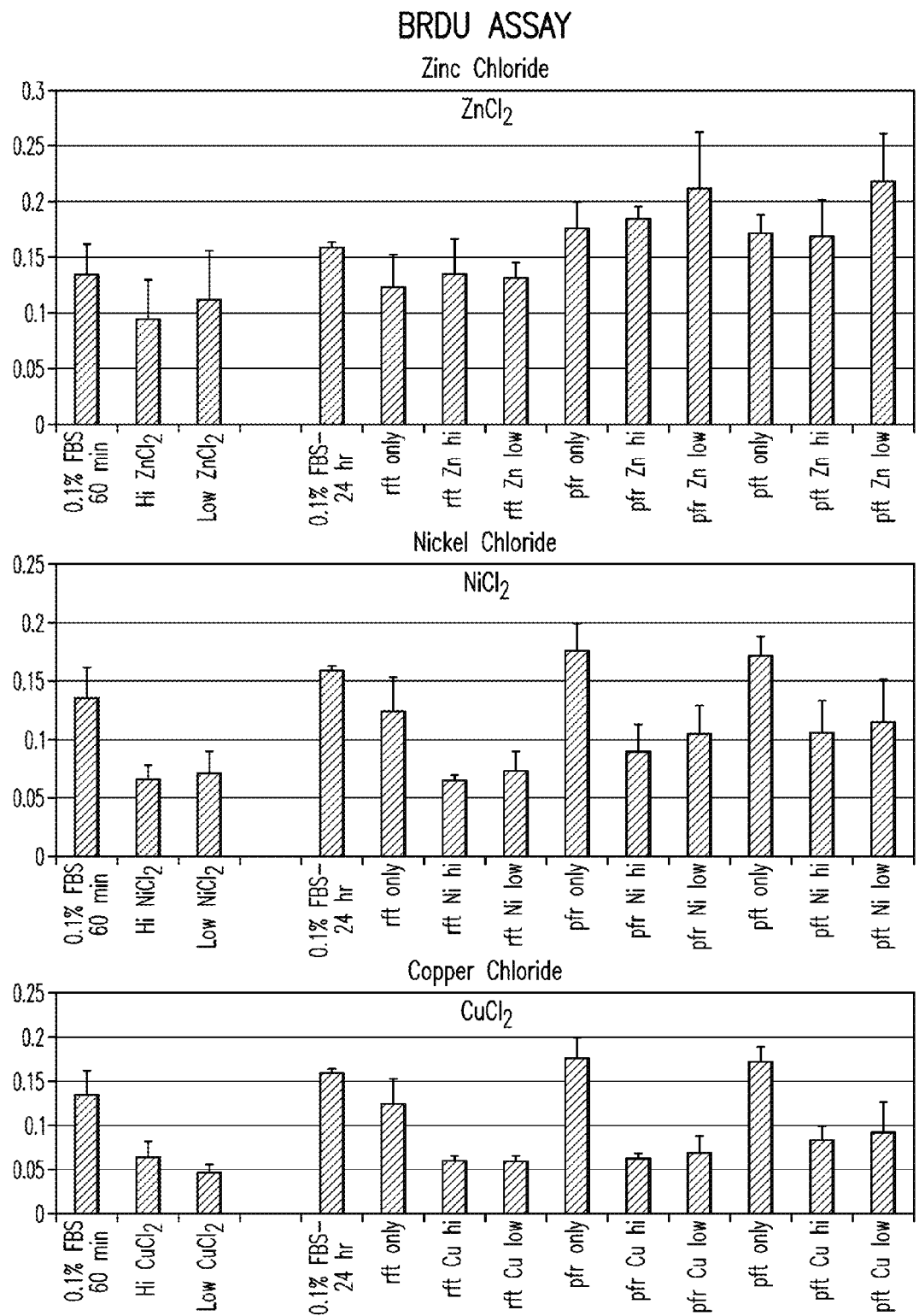
FIG. 6 shows results from a BrdU assay of cells after treatment with antioxidants.

The current invention, according to some embodiments, relates to methods of using antioxidant compositions in combination with dental devices to prevent, reduce, or eliminate the negative effects of oxidative damage associated with such devices. The current invention, according to other embodiments, relates to methods of using antioxidant compositions to prevent, reduce, or eliminate the negative effects of inflammation. Although oxidative damage an inflammation are often discussed separately herein, it will be understood by one of skill in the art that in some instances they may occur simultaneously. For example, a dental device may cause both oxidative damage and inflammation.

Discussed herein are various antioxidants that are components of the antioxidant compositions used in the invention. Although some derivatives of these antioxidants are identified specifically herein, this is not intended to in any way exclude other derivatives of these antioxidants from the scope of the invention. According to embodiments of the invention, any derivatives of the antioxidants discussed herein that also have antioxidant properties may be substituted for the named antioxidant unless it is clear from context that such substitution is not intended. Further, antioxidants as discussed herein may, unless otherwise clear from context, include combinations of the named antioxidant and derivatives or combinations of derivatives alone. Similarly, when groups of antioxidants are discussed, combinations of group members may be used unless otherwise indicated by context.

Dental Devices

Dental devices may include any object inserted temporarily, permanently, or semi-permanently into the mouth. Although temporarily-inserted devices may cause oxidative damage and are not excluded from this disclosure, certain embodiments relate to oxidative damage caused by permanent or semi-permanent devices. Permanent and semi-permanent dental devices may include orthodontic devices such as braces, retainers, and guards designed to prevent nighttime teeth grinding. Permanent and semi-permanent dental devices may also include prosthetic devices intended to replace natural teeth such as bridges, dentures, and implants. Permanent and semi-permanent dental devices may further include restorative or preventative devices such as coatings, sealants, crowns, caps, and fillings. Permanent and semi-permanent dental devices may further include cosmetic devices or devices designed to treat non-dental problems, such as veneers, grills, piercings, athletic mouth-guards, and anti-snoring devices.

Dental devices may contain one or more of a number of materials that may cause oxidative damage to soft oral tissues. In particular embodiments, the oxidative damage may be caused by dental resins or ceramics, such as acrylic resins, acetal resins, heat-polymerized resins, and autopolymerized resins, polymerized resin cements, methacrylate resins, including methyl methacrylate resins, orthodontic adhesives, highly filled composites, bariumaluminiumsilica, bariumaluminiumfluorosilica, and organically modified ceramics. These materials may release harmful substances such as benzalkonium chloride, urethane acrylate oligomers, bisphenol A glycidyl methacrylate (Bis-GMA), triethylene glycol dimethacrylate (TEGDMA), urethane dimethacrylate (UDMA), and bisphenol A (BPA).

In other particular embodiments, the oxidative damage may be caused by metals in dental devices. For example, metals that may cause oxidative damage include Nickel (Ni), Silver (Ag), Copper (Cu), Palladium (Pd), Gold (Au), Chromium (Cr), Gallium (Ga), Titanium (Ti), Mercury (Hg), Platinum (Pt), Zinc (Zn), Molybdenum (Mo), Beryllium (Be), Iron (Fe), including stainless steel, Aluminum (Al), Iridium (Ir), Ruthenium (Ru), Rhodium (Rh), Vanadium (V) and Potassium (K). These metals may be present in elemental form or as part of an alloy. The use of metals in dental devices is described in further detail in D. A. Givan, "Precious Metals in Dentistry," *Dent. Clin, N. Am.* 51: 591-601 (2007), incorporated in material part by reference herein. The metals in some dental devices may release elemental metal or metal ions.

Oxidative damage to soft oral tissues may result from release of materials from a dental device. The released materials may directly cause oxidative damage or may take place in other reactions that cause or increase oxidative damage, for instance by creating reactive oxygen species (ROS). Nickel (Ni) may be particularly prone to release from a dental device under oral conditions. In general, release of materials may be pH-controlled and may occur at normal mouth pH, or at different mouth pHs such as those due to ingestion of food or beverages or the presence of other materials, such as tobacco or chewing gum, in the mouth. Release of materials may also be due to or increased by mechanical activities in the mouth, such as chewing or the use of a toothbrush or dental floss. The tendency of a dental device to release materials may also relate to the configuration of the device. In general, devices may release more materials from their surface than from interior areas. Accordingly, the surface area of a material-releasing component may affect the ability of a device to cause oxidative damage.

Effects of Oxidative Damage

Oxidative damage to soft oral tissues may cause a number of harmful effects. For example it may exert a cytotoxic effect, in some instances by eliciting an apoptotic response. As another example, it may interfere with cell motility. As still another example, oxidative damage may cause harmful mutations in a cell which may result in dysplasia. These and other cellular-level effects may also give rise to harmful tissue level effects, such as defects in wound healing and the formation of lesions. The exact effects may differ by oxidant and cell or tissue type. For example decreases in motility are more likely to be observed in cells that are normally motile, such as oral fibroblasts.

In certain embodiments, tissues harmed may include the lips, oral mucosa, tongue, soft and hard palates, periodontal ligament, or gingiva. Damaged cells may include gingival fibroblasts, periodontal ligament cells, osteoblasts and salivary gland cells/tissues. Cell damage may also eventually result in oral cancer, particularly as patients age, as described in Hershkovich, et al., "Age-Related Changes in Salivary Antioxidant Profile Possible Implications for Oral Cancer," *J. Gerontology* 62A(4):361-366 (2007), incorporated in material part by reference herein.

In some embodiments, particular diseases or indications may be treated. These diseases may be caused by oxidative damage, or some other cause. Oxidative damage may be associated with an indication of a disease. In addition, oxidative damage may prevent the complete resolution of a disease or indication. In some embodiments, xerostomia may be treated. In other indications, xerostomia may be associated with cancer. In other embodiments, mucositis may be treated. In others, bisphosphonate-related osteonecrosis of the jaw (BRONJ) may be treated.

Antioxidants

Antioxidant compositions used in conjunction with the invention may comprise single antioxidants or combinations of two or more antioxidants. According to some embodiments, combinations of multiple antioxidants may exhibit synergistic effects.

According to one embodiment, the antioxidants used may include natural exogenous phytochemical antioxidants such as phenolics and carotenoids.

According to another embodiment, the antioxidants used may include flavonoids. Flavonoids constitute a large group of over 5000 polyphenolic phytochemicals with antioxidant properties that act through direct free radicals scavenging. Flavonoids have anti-inflammatory, anti-bacterial, anti-viral, anti-allergic, anti-mutagenic, anti-thrombotic, anti-neoplastic and vasodilatory action and may prevent, reduce, or eliminate the oxidative damage from dental devices using these methods of action as well. Flavonoids also exhibit chelating properties with metal ions and may reduce the oxidative damage from metal ions by sequestering the ions. Formation and stability of flavonoids-metal-chelates is a structure-dependent function. Flavonoids with a catechol moiety and with hydrogen bonds between hydroxyl group in the 5- and 3-positions have chelating properties. Glycosides of flavonoids may also be used.

According to a more specific embodiment, the flavonoid may be a flavanone (derivative of 2,3-dihydro-2-phenylchromen-4-one). Flavones include: Butin, Eriodictyol, Hesperetin, Hesperidin, Homoeriodictyol, Isosakuranetin, Naringenin, Naringin, Pinocembrin, Poncirin, Sakuranetin, Sakuranin, and Sterubin.

According to another specific embodiment, the flavonoid may be a flavanonol (derivative of 3-hydroxy-2,3-dihydro-2-phenylchromen-4-one). Flavanols include: Taxifolin, Aromadedrin, Chrysandroside A, Chrysandroside B, Xeractinol, Astilbin, and Fustin.

According to another specific embodiment, the flavonoid may be a flavone (derivative of 2-phenylchromen-4-one). Flavones include: Apigenin, Luteolin, Tangeritin, Chrysin, Baicalein, Scutellarein, Wogonin, Synthetic Flavones: Diosmin, and Flavoxate.

According to another specific embodiment, the flavonoid may be a flavonol (derivative of 3-hydroxy-2-phenylchromen-4-one). Flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin.

According to another specific embodiment, the flavonoid may be a flavan-3-ol (derivatives of 2-phenyl-3,4-dihydro-2H-chromen-3-ol). Flavan-3-ols include: Catechin, Epicatechin, Epigallocatechin, Epicatechin gallate, Epigallocatechin gallate, Epiafzelechin, Fisetinidol, Guibourtinidol, Mesquitol, and Robinetinidol.

According to another specific embodiment, the flavonoid may be a flavan-4-ol (derivative of 2-phenylchroman-4-ol). Flavan-4-ols include: Apiforol and Luteoforol.

According to another specific embodiment, the flavonoid may be an isoflavone (derivative of 3-phenylchromen-4-one). Isoflavones include: Genistein, Daidzein, Biochanin A, Formononetin, and the Equol metabolite from Daidzein.

According to another embodiment, the antioxidant may be an anthocyanidin (derivative of 2-phenylchromenylium cation). Anthocyanidins include: Aurantinidin, Cyanidin, Delphinidin, Europinidin, Luteolinidin, Pelargonidin, Malvidin, Peonidin, Petunidin, Rosinidin, and Xanthone.

According to another embodiment, the antioxidant may be a Dihydrochalcone (derivative of 1,3-diphenyl-1-propanone). Dihydrochalcones include: Phloretin, Dihydrochalcone phloretin Phlorizin, Aspalathin, Naringin dihydrochalcone, Neohesperidin dihydrochalcone, and Nothofagin. Without limiting the mode of action of the invention, dihydrochalcones may exert an antioxidant effect by reducing reactive free radicals, like reactive oxygen and reactive nitrogen species.

According to another embodiment, the antioxidant may be a Phenylpropanoid (derivatives of cinnamic acid). Phenylpropanoids include: Cinnamic acid, Caffeic acid, Ferulic acid, Trans-ferulic acid (including its antioxidant pharmacore 2,6-dihydroxyacetophenome), 5-Hydroxyferulic acid, Sinapic acid, Coumaryl alcohol, Coniferyl alcohol, Sinapyl alcohol, Eugenol, Chavicol, Safrole, P-coumaric acid, and Sinapinic acid. Without limiting the mode of action of the invention, Phenylpropanoids may neutralize free radicals.

According to another embodiment, the antioxidant may be a Chalcone (derivative of 1,3-diphenyl-2-propen-1-one). Chalcones include: Butein, Okanin, Carthamin, Marein, Sophoradin, Xanthohumol, Flavokvain A, Flavokavain B, Flavokavin C., and synthetic Safalcone.

According to another embodiment, the antioxidant may be a Curcuminoid. Curcuminoids include: Curcumin, Desmethoxycurcumin, bis-Desmethoxycurcumin, Tetrahydrocurcumin, and Tetrahydrocurcuminoids. Curcumin and tetrahydrocurcuminoids may be derived from rhizomes of *Curcuma longa*. Tetrahydrocurcumin, a metabolite of curcumin, has been found to be a more potent antioxidant and more stable compared to curcumin. Tetrahydrocurcumin is available commercially, for example, it is the main component of Tetrahydrocurcuminoids CG™ as sold by Sabinsa Corp. (Piscataway, N.J.). Tetrahydrocurcuminoids CG™ contains on a w/w basis tetrahydrocurcumin (75-90%), tetrahydrodemethoxycurcumin (15-20%), and tetrahydrobisdemethoxycurcumin (1-4%). Each of these components is a potent antioxidant. Accordingly, in some embodiments, curcumin or tetrahydrocurcumin may be used in place of tetrahydrocurcuminoids. Further, each component of Tetrahydrocurcuminoids CG™ may be used separately as tetrahydrocurcuminoids. Tetrahydrocurcuminoids CG™ or other useful tetrahydrocurcuminoids are described in WO 00/61162. Without limiting the mode of action of the invention, curcuminoids may reduce free radicals.

According to another embodiment, the antioxidant may be a Tannin. Tannins include: Tannin, Terflavin B, Glucogallin, Dgallic acid, and Quercitannic acid.

According to another embodiment, the antioxidant may be a stilbenoid. Stilbenoids include: Resveratrol, Pterostilbene, and Piceatannol. Resveratrol may include, but is not limited to, 3,5,4'-trihydroxystilbene, 3,4,3',5'-tetrahydroxystilbene (piceatannol), 2,3',4,5'-tetrahydroxystilbene (oxyresveratrol), 4,4'-dihydroxystilbene, and alpha and beta glucoside, galactoside and mannoside derivatives thereof. Other derivatives are recited in U.S. Pat. No. 6,572,882, incorporated by reference herein. Additionally, analogs of resveratrol such as the 3,4,4',5-tetrahydroxystilbene of U.S. Pat. No. 6,790,869 (incorporated by reference herein) may also be used. Both cis and trans configurations of resveratrol or its derivatives may be used. Without limiting the mode of action of the invention, stilbenoids may neutralize free radicals.

According to another embodiment, the antioxidant may be a Coumarin (derivatives of 2H-chromen-2-one). Coumarins include: 4-Hydroxycoumarin, Umbelliferone, Aesculetin, Herniarin, Auraptene, and Dicoumarol.

According to another embodiment, the antioxidant may be a Carotenoid. Carotenoids include: beta-Carotene, alpha-Carotene, gamma-Carotene, beta-Cryptoxanthin, Lycopene, Lutein, and Idebenone.

According to another embodiment, the antioxidant may be a vitamin. Vitamins include: Retinol, Ascorbic acid, L-Ascorbic acid, Tocopherol, Tocotrienol, and the Vitamin cofactor: Coenzyme Q10.

According to another embodiment, the antioxidant may be: a Xanthone, Butylated Hydroxytoluene, 2,6-Di-tert-butylphenol, 2,4-Dimethyl-6-tert-butylphenol, Gallic acid, Eugenol, Uric acid, alpha-Lipoic acid, Ellagic acid, Chicoric acid, Chlorogenic acid, Rosmarinic acid, Salicylic acid, Acetylcysteine, S-Allyl cysteine, Barbigerone, Chebulagic acid, Edaravone, Ethoxyquin, Glutathione, Hydroxytyrosol, Idebenone, Melatonin, N-Acetylserotonin, Nordihydroguaiaretic acid, Oleocanthal, Oleuropein, Paradol, Piceatannol, Probucol, Propyl gallate, Protocatechuic acid, Pyritinol, Rutin, Secoisolariciresinol diglucoside, Sesamin, Sesamol, Silibinin, Silymarin, Theaflavin, Theaflavin digallate, Thmoquinone, Trolox, Tyrosol, Polyunsaturated fatty acids, and sulfur-based antioxidants such as Methionine or Lipoic acid.

Antioxidants used herein may be synthesized, extracted or purified from natural products, or present in a natural product. The antioxidants may be isolated or partially isolated prior to formulation for use in the methods described herein or used in a naturally occurring form. In addition, the antioxidants may include plant extracts or combinations containing any of the above mentioned antioxidants or derivatives thereof.

According to particular embodiments, the concentration of each individual antioxidant in the antioxidant compositions may be above 0.0001% w/w, above 0.001% w/w, above 0.01% w/w, as high as 0.5% w/w, 1.0%, w/w, 1.5% w/w, 2% w/w, 3% w/w, 4% w/w, 5%, w/w and in ranges between any combinations of these concentration limits. Expressed another way, the molarity of each antioxidant may be on the order of $10^{-3}$ M or less, $10^{-4}$ M or less, $10^{-5}$ M or less, or $10^{-6}$ M or less. Antioxidant concentrations in antioxidant compositions of the invention may be higher than concentrations tested in cell culture due to dilution of the antioxidant in actual use where it is likely combined with saliva and due to shorter exposure times of the actual soft oral tissue as compared to cell culture conditions due to swallowing or other removal of the antioxidant composition.

According to a particular embodiment, the total antioxidant concentration of all antioxidants in an antioxidant composition may be above 0.0001% w/w, above 0.001% w/w, above 0.01% w/w, as high as 0.5% w/w, 1.0%, w/w, 1.5% w/w, 2% w/w, 3% w/w, 5%, w/w, 10% w/w, 15% w/w, or 20% w/w and in ranges between any combinations of these concentration limits.

The concentration of various antioxidant components may be determined by the amount that achieves a desired effect, such as a cell proliferation effect, increased migration of a cell, or decreased cell death, in a soft oral tissue. For some combinations, upper limits on the concentration of the antioxidant components may apply due to decreases in desired effects at high antioxidant concentrations. In other embodiments, upper limits of antioxidant concentration may be set by acceptable levels to avoid gingival hyperplasia.

For antioxidant compositions containing mixtures of antioxidants, the ratios of one antioxidant to another may be mole per mole 1:1. In other embodiments, the ratios may be adjusted depending on the particular antioxidant compositions used. For example, one antioxidant composition may be in the majority and the other may be in the minority due to various factors including differential therapeutic or preventative effects, differential adverse effects, ease of formulation, or cost. Each antioxidant may be present in sufficient amount to cause some improvement in the therapeutic or preventative effects of the antioxidant composition as compared to an identical composition lacking that antioxidant. In alternative embodiments, antioxidants may be present in at least a minimal amount to cause another desirable effect, such as stabilization of another antioxidant. Other antioxidants may be absent from such compositions or present only in trace amounts, such as a by-product, unable to cause any substantial therapeutic or preventative effect.

In certain embodiments, synergistic effects may be observed between two or more antioxidants. Many such synergistic effects are observed in the Examples contained herein. Antioxidants exhibiting synergistic effects may allow for improved results as compared to using the antioxidants alone in a given amount. They may allow for the same results to be obtained as with the antioxidants alone, but using lower amounts of one or more of the antioxidants. Synergistic antioxidants may also allow a combination of these two effects, for example by administering a lower amount of one or more of the antioxidants, while still obtaining improved effects as compared to using the antioxidants alone. In selected embodiments, the amount of an antioxidant exhibiting a synergistic effect in an antioxidant composition may be only 25%, only 50%, or only 75% the amount otherwise described herein for use in such a composition. Among a group of antioxidants exhibiting a synergistic effect, the amount of only one, more than one, or all antioxidants in the group may be reduced. Furthermore, in embodiments in which one antioxidant of a group induces a synergistic effect at very low amounts, that antioxidant may be included only in the minimal amount able to cause a measurable synergistic effect.

Antioxidant Compositions

Antioxidants as described above may be formulated for topical oral use. Topical oral use includes application topically to any soft oral tissue, including, but not limited to, the lips, oral mucosa, gingiva, tongue, other oral epithelium, including, but not limited to, the oral epithelium, oral sulcular epithelium and junctional epithelium, periodontal ligament, soft palate, hard palate, and the like. Topical application may, in some embodiments, provide the antioxidants to both the oral epithelium and underlying tissues such as the periodontal ligament, lamina propria and submucosal layers, including mesenchymal and periodontal ligament cells, and gingival fibroblasts. Formulations suitable for oral use include, but are not limited to, pastes, gels, rinses, sprays, including aerosol sprays, syrups, powders, including reconstitutable powders, tablets, gums, lipsticks or balms, lozenges, dental trays or other teeth whitening delivery methods, pharmaceutical delivery vehicles such as liposomes, nano-particles, polymer-based delivery systems, and other cellular delivery vectors, particularly vehicles able to penetrate the oral epithelium, and in dissolvable strips. Example dissolvable strips and edible films in which the antioxidant composition may be incorporated are described in U.S. Pat. No. 6,923,981, incorporated by reference herein.

According to a particular embodiment, the antioxidant may be formulated in a topical composition that remains in the mouth for some time. For example, the topical composition may remain in the mouth for at least 5 minutes, at least 10 minutes, at least 15 minutes, at least 30 minutes, at least 45 minutes, or at least 60 minutes.

In some embodiments, the topical composition may be included in a medical device. For example, the topical composition may be included in some dental devices. In other embodiments, it may be applied to a dental device prior to use of that device. In still other embodiments, the topical composition may form a medical device after application in the mouth. For example, the topical composition may polyermize or solidify in the mouth. In certain embodiments, the topical composition may polymerize or solidify to form a protective barrier to protect an oral wound or to prevent physical irritation by another dental device, such as braces.

In some embodiments, the composition may be a non-topical composition. For instance, it may be injectable, particularly into the gums or other oral tissue. In one particular embodiment, the composition may be injectable deep into the sulcus, for instance in patients with severe periodontitis who may have pocket depths over 6 mm. In other non-topical embodiments, the composition maybe formulated for application to the surface of dental devices prior to use. For instance, it may be formulated for application to an implant before implantation.

Antioxidant compositions may be applied regularly, for example at least every 4 hours, every 12 hours, 24 hours, 48 hours, 72 hours, or 96 hours, or following each exposure to oxidative agents. Time between applications may vary depending on the antioxidant or antioxidant combinations used, but may be approximately the duration for which the composition causes a desirable effect, such as a cell proliferation effect, increased migration of a cell, or decreased cell death, in a soft oral tissue to which the composition is applied. Antioxidant compositions may be administered repeatedly, for example until the a disease, wound, or irritation shows sufficient improvement, or on a regularly occurring basis, for example, with permanent or semi-permanent dental devices. In some embodiments, the antioxidant composition may be applied after exposure to an agent able to cause oxidative damage in addition to that caused by the dental device. For example, it may be applied after tobacco, alcohol, or hydrogen peroxide use. Antioxidant compositions may be administered after exposure to temporary dental devices, such as after a dental cleaning Antioxidant compositions may also be administered on a prophylactic basis in the absence of any evidence of clinical symptoms.

The duration of administration may vary depending on the formulation of the antioxidant compositions. For example, the composition may be allowed to dissipate naturally, or it may be applied for a set period of time. For example, a more viscous formulation may be applied for a set time in a professional setting, such as after teeth cleaning.

The antioxidant compositions may preferably have a pH higher than skin antioxidant preparations. This provides the added benefit of avoiding lower pHs, which may damage enamel on the teeth. Example antioxidant compositions for oral use have a pH of 5.5, the normal lower limit of salivary pH, or higher. In some examples, the pH may be as high as 6.0 to further avoid demineralization of the teeth. Antioxidant compositions according to some embodiments may have a pH of up to around 7.4, the upper normal limit of salivary pH, or lower. Saliva is a buffer, so small quantities of materials, such as antioxidant compositions, introduced into the mouth may adjust to salivary pH or near salivary pH. Accordingly, some antioxidant compositions may have a pH near, but outside of salivary pH range. In some compositions, the upper pH limit may be set by the pH at which one of the antioxidants in the composition becomes predominantly its salt, typically around pH 8. According to one specific embodiment, antioxidant compositions may have a pH of between 5.5 and 7.4, similar to salivary pH. In another embodiment, the antioxidant composition may have a pH of between 5.5 and 8.0, between 5.5 and 7.0, between 5.5 and 6.5, between 5.5 and 6.0, between 6.0 and 8.0, between 6.0 and 7.0, or between 6.0 and 6.5.

Formulation

The antioxidant compositions of the invention may be formulated in any pharmaceutically acceptable carrier. For example, they may optionally further contain additional materials in some embodiments, such as solvents, surfactants, preservatives, viscosity enhancers, therapeutic additives, flavor or color enhancers, and water. These additional components, excluding water, may be in total up to 5%, 10%, 20%, 30%, 40%, or 50% w/w of the composition. Individually, additional components, excluding water, may be between 0.5% to 2% w/w of the composition or as much as 10% w/w or 20% w/w of the composition. Antioxidant compositions may be up to 95% water, up to 90% water, or between 50% and 90% water.

The antioxidant compositions of the invention may include various solvents. For example, they may include aqueous solvents, organic solvents, including non-aqueous organic solvents and aqueous organic solvents. In particular embodiments, propylene glycol, polyethylene glycol (PEG), such as PEG 600, glycerine, and ethyl alcohol may be used as solvents.

Buffers may be used to maintain pH of the composition. In a particular embodiment, a buffer may be used to maintain a pH of at least 5.0 or between 5.5 and 7.4. Buffers suitable for these pH ranges may include sodium citrate and citric acid buffer, which may be present in an amount of between 0.001% w/w to about 0.2% w/w.

Preservatives may be added to the antioxidant composition of the invention and include antibacterial compositions or any other preservative used in oral products. Exemplary preservatives include sodium bisulfite, sodium metabisulfite, phenoxyethanol, parabens such as methyl, ethyl, propyl, butyl or isobutyl parabens, 4-hydroxy benzoic acid, benzoic acid, sorbic acid, methyl salicylate, menthol, thymol, eucalyptol, xylitol, and the like.

Viscosity enhancers may be added to the antioxidant compositions of the invention and include any viscosity enhancers used in oral products. Specifically, gelling polymer is a viscosity enhancer and may include cellulose gum, such as carboxymethylcellulose (e.g. pre-hydrated Ticalose® CMC 2500), xanthan gum, gum arabic, guar gum, polyvinyl alcohol, sodium alginate, polyvinylpirrolidone, sodium hyaluronate, pullulen, carrageenans, and the like. Dextrans, dextran derivatives, or hyaluronic acid may be added to gelling polymers. Thickeners may also be selected to help dissolution of hydrophobic components or stabilize a gel structure. Exemplary thickeners include sugar alcohols such as sorbitol and xylitol, and the like.

Surfactants may be included if a hydrophobic antioxidant or other agent is present in the antioxidant composition. Suitable surfactants include ionic surfactants such as sodium lauryl sulfate, magnesium sodium lauryl sulfate, or tauranol; and non-ionic surfactants such as polyoxyethylene sorbitan esters, like Polysorbate 80, polyethylene-polypropylene glycols (particularly Poloxamer® 407), and the like. Other suitable surfactants may include cocamidopropyl betaine and plant saponins as natural surfactants.

Therapeutic additives may be added to the antioxidant compositions of the invention and include other drugs that increase or supplement the antioxidant effect or that are otherwise beneficial to soft oral tissues. For example, a fluoride source beneficial to the teeth may be added. Other wound healing agents, such as polysaccharides and aminopolysaccharides may also be added. Such agents may also help in forming gels, pastes and other formulations. Specific additives may include stannous fluoride, sodium fluoride, triclosan, sodium bicarbonate, chlorhexidine, or a HMG-CoA Reductase Inhibitor, such as a statin or a monocolin.

Flavor or color enhancers may be added to the antioxidant compositions of the invention and include any such materials used in oral cosmetic formulations or topical oral products. For example, flavors commonly used in toothpaste or lipstick or balm may be added. In embodiments where the antioxidant composition is contained in a lipstick or balm, a colorant may be added.

Other additional ingredients include, but are not limited to: potassium nitrate, sodium monofluorophosphate, sodium benzoate, sodium phosphate, aloe vera, lactoferrin, lysozyme, lactoperoxidase, glucose oxidase, mutanase, and dextranase.

Distilled or deionized water may be used to complete the antioxidant composition. Water may be present in much higher levels than other non-antioxidant components.

According to other embodiments, the antioxidant compositions may be in any pharmaceutically acceptable carrier formulated for oral use. Pharmaceutically acceptable carriers commonly include buffers such as citric acid and sodium citrate, and other organic acids, low-molecular weight polypeptides; proteins such as serum albumin, gelatin and immunoglobulin, hydrophilic polymers such as polyvinylpyrrolidone; amino acids such as glycine, glutamine, arginine or lysine; monosaccharides such as mannose, disaccharides, and other carbohydrates; chelating factors such as EDTA; metal ions such as zinc, cobalt or copper; sugar alcohols such as mannitol or sorbitol; and salt-forming counter ions such as sodium. Excipients and diluents may also be present and may include magnesium stearate, calcium carbonate, starch-gelatin paste, talc, aluminum salt, physiological salt solution, lactose, dextrose, sucrose, sorbitol, mannitol, calcium silicate, cellulose, methyl cellulose, amorphous cellulose, polyvinylpyrrolidine, methylhydroxy benzoate, and propylhydroxybezoate.

Certain additional components that are formulation-specific may also be added. For example, paste formulations may include one or more ingredients used in oral pastes, such as toothpaste. Examples ingredients include thickening agents such as methylcellulose, carboxymethylcellulose, such as pre-hydrated Ticalose® CMC 2500, or hydroxypropyl methylcellulose and humectants, gel carriers such as gelatin, polyethylene glycol, xanthan gum, gum arabic, and guar gum. In some embodiments, paste formulations may include an abrasive agent, such as silicas. In some embodiments, Zeodent® silicas produced by Hubert might be used, or any other silica as is known in the art.

According to some embodiments, the antioxidant compositions of the invention may consist essentially of one or more of the antioxidants and one or more of the above additional materials.

Other embodiments of the invention relate to products containing antioxidants. The products may contain concentrations of the antioxidants identified for antioxidant compositions above. Products may be sold containing these concentrations, or they may be made by adding antioxidants to achieve the above concentrations after sale. For example, one embodiment of the invention relates to antioxidant compositions intended for addition to other products to achieve the antioxidant concentrations described above. These concentrated antioxidant additives may have higher concentrations of antioxidants than described above to allow for their dilution when added to a product.

Example products that may constitute embodiments of the invention or to which concentrated antioxidant additives may be added include existing oral care products, including, but not limited to, pastes, gels, rinses, sprays, including aerosol sprays, syrups powders, including reconstitutable powders, tablets, gums, lipsticks or balms, lozenges, dental trays or other teeth whitening delivery methods, pharmaceutical delivery vehicles such as liposomes, nano-particles, polymer-based delivery systems, cellular delivery vectors, and dissolvable strips. In particular, the antioxidant composition may be added to mouthwashes, chewing gum, breath fresheners, lipstick or lip balm, toothpaste, dental floss, fluoride rinses, teeth whitener kits, and the like. Antioxidant compositions may also be added to dental devices, such as protective barrier materials. Antioxidant compositions may be formulated such that appropriate concentrations of antioxidants or other ingredients are present after addition to another product.

In one particular embodiment, the antioxidant composition may be included in a film-forming gel, such as a primarily water-based, pH-sensitive polymer-containing mucoadhesive that forms a thin, dry film when applied topically. The gel may adhere to a mucosal surface for a time after application, enhancing delivery of antioxidant compositions in some embodiments. The gel may be non-irritating, dry, non-oily, or non-sticky or may be made from Generally Regarded As Safe materials. The gel may form a dental device.

Both the carrier non-antioxidant components of the antioxidant composition and volume delivered in each use may be selected based on a variety of factors, including, but not limited to, the mode of delivery, the form or concentration in which the antioxidants are to be supplied before formulation into the antioxidant composition and the ability or need to administer a precise amount of antioxidants.

Antioxidant compositions may be prepared in any method able to achieve a final composition containing all of the components. One of ordinary skill in the art will appreciate that components may be added in particular orders or that preparation may proceed separately from some components prior to combination into the final composition. For example, it may be beneficial to first dissolve certain antioxidants in solvents before their addition to the final composition.

Effects of Antioxidant Compositions

The antioxidant compositions of the invention may have any variety of positive effects resulting from decreased oxidative damage by dental devices. In one embodiment, they may be used to treat or prevent oral diseases. Oral diseases may include periodontal disease as well as other oral sores, lesions, ulcers or wounds. The antioxidant compositions of the invention may also generally be used to promote oral health, such as gingival health and to enhance wound healing at intra-oral surgical sites, including dental implant sites.

According to specific embodiments, the antioxidant compositions may generally promote healing. Without limiting these embodiments to a specific mechanism of action, healing may be carried out primarily through mobile cells able to migrate to different locations to participate in healing. Such cells may include juvenile cells such as precursor cells or multipotent stem cells, as well as mobile adult cells, such as fibroblasts. Specifically, mobile cells may include human gingival fibroblasts or human periodontal ligament cells.

A periodontal disease may include infection or inflammation of the gingiva, periodontal ligament, teeth and or supporting bone. According to one embodiment, the antioxidant compositions of the invention may be used to treat or prevent periodontal disease such as periodontitis and gingivitis by treating a soft oral tissue. Patients with gingivitis may display red, swollen gums that bleed easily without substantial discomfort. Gingivitis may progress to periodontitis, for example, where a bacterial plaque spreads under the gum line. Toxins produced by infecting bacteria may irritate the gingiva and may induce a chronic inflammatory response. Patients with periodontitis may present gingiva that have separated from the teeth, creating pockets that may be or may become infected. Progression of periodontitis may be marked by deepening pockets or destruction of gingiva or bone. Teeth may loosen and either fall out or require extraction.

In serious periodontal disease, the periodontal ligament, a soft tissue which helps anchor a tooth from its root to the underlying bone, may also become damaged. While this problem may be partially addressed by healing surrounding gingival tissue using gingival fibroblasts, it may also be treated or prevented by increasing the number or mobility of periodontal ligament cells, which may be able to directly repair damage to the periodontal ligament. Accordingly, antioxidant compositions of the invention may be able to decrease apoptosis in, increase proliferation of, or increase migration of periodontal ligament cells.

Some embodiments of the present invention may address excessive or exuberant inflammation. The inflammatory response is an important pathway employed by the body. However, in excessive inflammation, healthy cells are destroyed as collateral damage. Most damage is host derived because of reactive oxygen species, cytokines, chemokines, matrix metalloproteases, and other factors. Tissue destruction is particularly pronounced in situations of chronic inflammation. In healthy gingival cells, robust collagen matrix surrounding long fibroblast cells are observed beneath the epithelial cells. In gingival cells with a prolonged inflammatory response, the fibroblast cells have been displaced with inflammatory cells, and much of the collagen matrix is destroyed. Antioxidant compositions have been shown to inhibit or modulate inflammatory markers and mediators, as well as markers in the bone resorptive pathway. Further, this has had a minimal effect on tissue health. Accordingly, antioxidant compositions of the invention may be able to modulate, inhibit, or regulate the inflammatory pathway. In addition, compositions may be able to modulate, inhibit, or regulate the bone resorption pathway. This may be accomplished, in particular, by affecting IL-1, IL-6, and TNF-α.

Oxidative damage can affect all cell types. Accordingly, the treatment or preventative effects of the antioxidant compositions are not limited to gingival fibroblasts or periodontal ligament cells in all embodiments of the invention. For example, similar effects regarding apoptosis, proliferation, or migration may be seen in other oral cells, particularly other oral cells involved in wound healing, such as fibroblasts and fibroblast precursors. As a consequence, the site of therapeutic or preventative benefit provided by antioxidant compositions may not be fixed to the cells of the epithelial layer that actually contact the antioxidant compositions. Therapeutic or preventative benefit may also be provided to underlying cells in addition to the fibroblasts and fibroblast precursors, for example, the periodontal ligament, lamina propria and submucosal layers, including mesenchymal and periodontal ligament cells, and gingival fibroblasts. Finally, therapeutic effects may include a decrease in oral cancer, particularly as patients age.

In order to achieve therapeutic or preventative effects, antioxidants may be absorbed from the antioxidant compositions into the internal regions of oral soft tissues in some embodiments. However, in many cases of periodontal disease, it may be sufficient for the antioxidant compositions to merely contact the gingiva. In such instances, the ability of the antioxidant to reach and be absorbed by the gingival surfaces or by the tissues of the gingival sulcus, which is between the gingiva and tooth, may be sufficient.

On a cellular level, antioxidant compositions may act by preventing, reducing, or reversing oxidative damage. The exact mechanism of this damage may vary by the material released by the dental device and the cell affected. For example, antioxidants may prevent or reduce oxidative damage of some oral cells by interacting with a material released from the dental device to render it incapable or less capable of causing oxidative damage. In another example, antioxidants may prevent or reduce oxidative damage by rendering a second or later oxidative species generated by the material released from the dental device incapable or less capable of causing oxidative damage. In still another example, the antioxidants may induce a more effective cellular response to oxidative damage, for example, by suppressing a harmful inflammation pathway or by increasing the production of cellular components able to combat or repair oxidative damage. In one specific embodiment, exogenous antioxidants of the current invention may decrease or prevent the damaging effects of free radicals on dental tissues by supporting endogenous antioxidants, such as glutathione, CoQ10, and lipoic acid, and/or endogenous defense enzymes such as superoxide dismutase, catalase and glutathione peroxidase.

Method of Reducing Oxidative Damage

FIG. 1 illustrates a particular method 10 of reducing oxidative damage caused by a dental device. In step 20, a medical device is provided to the mouth of the patient. In step 30, an antioxidant composition is provided to the mouth of the patient. In step 40, the antioxidant is removed or dissipated. In step 60, if the medical device is subsequently removed, then in step 70 the antioxidant is no longer applied. If the medical device is not removed, then step 30 is repeated.

Although certain examples contained herein focus on methods for use in humans, similar methods may be used in other animals who have dental devices, such as mammals, particularly domesticated mammals. For example, certain pets may have fillings. Other domestic animals, such as horses, regularly have dental devices such as bits placed in their mouths. Antioxidant compositions may be formulated by one of ordinary skill in the art, using the above disclosure, in appropriate veterinary forms. For example, antioxidant concentrations in compositions intended for some animals may be higher due to increased saliva production in such animals as compared to humans or to allow for less-frequent administration, minimizing the effort needed to use the product, or to account for an increased tendency by animals to swallow material placed in the mouth instead of allowing it to sit on the soft oral tissues. Antioxidant compositions may also be delivered in products, for example as coatings or components of chew toys or in feed or treats, that are unique to the veterinary market. Further, indications for administration of antioxidant compositions of the invention may be different for veterinary patients due to different environmental sources of oxidative damage.

Method of Treating Oral Complications

In some embodiments, oral complications may be treated with an antioxidant containing compound. A patient is presented with an oral complication. In some embodiments, the oral complication will involve the soft tissue of the mouth. The patient's mouth is then provided with an antioxidant compound. The antioxidant compound is then dissipated. The mouth is then treated again. This is repeated until resolution of the oral complication. In some embodiments, the oral complication may be xerostomia, mucositis, or BRONJ. In some embodiments, the antioxidant compound will be one of the antioxidant compounds described in this disclosure.

In some embodiments in which BRONJ is treated, the present invention may assist in the sequestering and separation of nectrotic bone tissue from the healthy bone tissue. In other embodiments in which BRONJ is treated, the present invention may assist in the growth and healing of the necrotic bone. In other embodiments, the present invention may help in the growth of tissue over exposed bone. In addition, these may all occur in the same embodiment, or separately, or in any combination.

In some embodiments, any disease associated with a decrease in salivary anit-oxidants may be treated using antioxidants of the present disclosure. Additionally, some diseases involving immune suppression may be linked to low salivary anti-oxidant levels. For example, BRONJ, oral cancer, diabetes, and other diseases may have a decrease in salivary anti-oxidant levels. By providing or treating a patient with anti-oxidants described in the present disclosure, side-effects, complications, or the underlying disease itself may be addressed or treated.

While this method has been worded in terms of a patient, it is understood that this same method could be applied to an animal in a veterinary setting and is within the scope of the present disclosure.

Methods of Treating Inflammation

In some embodiments, inflammation generally may be prevented, reduced, or eliminated with an antioxidant compound. Such inflammation may be a localized or a systemic inflammation response. In particular, a patient may be administered one of the antioxidant compounds described in the present disclosure. This may be beneficial for inflammation in the mouth, oral cavity, or other regions associated therewith.

In particular, by using certain antioxidant compounds or combinations thereof, certain signal molecules may be regulated. For example and as shown in FIGS. 8A-14B, the use of various antioxidants may reduce the concentration and thus the inflammatory effect of a variety of biochemical signal molecules. These molecules may function at a variety of locations in the inflammation cascade. Further, the antioxidants may function to limit the activation of NF-κB, thus limiting the transcription of at least one of the inflammation signal proteins.

In addition to the reduction of inflammation signal molecules directly, these inflammatory markers have also been associated with a variety of oral diseases. High levels of oxidative stress and low levels of salivary antioxidants are a common theme in many oral diseases. By reducing the inflammatory markers associated with these diseases, the effects of these diseases may be ameliorated, eased, or completely removed. In addition, reducing the inflammatory markers may eradicate the underlying disease itself. Thus, by providing antioxidants to reduce inflammatory markers, oral diseases may be addressed. Further, as multiple oral diseases are implicated by these markers, multiple diseases may be addressed using antioxidants. These diseases could include oral cancer, xerostomia (dry mouth), TMJ, periodontitis, oral lichun planus, or any combinations thereof. The antioxidants used could be any of those described in this disclosure.

EXAMPLES

The present invention may be better understood through reference to the following examples. These examples are included to describe exemplary embodiments only and should not be interpreted to encompass the entire breadth of the invention.

Example 1

Antioxidant Compositions

Several specific antioxidant compositions have been prepared.

Formulation 1—Preparation of Gel

|  | Components | % w/w |
|---|---|---|
| Part A | Water | Remainder |
|  | Xylitol | 10.00 |
|  | Sodium citrate | 0.154 |
|  | Citric acid monohydrate | 0.010 |
| Part B | Antioxidants | 0.300-0.400 |
|  | Menthol | 0.100 |
|  | Thymol | 0.050 |
|  | Poloxamer 407 | 1.500 |
|  | PEG 600 | 2.000 |
|  | Propylene glycol | 2.000 |
|  | Ethanol | 5.000 |
| Part C | Ticalose ® CMC 2500 | 2.500 |

The gels for Formulation 1 may be prepared by dissolving xylitol, sodium citrate (if present), and citric acid in the water (Part A). The Part B components may be dissolved at 60° C. and added to the prepared Part A. The mixture of Part A and Part B may be stirred for 30 minutes and then ticalose (Part C) may be added gradually. The mixture Part A, Part B, and Part C may be stirred 2 hours and left overnight. The final gel may be stirred at low rotation (50 rpm) for 1 hour.

Formulation 2—Preparation of Film

|  | Components | % w/w |
|---|---|---|
| Part A | Water | Remainder |
|  | Pullulan | 9.50 |
|  | Xanthan gum | 0.06 |
| Part B | Antioxidants | 0.15-0.30 |
|  | Menthol | 0.10 |
|  | Poloxamer 407 | 0.75 |
|  | PEG 600 | 0.65 |
|  | Propylene glycol | 1.00 |
| Part C | Water | 37.60 |
|  | Sodium citrate | 0.154 |
|  | Citric acid monohydrate | 0.010 |

The film for 2 may be prepared by stirring the components of Part A to form a gel and storing the gel overnight. Part C may be prepared by mixing the components. The components of Part B may be stirred at 60° C. for 30 minutes followed by addition of the prepared Part C. The mixture Part B and C may be stirred for an additional 30 minutes. Next, the prepared mixture of Part B and Part C may be added to the gel formed from Part A and mixed for 1 hour. The final mixture of Part A, Part B, and Part C may be poured on smooth surface and dried at ambient temperature to form a film.

Formulation 3—Preparation of Mouthwash

|  | Components | % w/w |
|---|---|---|
| Part A | Water | Remainder |
|  | Ethanol | 10.00 |
|  | Sodium citrate | 0.154 |
|  | Citric acid monohydrate | 0.010 |
| Part B | Antioxidants | 0.1-0.25 |
|  | Menthol | 0.100 |
|  | Thymol | 0.050 |
|  | Poloxamer 407 | 0.750 |
|  | PEG 600 | 1.000 |
|  | Propylene glycol | 1.000 |
|  | Ethanol | 5.000 |

Formulation 3 may be prepared by mixing the sodium citrate, citric acid, and ethanol in water (Part A). Components of Part B may be dissolved at 60° C. and added to Part A. The mixture of Part A and Part B may be stirred for 1 hour.

Formulation 4—Preparation of Oral Spray

|  | Components | % w/w |
|---|---|---|
| Part A | Water | Remainder |
|  | Ethanol | 10.00 |
|  | Sodium citrate | 0.154 |
|  | Citric acid monohydrate | 0.010 |
| Part B | Antioxidants | 0.3-0.45 |
|  | Menthol | 0.100 |
|  | Thymol | 0.050 |
|  | Poloxamer 407 | 1.500 |
|  | PEG 600 | 1.000 |
|  | Propylene glycol | 1.000 |
|  | Ethanol | 5.000 |

Formulation 4 may be prepared in generally the same manner as Formulation 4, then placed in spray containers.

Formulation 5—Preparation of Film-Forming Gel

|  | Components | % w/w |
|---|---|---|
| Part A | Phloretin | 0.3-0.5 |
|  | Poloxamer 407 | 1.500 |
|  | PEG 600 | 1.000 |
|  | Ethanol | 2.000 |
| Part B | Film-forming gel | Remainder |

Formulation 5 may be prepared by combining the Part A components then incorporating them into Part B. Application of the film-forming gel may provide a layer adhered to the oral mucosa that allows time-controlled release of antioxidants, which may increase the biological response to the antioxidants.

Example 2

Synergistic Effects of Antioxidants to Counteract Metal-Induced Toxicity on Fibroblasts In dentistry, the use of metals in fillings, braces, bridges and other prosthodontic restorations may form free radicals. Toxicity studies on commonly used metal salts found in fixed prosthodontic restorations showed that zinc (Zn) and copper (Cu) released from gold alloys, and nickel (Ni) released from nickel-chromium alloys have a highly significant cytotoxic activity on fibroblast cell cultures. A study was conducted to determine if oral fibroblasts are susceptible to damage from these agents which elevate reaction oxygen species (ROS). In this study, specific antioxidant (AO) combinations were investigated that counteract the effects of Zn, Cu and Ni on cultured oral fibroblast proliferation and oxidative damage. Oral fibroblasts obtained from human gingival (HGF) tissues were seeded into 96-well plates. After achieving 70% confluence, the cells were pre-treated with Zn, Cu and Ni for 30 and 60 minutes. Thereafter, cells were exposed to 10-5M of the bioactive AO mixtures; resveratrol (R), ferulic acid (F) phloretin (P) and tetrahydrocurcuminoids (T); (RFT, PFR, PFT) for 24 hours. Cell viability was monitored by MTS assay. The fluorescence response of dichlorodihydrofluorescein diacetate to various ROS was measured. Incubation of HGF cells in the presence of Zn, Cu and Ni resulted in a dose-dependent decrease of viable cells at 30 and 60 minutes. AO compounds increased recovery or survival of cells exposed to Zn, Cu and Ni. In summary, Zn, Cu and Ni increased ROS. AO treatment decreased ROS in the presence of Zn, Cu and Ni. The triple combinations of RFT, PFR or PFT were effective modulators in the presence of all insulting substances tested. These data indicate that pure AOs counteracted the detrimental effects of Zn, Cu and Ni in oral fibroblasts. In addition, the AOs decrease ROS activity by protecting the cells against free radical formation.

Example 3

Antioxidant Combinations Maintain Oral Fibroblast Viability After Exposure to Metal Induced Toxicity Toxicity studies on commonly used metal salts found in fixed prosthodontic restorations showed that zinc (Zn) and copper (Cu) released from gold alloys, and nickel (Ni) released from nickel-chromium alloys have a highly significant cytotoxic activity on fibroblast cell cultures. A study was conducted to determine if oral fibroblasts are susceptible to damage from these agents by decreasing cell viability and whether specific antioxidants (AO) in combinations can counteract these effects. Oral fibroblasts obtained from human gingival (HGF) tissues were seeded into 96-well plates. After achieving 70% confluence, the cells were pre-treated with Zn, Cu and Ni for 30 and 60 minutes. Thereafter, cells were exposed to 10-5M of the bioactive AO mixtures at single, double and triple combinations; resveratrol (R), ferulic acid (F), phloretin (P), and tetrahydrocurcuminoids (T) for 24 hours. Cell viability was monitored by MTS assay. Incubation of HGF cells in the presence of Zn, Cu and Ni resulted in a dose-dependent decrease of viable cells at 30 and 60 minutes. AO compounds increased recovery or survival of cells exposed to Zn, Cu and Ni. In summary, Zn, Cu and Ni increased ROS. AO treatment decreased ROS in the presence of Zn, Cu and Ni. The triple combinations of RFT, PFR or PFT are effective modulators in the presence of all insulting substances tested. These data indicate that pure AOs counteracted the detrimental effects of Zn, Cu and Ni in oral fibroblasts. In addition, the AOs decrease ROS activity by protecting the cells against free radical formation.

Example 4

Antioxidants Effects on Human Gingival and Periodontal Ligament Fibroblast Cells After Exposure to Metal Induced Toxicity of Varying Concentrations Toxicity studies on commonly used metal salts found in fixed prosthodontic restorations showed that zinc (Zn) and copper (Cu) released from gold alloys, and nickel (Ni) released from nickel-chromium alloys have a highly significant and dose-dependent cytotoxic activity on fibroblast cell cultures. A study was done to determine the antioxidant effect on fibroblasts from human gingival (HGF) and human periodontal ligament (HPDF) cells exposed to increasing concentration of cytotoxic metals. HGF and HPDF cells were extracted and seeded with 10% fetal bovine serum (FBS). Both the HGF and HPDF cells were then exposed to one of $3\times10^{-4}$M or $2\times10^{-4}$M $ZnCl_2$, $2\times10^{-3}$M or $1\times10^{-3}$M $NiCl_2$, $5\times10^{-4}$M or $4\times10^{-4}$M $CuCl_2$. Next, the samples were treated with bioactive antioxidant (AO) mixtures at single, double, and triple combinations; resveratrol (R), ferulic acid (F), phloretin (P), and tetrahydrocurcuminoids (T). Both the HGF and HPDF cells were then monitored by MTS, ROS, and BrdU assays. Results can be seen in FIGS. 2-6. In summary, all metals tested decreased cell viability in a dose-dependent manner, and Cu increased ROS while Ni and Zn had little effect on ROS. AOs increased cell viability in Zn and Cu treated cells better than Ni treated cells. In addition, it was observed that new DNA synthesis was highest in Zn treated cells in the presence of AO triple combinations. Also, triple combination AOs decreased ROS in Cu and Ni treated cells better than Zn treated cells.

Example 5

Alternative Formulations

In addition to the formulations described in Example 1, alternative formulations are disclosed herein, which may be particularly beneficial in a veterinary setting.

Formulation 1—Veterinary Gel

| | Components | % w/w |
|---|---|---|
| Part A | Water | 65.38 |
| | Ultrez 10 NF | 0.25 |
| Part B | Potassium Sorbate | 0.10 |
| | Polaxamer 407 | 3.50 |
| | Sorbitol | 15.00 |
| | Sodium Benzoate | 0.10 |
| Part C | 18% NaOH | 0.61 (0.5 ml) |
| Part D | EDTA 2x NaOH dihydrate | 0.05 |
| Part E | Phloretin | 0.28 |
| | Ferulic Acid | 0.20 |
| | Tetrahydrocurcumin | 0.38 |
| | 18beta Glycyrrhetinic acid | 0.20 |
| | L-Menthol | 0.05 |
| | Thymol | 0.05 |
| | Ethyl Vanillin | 0.15 |
| | Propylene Glycol | 6.00 |
| | PEG 600 | 6.00 |
| Part F | Ticalose | 1.70 |

Formulation 1 may be prepared by stirring the elements of Part A for 30 minutes. The elements of Part B may then be added to Part A. The mixture A+B could then be neutralized by Part C and stirred 30 minutes followed by the addition of Part D and stirred an additional 15 minutes. Part E could be prepared separately and after dissolution at ~60° C. could be added to the mixture (A+B+C+D) and then stirred for 30 minutes. Part F could then be gradually added and stirred for 60 minutes and then left overnight. The total mixture could then be stirred for 30 minutes at low rotation. The pH of the prepared formulation could be 5.8.

Formulation 2—Veterinary Gel

| | Components | % w/w |
|---|---|---|
| Part A | Water | 65.33 |
| | Ultrez 10 NF | 0.25 |
| Part B | Potassium Sorbate | 0.10 |
| | Polaxamer 407 | 3.50 |
| | Sorbitol | 15.00 |
| | Sodium Benzoate | 0.10 |
| Part C | 18% NaOH | 0.61 (0.5 ml) |
| Part D | EDTA 2x NaOH dihydrate | 0.05 |
| Part E | Phloretin | 0.28 |
| | Ferulic Acid | 0.20 |
| | Tetrahydrocurcumin | 0.38 |
| | 18beta Glycyrrhetinic acid | 0.20 |
| | L-Menthol | 0.05 |
| | Thymol | 0.05 |
| | Ethyl Vanillin | 0.15 |
| | Propylene Glycol | 6.00 |
| | PEG 600 | 6.00 |
| Part F | Cholorphyllin sodium copper salt | 0.05 |
| Part G | Ticalose | 1.70 |

Formulation 2 may be prepared by stirring the elements of Part A for 30 minutes. The elements of Part B may then be added to Part A. The mixture A+B could then be neutralized by Part C and stirred 30 minutes followed by the addition of Part D and stirred an additional 15 minutes. Part E could be prepared separately and after dissolution at ~60° C. could be added to the mixture (A+B+C+D) and then stirred for 30 minutes. Part F could then be dissolved in the mixture and then Part G could be gradually added and stirred for 60 minutes and then left overnight. The total mixture could then be stirred for 30 minutes at low rotation. The pH of the prepared formulation could be 5.8.

Formulation 3—Veterinary Gel

| | Components | % w/w |
|---|---|---|
| Part A | Water | 65.33 |
| | Ultrez 10 NF | 0.25 |
| Part B | Potassium Sorbate | 0.10 |
| | Polaxamer 407 | 3.50 |
| | Sorbitol | 15.00 |
| | Sodium Benzoate | 0.10 |
| Part C | 18% NaOH | 0.61 (0.5 ml) |
| Part D | EDTA 2x NaOH dihydrate | 0.05 |
| Part E | Phloretin | 0.28 |
| | Ferulic Acid | 0.20 |
| | Tetrahydrocurcumin | 0.38 |
| | 18beta Glycyrrhetinic acid | 0.20 |
| | L-Menthol | 0.025 |
| | Thymol | 0.025 |
| | Ethyl Vanillin | 0.15 |
| | Propylene Glycol | 6.00 |
| | PEG 600 | 6.00 |
| Part F | Ticalose | 1.70 |

Formulation 3 may be prepared by stirring the elements of Part A for 30 minutes. The elements of Part B may then be added to Part A. The mixture A+B could then be neutralized by Part C and stirred 30 minutes, followed by the addition of Part D and stirred an additional 15 minutes. Part E could be prepared separately and after dissolution at ~60° C. could be added to the mixture (A+B+C+D) and then stirred for 30 minutes. Part F could then be gradually added and stirred for 60 minutes and then left overnight. The total mixture could then be stirred for 30 minutes at low rotation. The pH of the prepared formulation could be 5.8.

Formulation 4—Veterinary Gel

|  | Components | % w/w |
|---|---|---|
| Part A | Water | 65.08 |
|  | Ultrez 10 NF (Lubrizol) | 0.25 |
| Part B | Potassium Sorbate | 0.10 |
|  | Polaxamer 407 | 3.50 |
|  | Sorbitol | 15.00 |
|  | Sodium Benzoate | 0.10 |
| Part C | 18% NaOH | 0.61 (0.5 ml) |
| Part D | EDTA 2x NaOH dihydrate | 0.05 |
| Part E | Phloretin | 0.28 |
|  | Ferulic Acid | 0.20 |
|  | Tetrahydrocurcumin | 0.38 |
|  | 18beta Glycyrrhetinic acid | 0.00 |
|  | L-Menthol | 0.025 |
|  | Thymol | 0.025 |
|  | Ethyl Vanillin | 0.15 |
|  | Propylene Glycol | 6.00 |
|  | PEG 600 | 6.00 |
| Part F | Cholorophyllin sodium copper salt | 0.05 |
| Part G | Ticalose | 1.70 |

Formulation 4 may be prepared by stirring the elements of Part A for 30 minutes. The elements of Part B may then be added to Part A. The mixture A+B could then be neutralized by Part C and stirred 30 minutes followed by the addition of Part D and stirred an additional 15 minutes. Part E could be prepared separately and after dissolution at ~60° C. could be added to the mixture (A+B+C+D) and then stirred for 30 minutes. Part F could then be dissolved in the mixture and then Part G could be gradually added and stirred for 60 minutes and then left overnight. The total mixture could then be stirred for 30 minutes at low rotation. The pH of the prepared formulation could be 5.8.

Formulation 5—Veterinary Gel

|  | Components | % w/w |
|---|---|---|
| Part A | Water | 66.29 |
|  | Potassium Sorbate | 0.10 |
|  | Polaxamer 407 | 3.50 |
|  | D-Sorbitol | 15.00 |
|  | Sodium Benzoate | 0.10 |
|  | EDTA | 0.05 |
| Part B | Phloretin | 0.28 |
|  | Ferulic Acid | 0.20 |
|  | Tetrahydrocurcuminoids CG ™ | 0.38 |
|  | 18beta Glycyrrhetinic acid | 0.20 |
|  | L-Menthol | 0.025 |
|  | Thymol | 0.025 |
|  | Ethyl Vanillin | 0.15 |
|  | Propylene Glycol | 6.00 |
|  | PEG 600 | 6.00 |
|  | Cholorophyllin sodium copper salt | 0.00 |
| Part C | Ticalose | 1.70 |

The preparation for Formulation 5 is similar to that of Formulations 1-4.

Formulation 6—Veterinary Gel

|  | Components | % w/w |
|---|---|---|
| Part A | Water | 66.26 |
|  | Potassium Sorbate | 0.10 |
|  | Polaxamer 407 | 3.50 |
|  | D-Sorbitol | 15.00 |
|  | Sodium Benzoate | 0.10 |
|  | EDTA | 0.05 |
| Part B | Phloretin | 0.28 |
|  | Ferulic Acid | 0.20 |
|  | Tetrahydrocurcuminoids CG ™ | 0.38 |
|  | 18beta Glycyrrhetinic acid | 0.20 |
|  | L-Menthol | 0.025 |
|  | Thymol | 0.025 |
|  | Ethyl Vanillin | 0.15 |
|  | Propylene Glycol | 6.00 |
|  | PEG 600 | 6.00 |
|  | Cholorophyllin sodium copper salt | 0.05 |
| Part C | Ticalose | 1.70 |

The preparation for Formulation 6 is similar to that of Formulations 1-4.

Formulation 7—Veterinary Spray

|  | Components | % w/w |
|---|---|---|
| Part A | Water | 68.92 |
|  | Sodium hyaluronate | 0.05 |
|  | Potassium sorbate | 0.10 |
|  | Sodium citrate | 0.20 |
|  | Sodium benzoate | 0.10 |
|  | EDTA | 0.04 |
|  | Poloxamer 407 | 3.50 |
|  | D-Sorbitol | 10.0 |
|  | Saccharin | 0.04 |
| Part B | Phloretin | 0.28 |
|  | Ferulic Acid | 0.20 |
|  | Tetrahydrocurcuminoids CG ™ | 0.38 |
|  | 18beta Glycyrrhetinic acid | 0.20 |
|  | L-Menthol | 0.02 |
|  | Thymol | 0.02 |
|  | Ethyl Vanillin | 0.15 |
|  | Propylene Glycol | 8.00 |
|  | PEG 600 | 8.00 |

The preparation for Formulation 7 is similar to that of Formulations 1-4.

While the above exemplary embodiments are couched in terms of veterinary application, it will be appreciated that these same formulations could be applied in other areas, for example in human treatment. In addition, it will be appreciated that a variety of compounds have been used for antibiotic, antimicrobial, flavoring, antioxidant, solubility, stabilization, preservative, or other reactive functions, but many other compounds are known in the art and could be substituted in without deviating from the spirit and scope of this disclosure. Different flavoring agents might be added, or different coloring agents might be added to make the embodiments more palatable or agreeable either to veterinary or human use. In addition, compounds may have been selected for gelling, adhesion, or other functional purposes, but many other compounds are known in the art and could be substituted without deviating from the spirit and scope of this disclosure. Further, the formulations were described in terms of gels and sprays, but could also include sprayable liquids, gels, powders, pastes, or any other delivery formulation as is known in the art.

Example 6

Treatment of Xerostomia

Xerostomia is a dryness of the mouth because of a lack of saliva. While there are many causes of this, it can be associated with cancers and treatments of cancers. A variety of patients were treated who had indications of xerostomia. Each patient was treated with an antioxidant gel prepared according to the present disclosure. Improvement in the condition was typically seen within 1 week.

Patient 1 was a male, age 57, who was in remission from non-small cell adenocarcinoma of the lung with bone metastases. Patient 2 was a male, age 59, who had Stage IV non-small cell adenocarcinoma of the lung with bone metastases. Patient 3 was a female, age 67, who had Stage IV renal cell carcinoma of the kidney with bone metastases. Patient 4 was a male, age 52, who had Stage III nasopharynx squamous cell carcinoma. Patient 5 was a male, age 74, who had Stage II Laryngeal cancer. Patient 6 was a female, age 72, with Stage III neck cancer. Patient 7 was a male, age 22, who had graft-versus-host disease subsequent to a stem cell transplant. Patient 8 was a male, age 54, who had multiple myeloma. Patient 9 was a male, age 69, with Stage IV renal carcinoma with multiple bone metasteses. Patient 10 was a female, age 42, who had Stage IV breast cancer. Patient 11 was a female, age 38, who had Stage II adenoid cystic carcinoma. Patient 12 was a male, age 85, who had Stage IV renal cell carinoma with bone metasteses.

In nearly each case (11 out of 12), improvement was seen in the condition. Patient 3 did not see an improvement, but this was hypothesized to be due to the use of CPAP each night.

In a comparable study involving 30 additional patients, a total of 75% reported relief from dry mouth conditions after 48 hours.

Example 7

Treatment of Mucositis

Mucositis is the inflammation and ulceration of the mucous membrane lining of the digestive tract, but is often associated with the mouth. This is often brought on by cancer treatments like chemotherapy or radiotherapy. A patient who had indications of mucositis was treated with an antioxidant gel prepared according to the present disclosure. Improvement in the condition was seen within 1 week.

The patient was a male, 22 years old, who had graft-versus-host disease associated with a stem cell transplant. The patient had a perceptible increase in wetness in his mouth. In addition, there was significant improvement in the lesions on his tongue and mouth, as well as improvement in his dry lips.

Example 8

Treatment of Bisphosphonate-Related Osteonecrosis of the Jaw (BRONJ)

BRONJ is a necrosis of the jaw typically seen in association with cancer treatments using bisphosphonates by IV. This has been a very difficult problem to treat. A series of patients suffering from BRONJ were treated with an antioxidant prepared according to the present disclosure.

Patient 1 was a male, 56 years old, in remission from Stage IV non-small cell adenocarcinoma of the lung with bone metastases. He had maxillary osteonecrosis of the upper left quadrant, characterized as Stage 3 BRONJ. He had a history of Aredia® via IV administration for eight rounds from April 2010 to November 2010. He had a dentist who had to remove a tooth but inadvertently left root fragments. ONJ was diagnosed December 2010. The patient began administering an antioxidant according to the present invention twice a day starting Apr. 14, 2011. Patient was also taking Amoxicillin 1500 mg. daily from December 2010 to June 2011 and aqueous chlorhexidine gluconate 2% from Jan. 31, 2011 to present. Patient saw resolution of the osteonecrosis Jun. 6, 2011, or 7 weeks, 4 days, after use of an antioxidant according to the present disclosure.

Patient 2 was a male, 59 years old, with Stage IV non-small cell adenocarcinoma of the lung with bone metastases. He had mandibular osteonecrosis with a right exposed mandibular torus, characterized as Stage 2 BRONJ. He had a history of Zometa® via IV administration for six rounds from September 2010 to March 2011. ONJ was discovered November 2010. The patient began administering an antioxidant according to the present invention twice a day starting Apr. 27, 2011. Patient was also taking aqueous chlorhexidine gluconate 2% from Jan. 31, 2011 to resolution of the ONJ. Patient saw resolution of the osteonecrosis Jun. 15, 2011, or 7 weeks after use of an antioxidant according to the present disclosure.

Patient 3 was a female, 66 years old, with Stage IV clear cell renal cell carcinoma with bone metastases. She had mandibular osteonecrosis with a right exposed mandibular ridge from the 2nd premolar area to the ramus, characterized as Stage 3 BRONJ. She had a large lytic lesion in her right femur with a pathologic fracture that led to right femur resection surgery and total right knee replacement in January 2009. Pathology showed metastatic carcinoma with extensive necrosis involving the right femur. She had a history of Zometa® via IV administration beginning in June 2009, but because of other medical complications was only given every three months. Once the necrosis was discovered, Zometa® was administered once in October 2010 and once in January 2011. The BRONJ was surgery-induced with the removal of a tooth in April 2009. The patient discovered ONJ symptoms in April 2009, but it was not diagnosed until August 2010. The patient had mal breath and suffered social dysfunction because of concerns regarding the breath. She also experienced a significant amount of discomfort from the complications of her BRONJ.

The patient began administering an antioxidant according to the present invention twice a day starting Jun. 23, 2011. She was also taking aqueous chlorhexidine gluconate 2% from June, 2011 to present. In initial treatment, she saw improvement in mal breath and a reduction in pain. The health of the surrounding tissue was improved but there was no resolution of the necrosis. After 9½ weeks on one embodiment of the present disclosure, she was changed to a different embodiment of the present invention. After 3½ weeks using the different embodiment, there has been a new layer of tissue covering the bone, and continued improvement and expected complete resolution of her BRONJ.

Example 9

Additional Studies of Various Antioxidants for the Prevention, Reduction, or Elimination of Inflammation Generally Example 9 relates to the prevention, reduction, or elimination of inflammation using antioxidants. In particular, additional data for various antioxidants and their effect on various biological molecules involved with inflammation is described.

The following methods were used:
Cell Culture—PBMCs were isolated from buffy coats derived from healthy donors (Sylvan N. Goldman Oklahoma Blood Institute, Oklahoma City, Okla., USA) by density gradient centrifugation (Ficoll-Paque plus; GE Healthcare, Piscataway, N.J., USA). Oleuropein (purity=80.17%) was purchased from Sabinsa Corporation (Payson, Utah, USA). Silymarin (purity ≥95%), ferulic acid (purity ≥98%), hesperetin (purity ≥95%), resveratrol (purity ≥99%), and phloretin (purity ≥99%) were purchased from Sigma-Aldrich (St Louis, Mo., USA). Dimethyl sulfoxide (DMSO) (purity=99.90%) was purchased from EMD Millipore (Billerica, Mass., USA). Oleuropein, silymarin, ferulic acid, hesperetin, resveratrol and phloretin were provided as 0.1M stock solutions prepared in DMSO by Periosciences Ltd (Dallas, Tex., USA). Combinations of anti-oxidants had a final combined concentration of 0.1M.

PBMCs were seeded at either $4 \times 10^5$ or $1.2 \times 10^6$ cells in 96- or 48-well tissue culture plates (BD Biosciences, Franklin Lakes, N.J., USA) respectively. PBMCs were pre-treated with single antioxidants at a concentration of $1 \times 10^{-4}$ M or combinations of antioxidants with a combined concentration of $1 \times 10^{-4}$ M for 2 hrs prior to stimulation. PBMCs were then stimulated for 16 hrs with purified LPS isolated from the bacterium *Actinobacillus actinomycetemcomitans*, strain Y4 (Aa Y4); a kind gift of Dr Kirkwood, Univ. South Carolina) at a concentration of 1 μg/ml in the presence of antioxidants. Media were collected, spun at 1600 RPM and cell-free supernatants transferred to fresh tubes and stored at −20 C. Cell viability was assayed using CellTiter 96® AQueous One Solution Reagent (Promega, Madison, Wis., USA) following the manufacturers guidelines. 20 μl of the reagent was added to each well and incubated for 2 hrs under culture conditions. After 2 hrs the absorbance at 490 nm was recorded using a 96-well plate reader.

ELISA and Multiplex Assays—Human tumour necrosis factor-alpha (TNF-α) capture and detection Abs were purchased from Life Technologies (Carlsbad, Calif., USA) and used for the development of a TNF-α sandwich ELISA according to the manufacturer's instructions. Cell culture supernatants were analyzed using a 96-well plate reader with absorbance at 450 nm (reference 650 nm).

Human Cytokine Fluorokine MAP kit was purchased from R & D Systems (Minneapolis, Minn., USA). Readouts included TNF-α, IL-1α, IL-1β, IL-1Ra, IL-2, IL-4, IL-5, IL-6, IL-8, IL-10, IL-17, macrophage inflammatory protein (MIP)-1α (MIP-1α), MIP-1β, interferon-γ (IFN-γ), granulocyte-colony stimulating factor (G-CSF), granulocyte macrophage-colony stimulating factor (GM-CSF), macrophage chemotactic protein (MCP-1), CCL5, CXCL5, vascular endothelial growth factor (VEGF), thrombopoietin (TPO) and fibroblast growth factor basic (FGFb). Supernatants were assayed on a Bio-Plex 200 (BioRad, CA, USA).

RT-PCR Assays—Total RNA was extracted from homogenized cells using the miRNeasy kit (Qiagen, Valencia, Calif., USA) according to the manufacturer's protocol. Total RNA quantified on Nanodrop (ThermoScientific, Rockford, Ill., USA) was used for first strand cDNA synthesis using the SS RTIII kit (Life Technologies, Carlsbad, Calif., USA). Real-time PCR was performed using EvaGreen 2× master mix (Biotium, Hayward, Calif., USA), 10 pmol forward and reverse gene specific primers and 1 ul of 1:10 diluted cDNA. GAPDH was used as endogenous control. The fold change was calculated using 2-ΔΔCt method and the control was set at 1. Custom primers were purchased from Sigma-Aldrich (St Louis, Mo., USA). Primer sequences for TNF-α were Forward, CCCTTTATTACCCCCTCCTTCA, Reverse: ACTGTGCAGGCCACACATTC. Primer sequences for IκB-α were: Forward, ATCAGCCCTCATTTGTTGC, Reverse: ACCACTGGGGTCAGTCACTC.

Data Analysis—Statistics were performed using two-tailed t-test or one-way analysis of variance (ANOVA). Statistical significance is indicated by an asterisk *, where $p \leq 0.05$. Error bars on all graphs indicate standard error of mean (SEM) or standard deviation (SD).

The following results were obtained:

Stimulation of PBMCs with Aa Y4 LPS—To establish the optimal concentrations of anti-oxidants and LPS for this study, dose and kinetic experiments were performed. The doses examined were: $1 \times 10^{-4}$, $1 \times 10^{-5}$ and $1 \times 10^{-6}$ M while the challenge concentrations of Aa Y4 LPS were 1, 10, 100 or 1000 ng/ml. Whole blood was stimulated with several concentrations of *E. coli* or Aa Y4 LPS and TNF-α production quantified by ELISA over 3 time-points: 16, 24 and 48 hrs. From these data the concentration of 1 μg/ml of Aa Y4 LPS and a time-point of 18 hrs were chosen for the following experiments as they resulted in a final concentration of TNF-α being at the top end of the quantitative range of the ELISA. For the anti-oxidants a concentration of 1×10-4M (equating to 0.01% DMSO) and a pre-incubation period of 2 hrs were found to be the optimal culture conditions that did not adversely affect cell viability.

PBMCs were utilized for the proceeding experiments for the following reasons. They were considered to be representative of the infiltrating leukocyte population present during acute inflammation and therefore any effect of the anti-oxidants on their ability to release inflammatory mediators would likely be of significance in vivo. Secondly, the PBMCs present within whole blood are those cells bearing TLR4 and are therefore the LPS-responsive component. Lastly, the removal of erythrocytes allowed for the use of the CellTiter system in the assessment of any cytotoxic effects conferred by the anti-oxidants or their carrier DMSO—thereby ensuring that any perturbation of the inflammatory profile was as a result of altered biology and not a reduction in the number of viable responder cells present.

Figure 7:
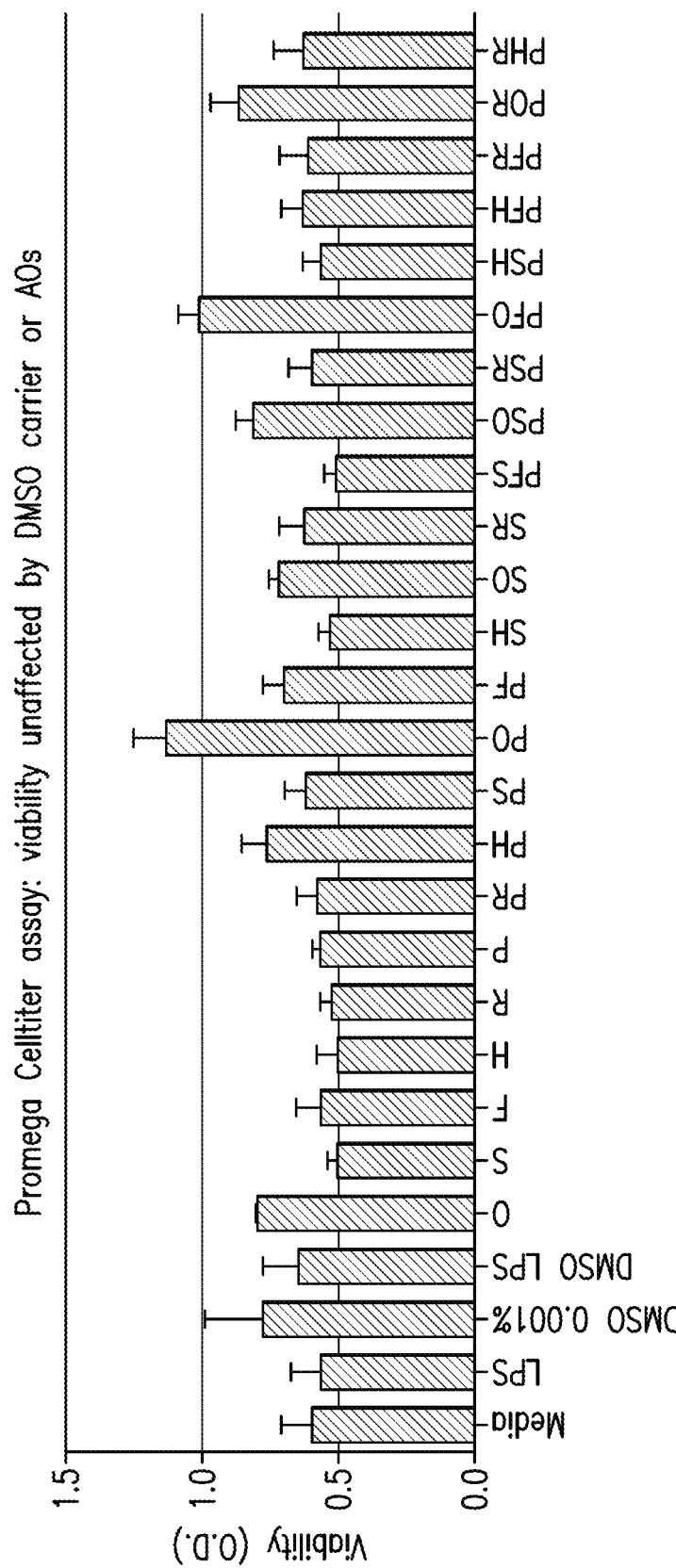
FIG. 7 shows results of various compounds, including antioxidants, on cell viability.
Figure 8A:
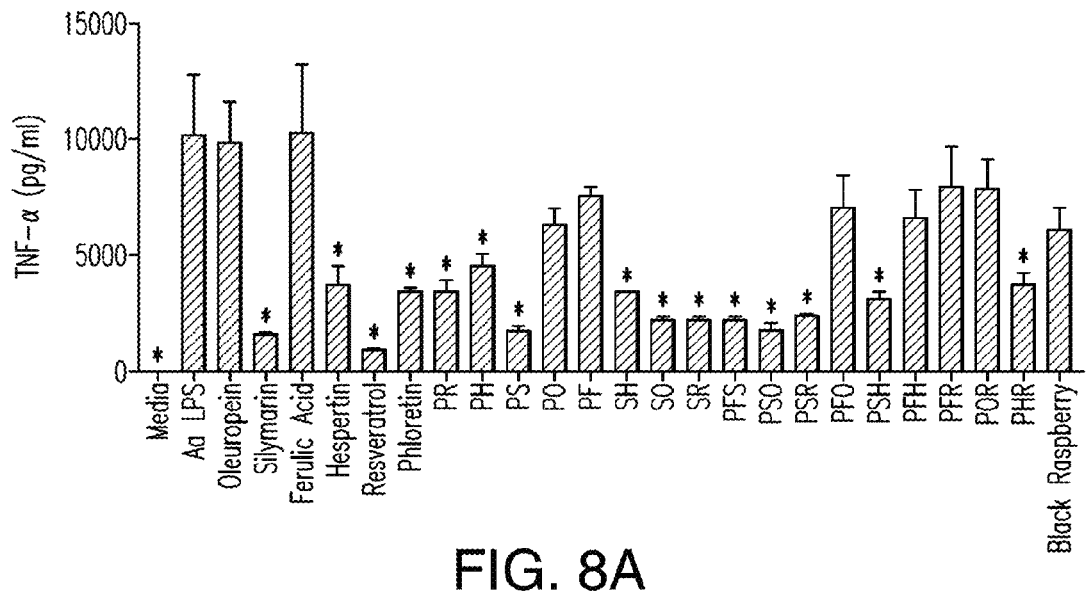
FIG. 8A shows the results of various antioxidants on TNF-α.

$4 \times 10^5$ PBMCs were cultured either in media alone, media containing 0.01% DMSO, stimulated with 1 μg/ml of Aa Y4 LPS, or LPS in the presence of DMSO for 18 hrs. Subsequently TNF-α production was quantified by ELISA (as shown in FIG. 8A) and cell viability also assessed (as shown in FIG. 7). Unstimulated PBMCs did not produce detectable levels of TNF-α while the addition of LPS resulted in significant TNF-α production (a final concentration of approximately 10,000 pg/ml). Similarly, cell viability was not significantly altered following the addition of LPS, or in the presence of 0.01% DMSO or when both LPS and DMSO was present—thus indicating that any alteration in the cytokine profile with the addition of anti-oxidant was not an indirect effect of decreased responder cell viability.

Cytokine profile of PBMCs activated with Aa Y4 LPS-4× $10^5$ PBMCs were cultured in media alone or stimulated with LPS for 18 hrs and the supernatant assayed for the cytokines and chemokines. As shown in FIGS. 8A-13B, upon stimulation with LPS significant increases were observed in TNF-α, IL-1α, IL-1β, G-CSF, GM-CSF, IFN-γ, IL-6, IL-10, MCP-1, CCL5, MIP-1α, MIP-1β and IL-Ra production. No significant increase was observed in CXCL5, IL-8 or VEGF levels, while the cytokines IL-4, FGF basic, IL-2, IL-5, IL-17 and TPO were undetectable. No significant decrease in cell viability was observed with LPS stimulation (as shown in FIG. 7).

Figure 9A:
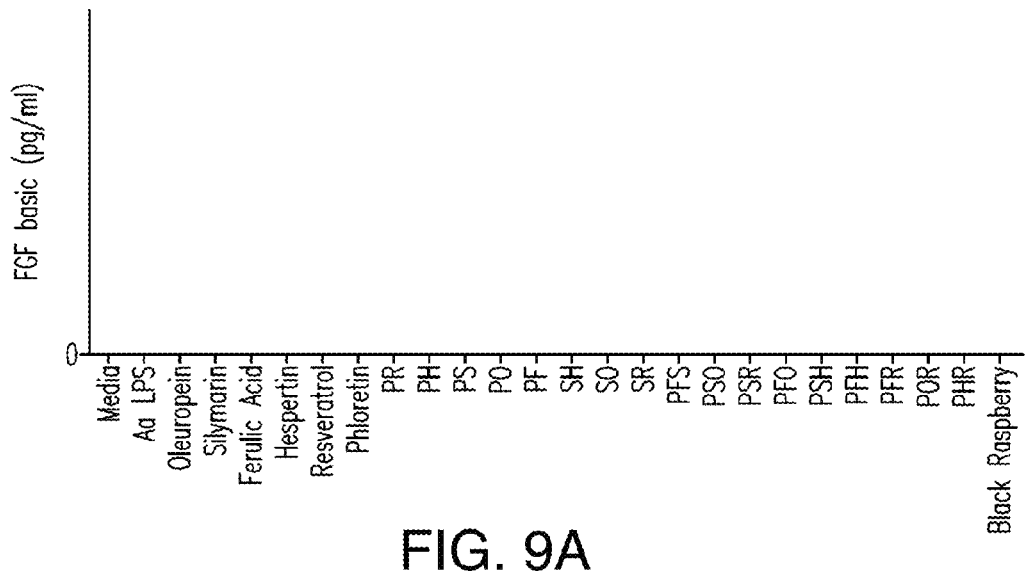
FIG. 9A shows the results of various antioxidants on FGF basic.
Figure 9B:
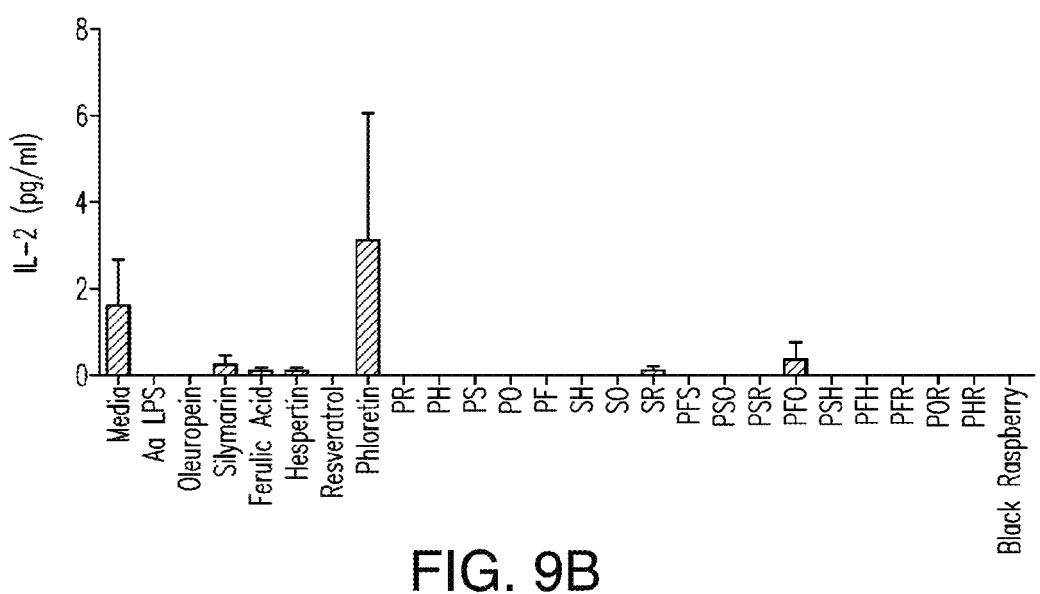
FIG. 9B shows the results of various antioxidants on IL-2.
Figure 9C:
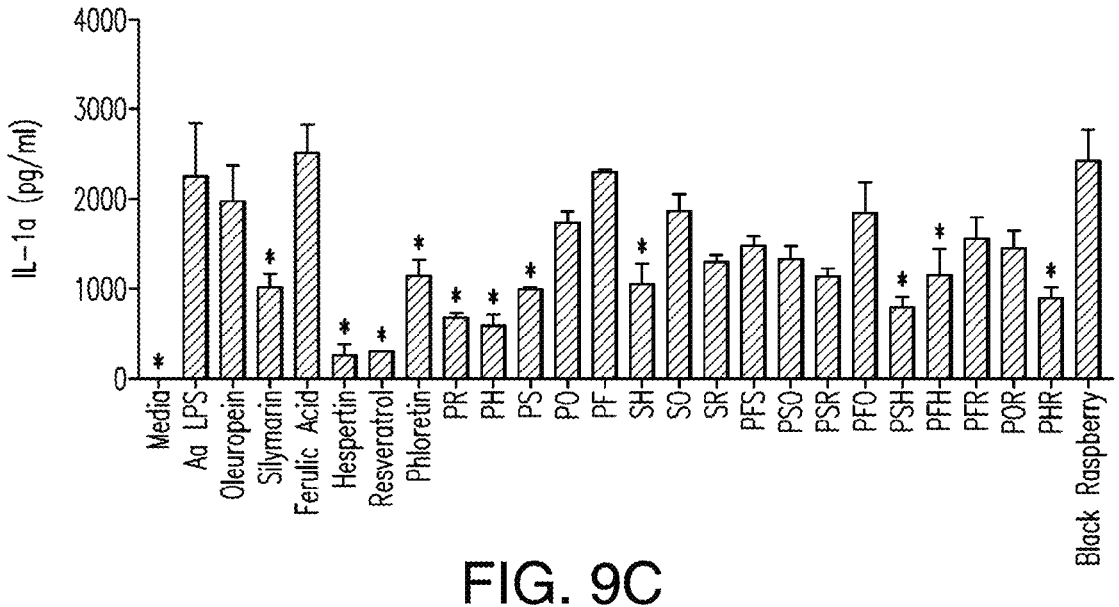
FIG. 9C shows the results of various antioxidants on IL-1α.
Figure 9D:
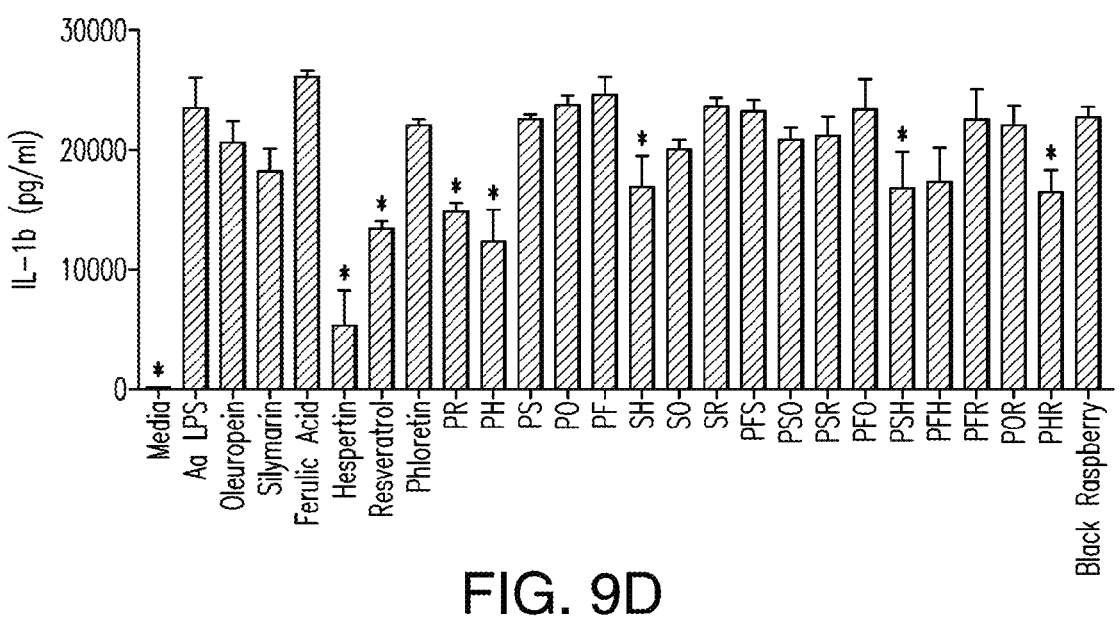
FIG. 9D shows the results of various antioxidants on IL-1β.
Figure 10A:
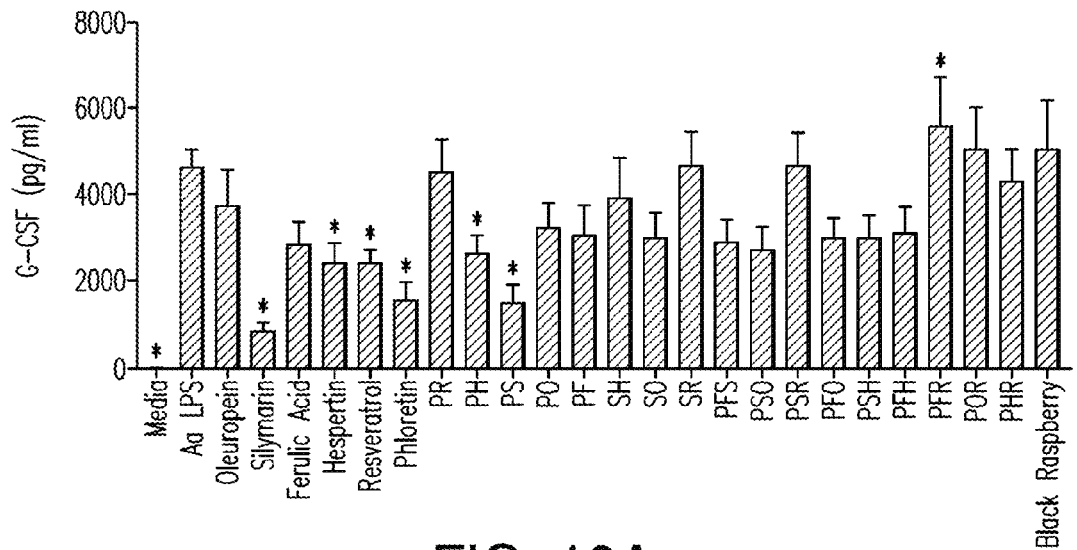
FIG. 10A shows the results of various antioxidants on G-CSF.
Figure 10B:
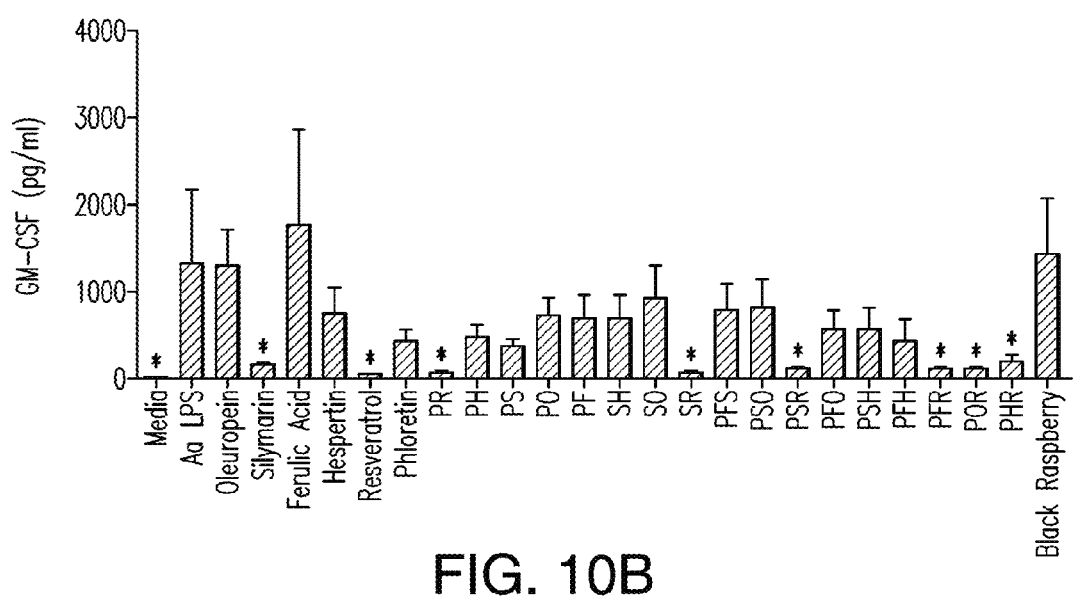
FIG. 10B shows the results of various antioxidants on GM-CSF.
Figure 10C:
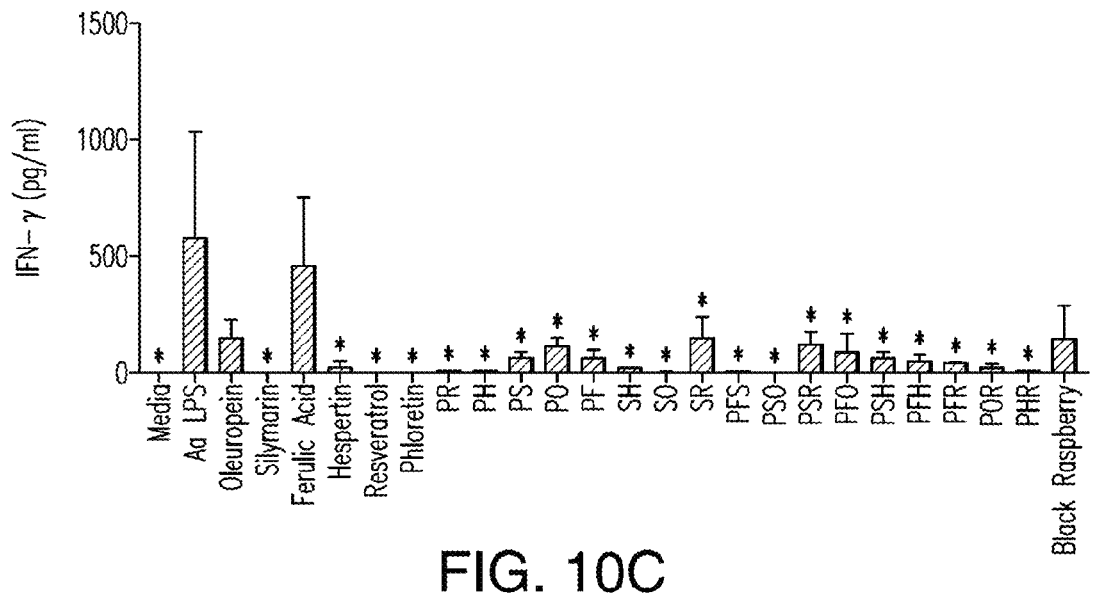
FIG. 10C shows the results of various antioxidants on IFN-γ.
Figure 10D:
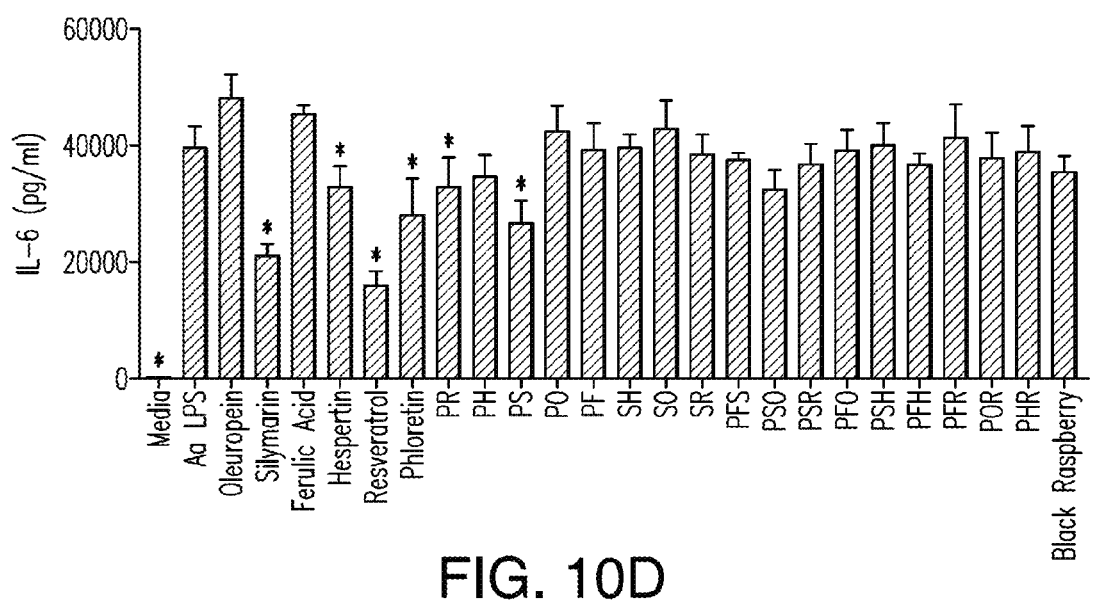
FIG. 10D shows the results of various antioxidants on IL-6.

The anti-oxidants phloretin, silymarin, hesperetin and resveratrol inhibit the LPS response—PBMCs were pre-treated with anti-oxidants at a concentration of $1 \times 10^{-4}$ M for 2 hrs prior to stimulation with LPS, for 18 hrs. Significant inhibition of TNF-α production was achieved by the presence of the anti-oxidants phloretin, silymarin, hesperetin and resveratrol, while oleuropein and ferulic had no observed effect (FIG. 8A). Significantly, phloretin and hesperetin reduced TNF-α levels by more than 50% compared to controls, while silymarin and resveratrol reduced levels by more than 75%. In addition to TNF-α several other pro-inflammatory cytokines were significantly lower with anti-oxidant treatment. Phloretin, silymarin, hesperetin and resveratrol inhibited the production of the important pro-inflammatory cytokine IL-1α (FIG. 9C), while hesperetin and resveratrol also decreased levels of IL-1β (FIG. 9D). Phloretin, silymarin, hesperetin and resveratrol also inhibited the production IL-6: a cytokine which functions alongside TNF-α and IL-1α/β in many aspects of innate immunity (FIG. 10D). These four anti-oxidants also abolished the small amount of IFN-γ induced by LPS stimulation (FIG. 10C).

Figure 8B:
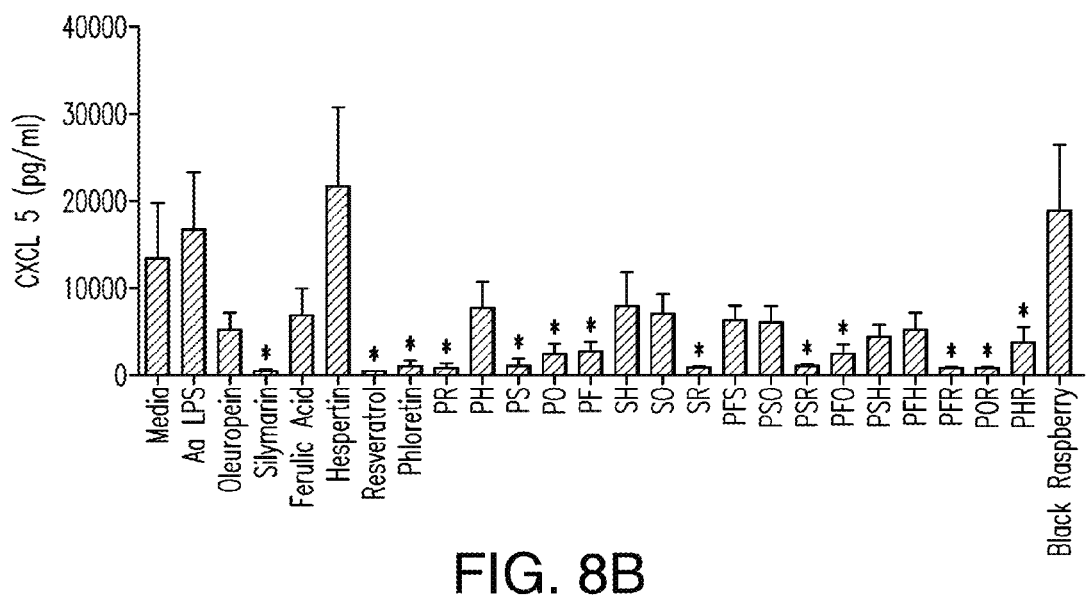
FIG. 8B shows the results of various antioxidants on CXCL 5.
Figure 8C:
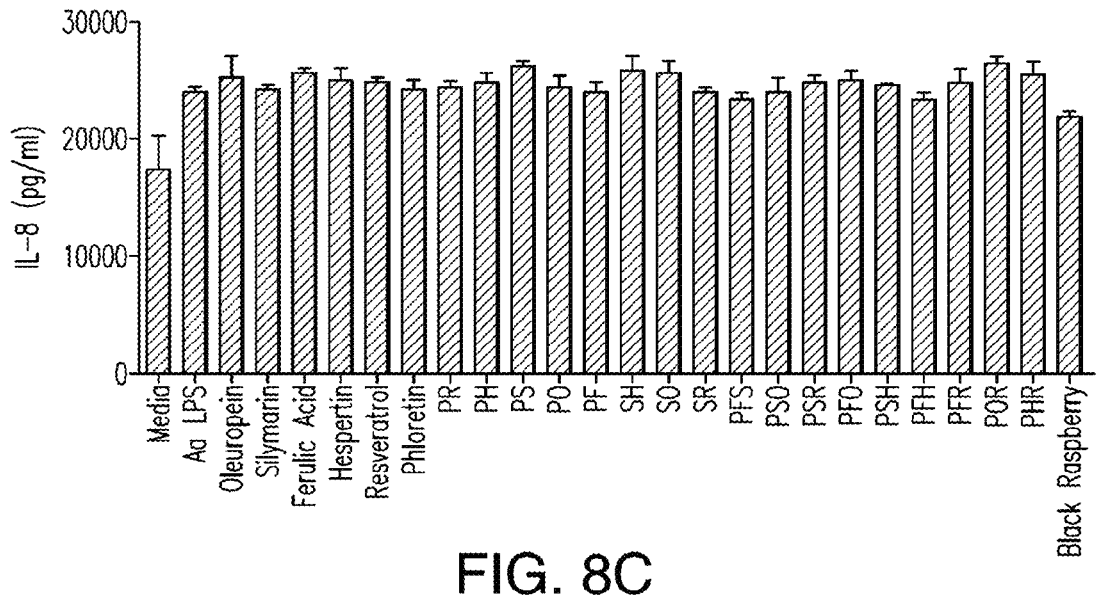
FIG. 8C shows the results of various antioxidants on IL-8.
Figure 8D:
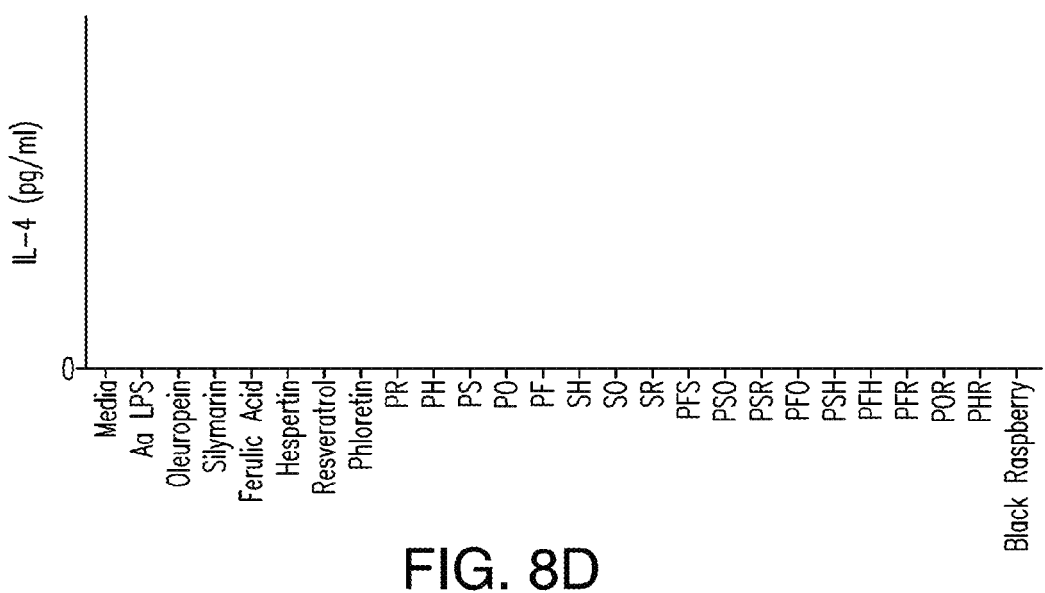
FIG. 8D shows the results of various antioxidants on IL-4.
Figure 12A:
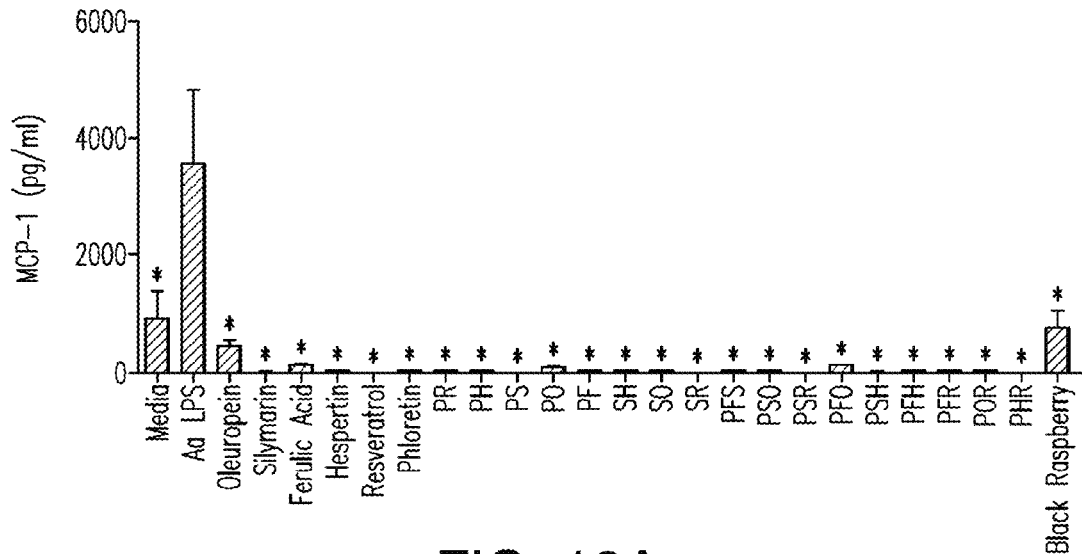
FIG. 12A shows the results of various antioxidants on MCP-1.
Figure 12B:
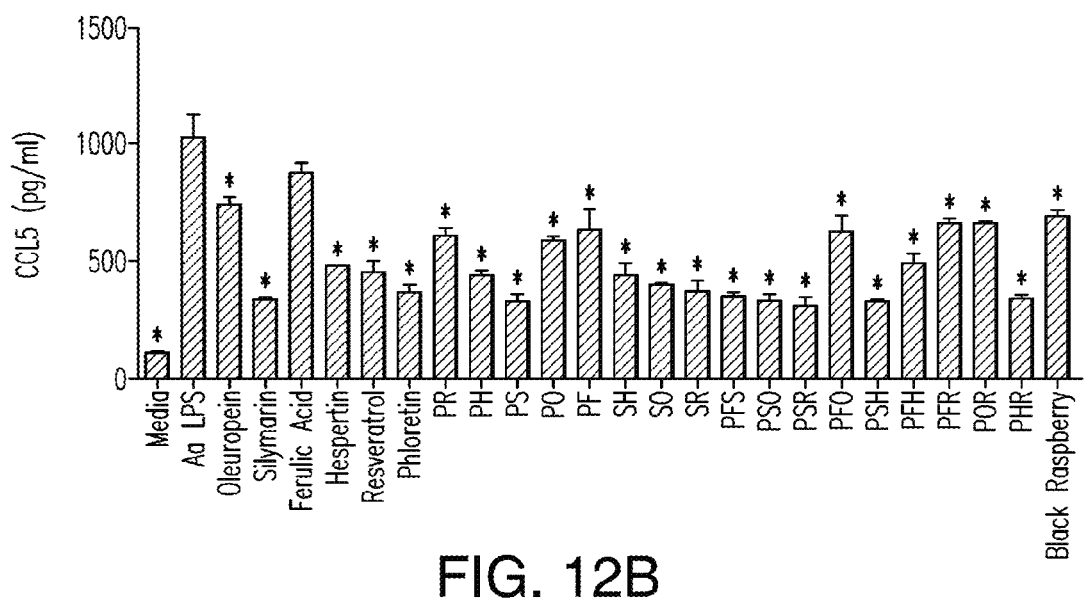
FIG. 12B shows the results of various antioxidants on CCL5.
Figure 12C:
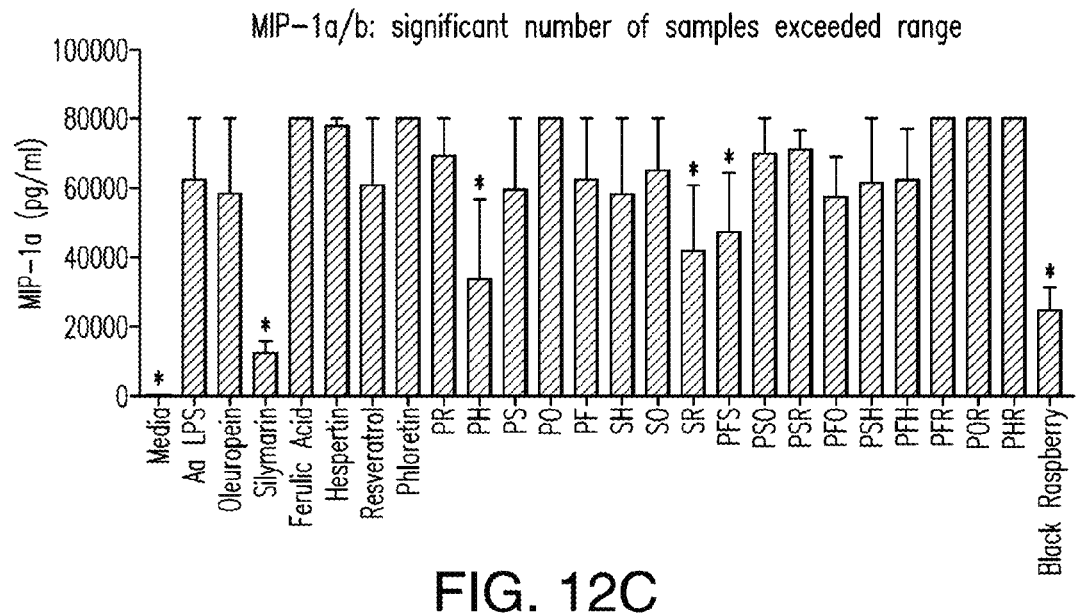
FIG. 12C shows the results of various antioxidants on MP-1α.
Figure 12D:
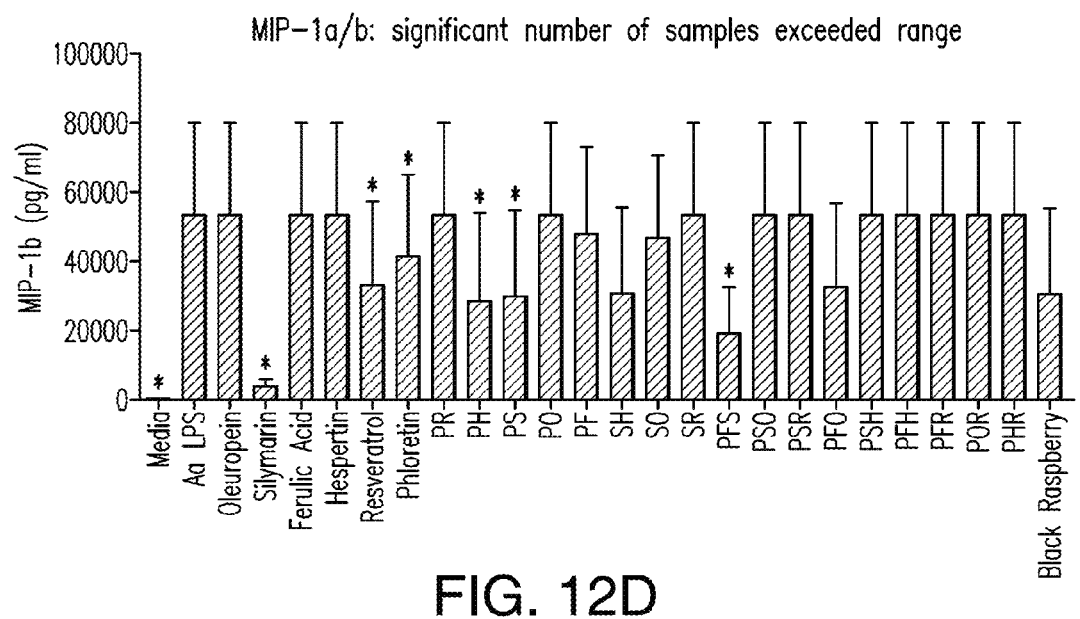
FIG. 12D shows the results of various antioxidants on MP-1β.

The release of several chemokines was inhibited by anti-oxidant treatment. CCL2 (aka MCP-1) is the principle chemokine for monocytes and its production was virtually abolished by the addition of any one of the six anti-oxidants tested (FIG. 12A). Apart from ferulic acid, the anti-oxidants tested also inhibited the production of another chemokine for monocytes, CCL5 (FIG. 12B). The structurally similar chemokines MIP-1α and MIP-1β were both inhibited by silymarin but not by any other anti-oxidants (FIGS. 12C and 12D). Silymarin, phloretin and resveratrol, had a similar effect on CXCL5—a chemokine which stimulates neutrophil chemotaxis (FIG. 8B). In addition to the suppression of inflammatory mediators and chemokines, a reduction in the differentiation factors G-CSF and GM-CSF was also observed (FIGS. 10A and 10B). Phloretin, hesperetin, silymarin and resveratrol inhibited G-CSF production, while only silymarin and resveratrol had a similar effect on GM-CSF.

Figure 11A:
FIG. 11A shows the results of various antioxidants on IL-10.
Figure 11B:
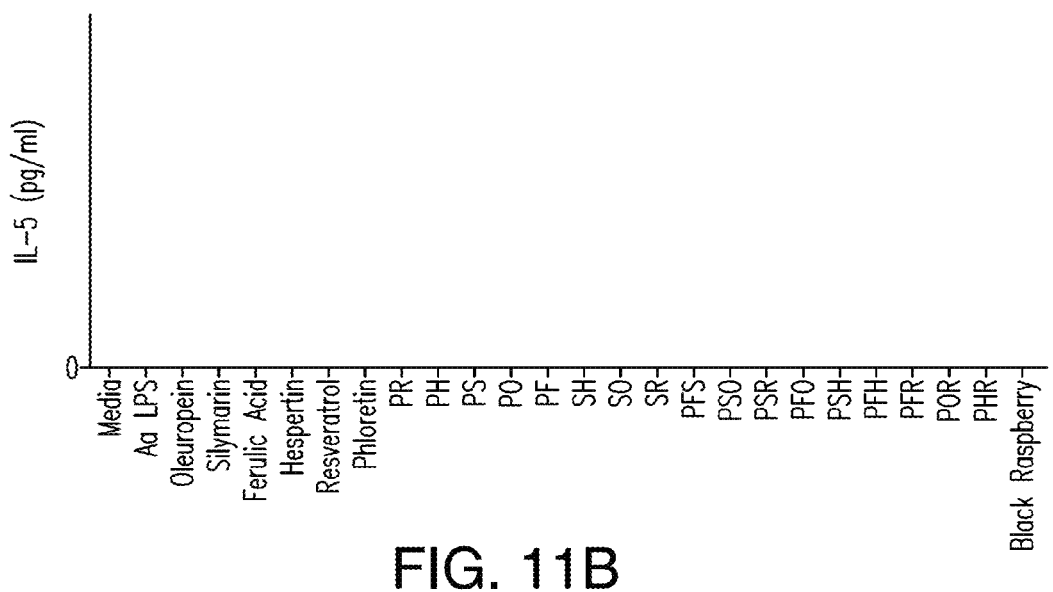
FIG. 11B shows the results of various antioxidants on IL-5.
Figure 11C:
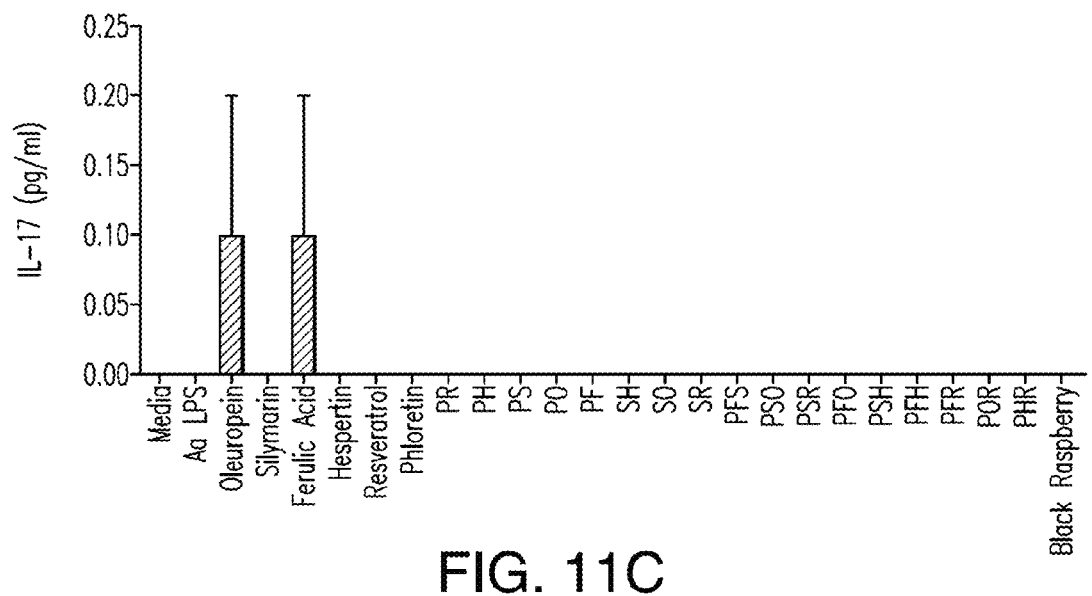
FIG. 11C shows the results of various antioxidants on IL-17.
Figure 11D:
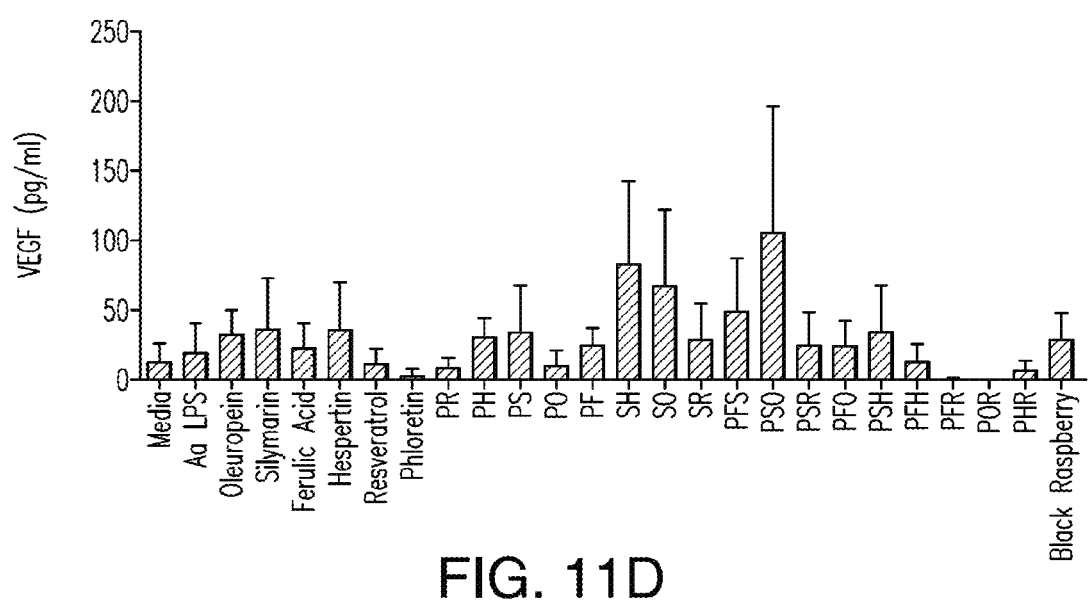
FIG. 11D shows the results of various antioxidants on VEGF.
Figure 13A:
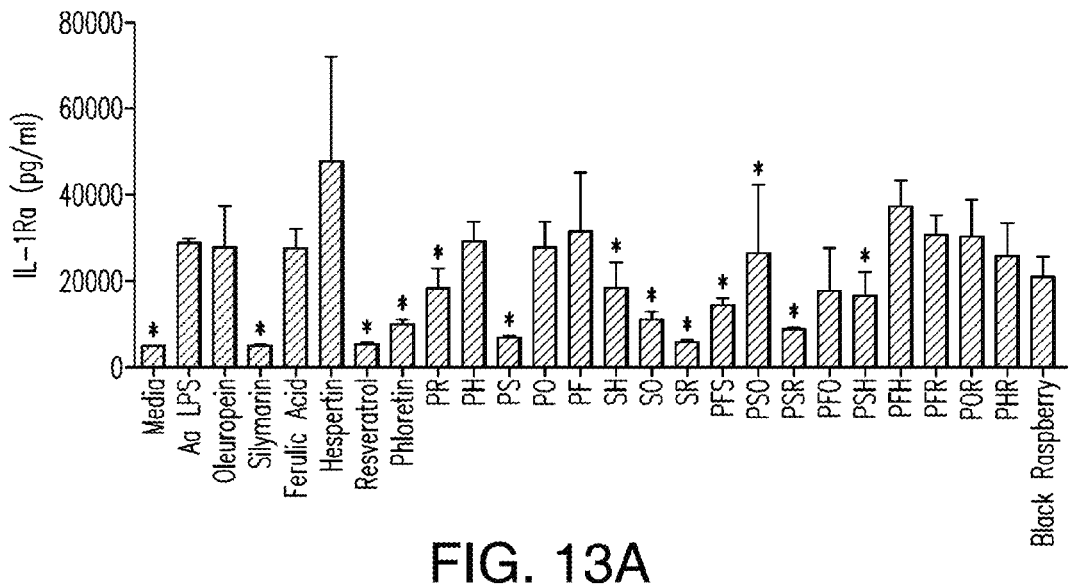
FIG. 13A shows the results of various antioxidants on IL-1Ra.
Figure 13B:
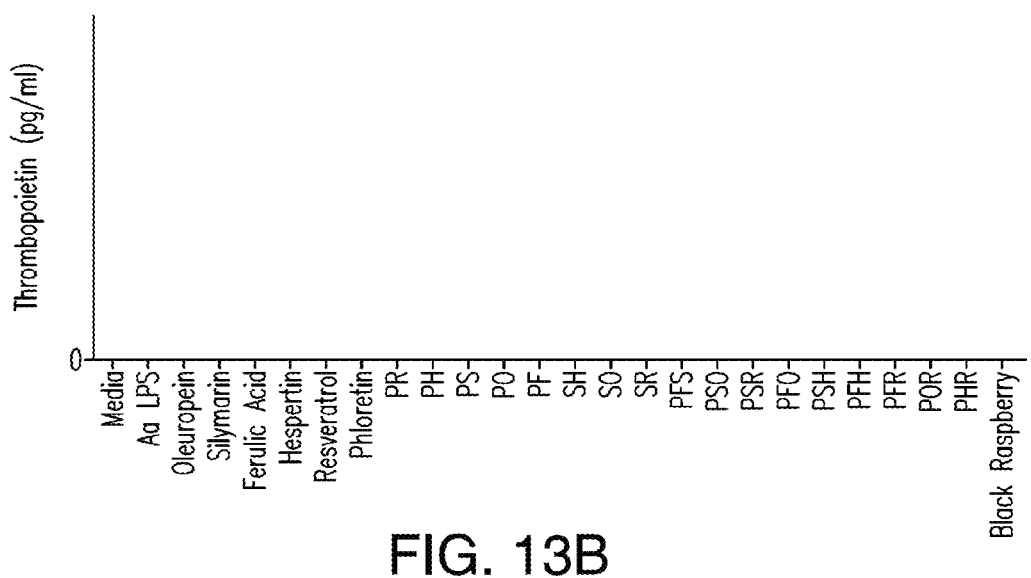
FIG. 13B shows the results of various antioxidants on Thrombopoietin.

Interestingly three of these anti-oxidants: phloretin, silymarin and resveratrol, also inhibited the production of the anti-inflammatory cytokine IL-1Ra, being a soluble decoy receptor for IL-1, and the anti-inflammatory and immunosuppressive cytokine IL-10 (FIGS. 13A and 11A).

Figure 14A:
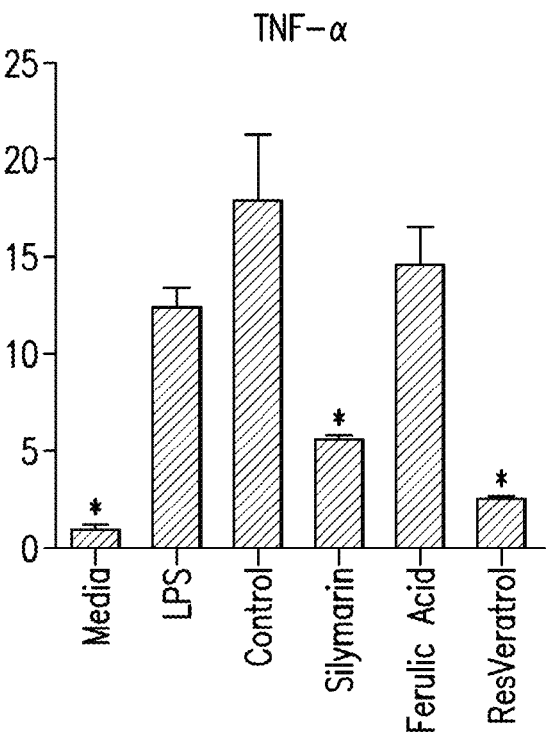
FIG. 14A shows the results of various antioxidants on TNF-α mRNA concentration.

Inhibition of TNF-α is present at the level of mRNA transcription—Whether the reduced production of inflammatory mediators was due to decreased mRNA transcription was investigated. PBMCs were cultured in media alone, stimulated with LPS, with LPS in the presence of 0.01% DMSO as the control, or treated with the highly inhibitory anti-oxidants silymarin or resveratrol or the largely inactive anti-oxidant ferulic acid. After 4 hrs the cells were harvested, total RNA isolated and RT-PCR performed to measure the levels of TNF-α mRNA present. TNF-α mRNA expression levels were reduced by greater than 2-fold upon treatment with silymarin or resveratrol but not ferulic acid (FIG. 14A).

Figure 14B:
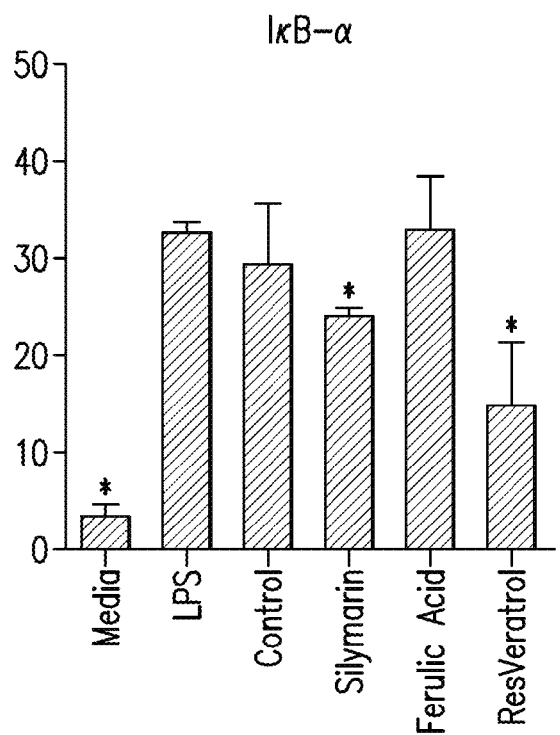
FIG. 14B shows the results of various antioxidants on IκB-α mRNA concentration.

NF-kB activation is reduced as indicated by reduced IκB-α mRNA expression—To further investigate the inhibitory mechanism present RT-PCR for IκB-α expression was performed, a factor immediately downstream of NF-κB signaling. LPS treatment of PBMCs resulted in a 30-fold increase in IκB-α mRNA expression compared to untreated PBMCs (FIG. 14B). Treatment with the anti-oxidants silymarin and resveratrol resulted in reduced IκB-α expression (approximately 25 and 50% reduction respectively).

Example 10

Other Case Studies Associated with Inflammation

A variety of other patients with various causes of inflammation were treated with anti-oxidants of the present disclosure as described below.

Nicotine Users

Figure 15B:
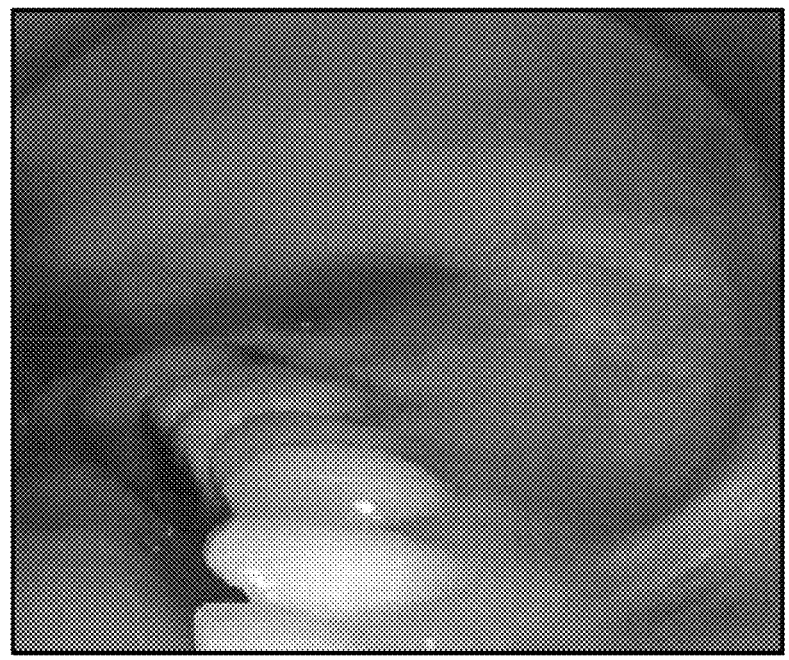
FIGS. 15A and 15B show the result of treatment with embodiments of the present disclosure.
Figure 15A:

A 36 year-old patient was a daily user of smokeless tobacco. He had developed a severe tissue reaction in the buccal vestibule. He was prescribed a regimen of three applications daily of a gel according to the present disclosure to be applied to the affected area. Over a six-week period, the patient complied with the regimen, although he continued to use the nicotine product. After six weeks, there was significant resolution of the lesion in spite of continued dipping. See FIGS. 15A (baseline) and 15B (after 6 weeks).

Figure 16B:
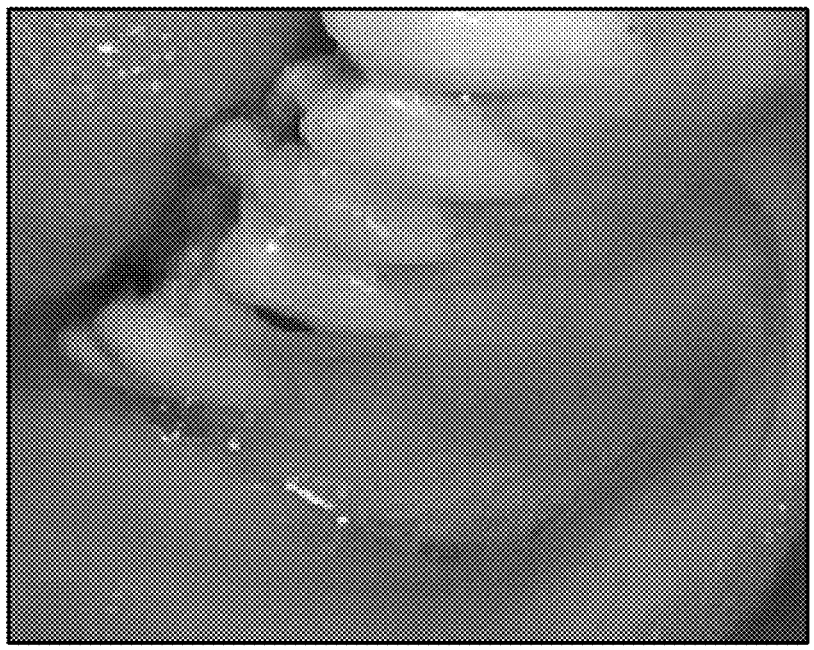
FIGS. 16A and 16B show the result of treatment with embodiments of the present disclosure.
Figure 16A:
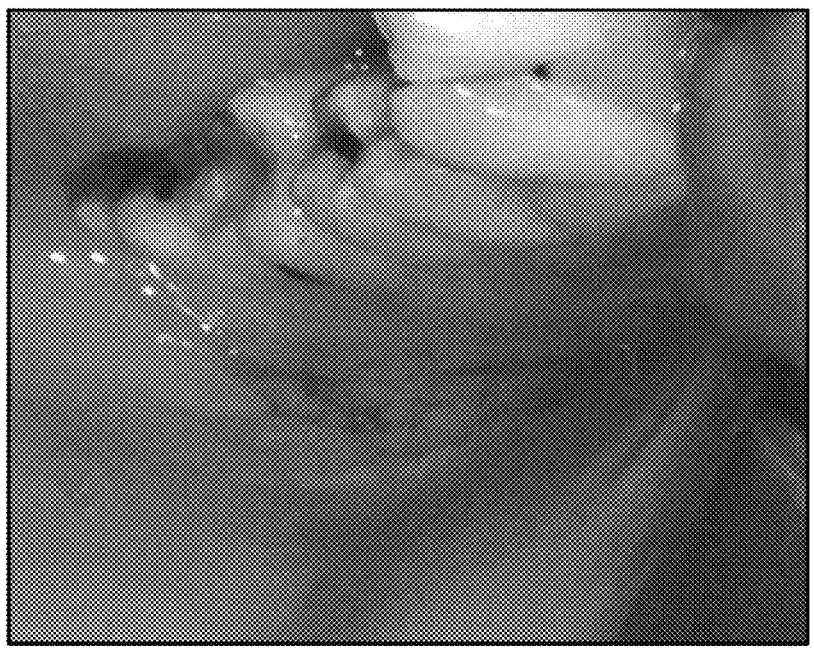

A second 43-year-old was a daily "dipper." His lesion has an irregular pattern of hyperkeratotic ridges. He used three applications daily of a gel according to the present disclosure applied to the affected area over a six-week period, while continuing to use the nicotine product. After six weeks, the lesion had significantly improved in the presence of his continued dipping habit. See FIGS. 16A (baseline) and 16B (after 6 weeks).

AlloDerm® Grafting

Figure 17A:
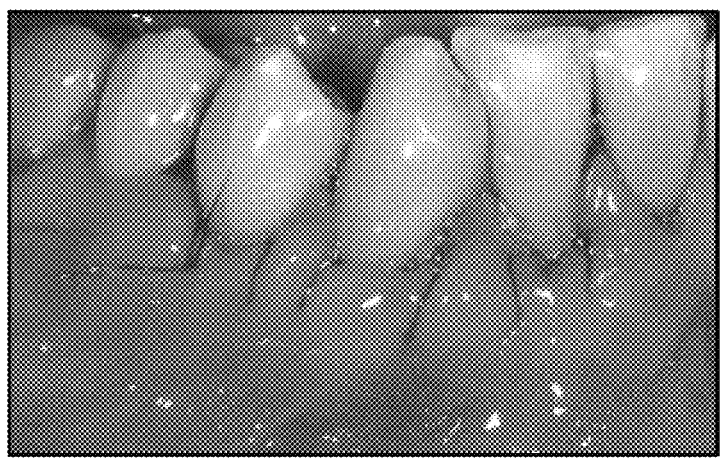
FIGS. 17A, 17B, and 17C show the result of treatment with embodiments of the present disclosure.
Figure 17B:
Figure 17C:
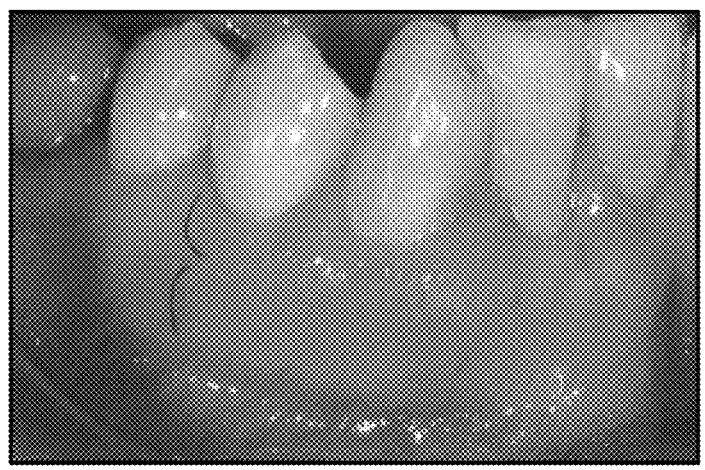

This 55 year-old patient had recession defects involving the mandibular right lateral incisor, canine, and first premolar. AlloDerm® (LifeCell Corp., Branchburg, N.J.) grafting was performed using the tunnel technique and platelet rich plasma. A gel according to the present disclosure was used 5× per day after surgery in lieu of chlorhexidine mouthrinse. The healing at 1 and 3 weeks appeared more advanced than typically seen in patients using chlorhexidine mouthrinses postsurgically. The patient strongly preferred the gel due to its soothing effect, pleasant taste, and lack of tooth staining experienced with a chlorhexidine mouthrinse in a previous surgery. See FIGS. 17A (baseline sutured), 17B (after 1 week), and 17C (after 3 weeks).

Post-Surgical Comparisons of Present Invention and Chlorhexidine

Figure 18A:
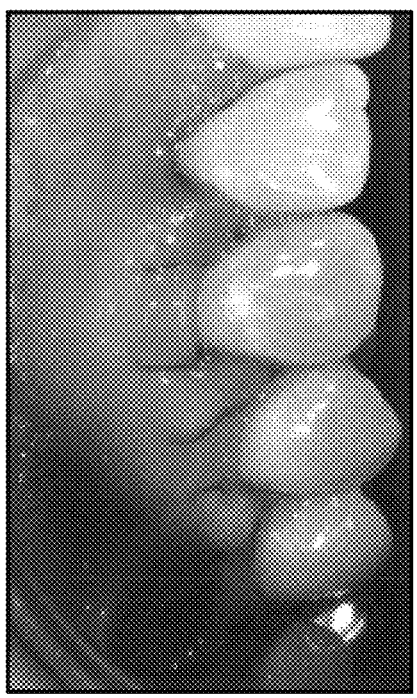
FIGS. 18A, 18B, 18C, and 18D show the result of treatment with embodiments of the present disclosure compared to traditional treatment.
Figure 18B:
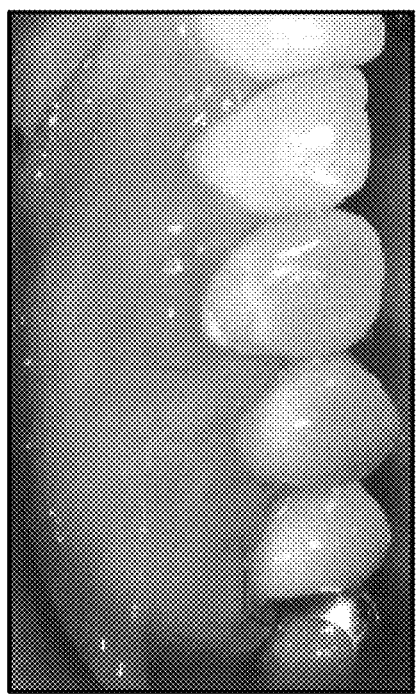
Figure 18C:
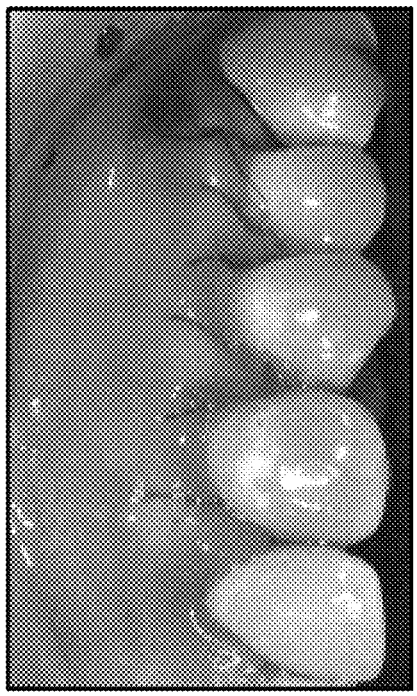
Figure 18D:
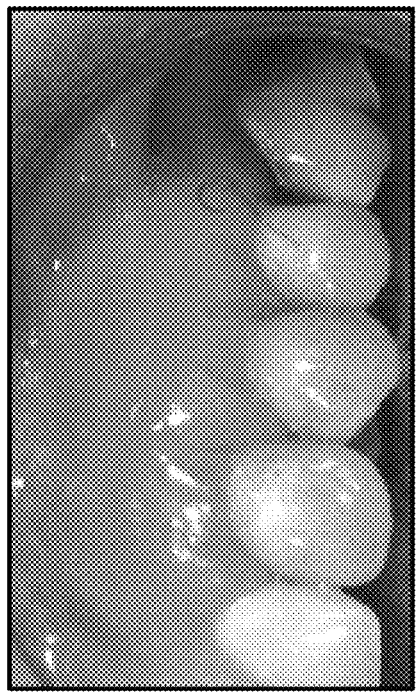

This 48 year-old patient had similar bilateral recession defects involving 3 teeth in the maxillary left and right posterior areas. AlloDerm® grafting was performed using the tunnel technique on 2 separate occasions. Platelet rich plasma was used at each surgery. A gel according to the present disclosure was used 5× per day after surgery on one side and chlorhexidine mouthrinse was used 2× per day after surgery on the other side. The result at 2 weeks appeared slightly better on gel side. The patient strongly preferred the gel due to its soothing effect, pleasant taste, and lack of tooth staining. See FIGS. 18A (gel, sutured baseline) and 18B (gel, after 2 weeks) vs. FIGS. 18C (chlorhexidine, sutured baseline) and 18D (chlorhexidine, after 2 weeks).

Figure 19A:
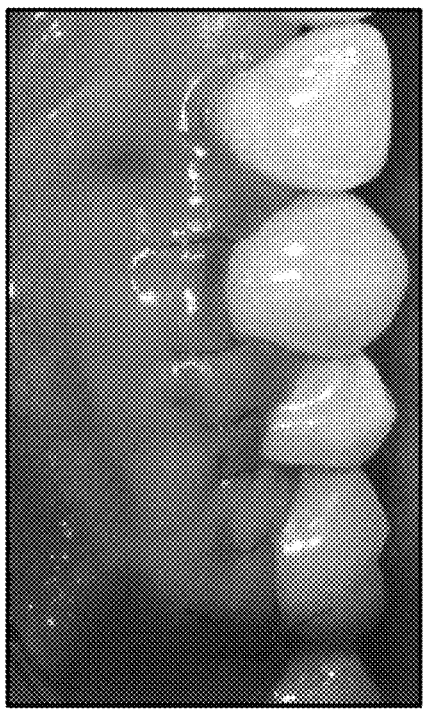
FIGS. 19A, 19B, 19C, and 19D show the result of treatment with embodiments of the present disclosure compared to traditional treatment.
Figure 19B:
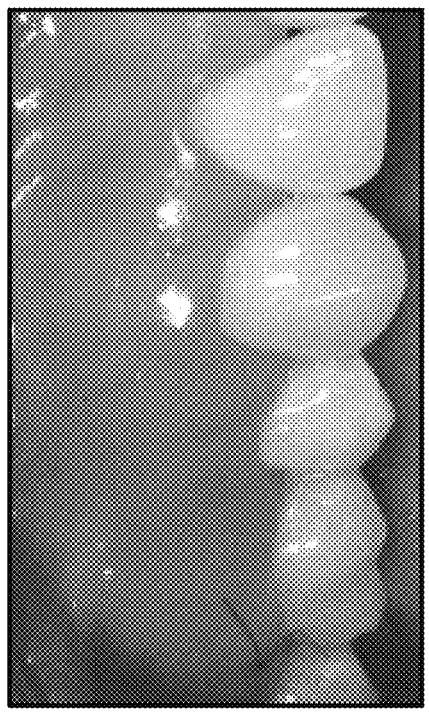
Figure 19C:
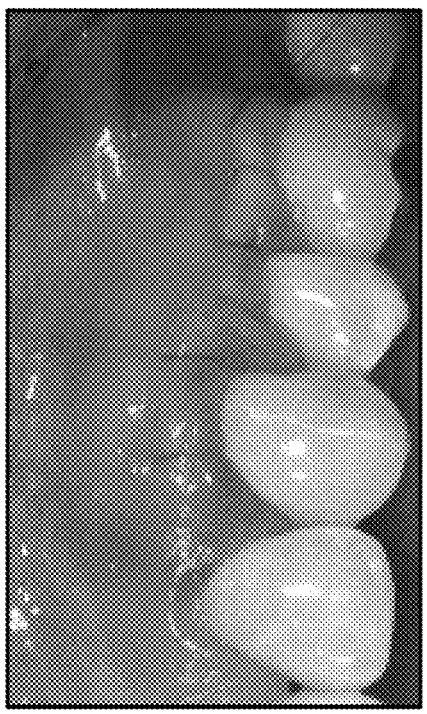
Figure 19D:
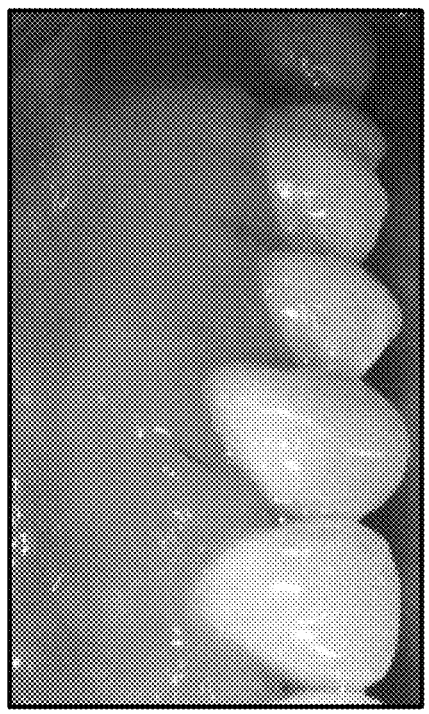

This 44 year-old male patient had similar bilateral recession defects involving 3 teeth in the maxillary left and right posterior areas. AlloDerm® grafting was performed using the tunnel technique on 2 separate occasions. Platelet rich plasma was not used for this patient. A gel according to the present disclosure was used 5× per day after surgery on one side and chlorhexidine mouthrinse was used 2× per day after surgery on the other side. The result at 2 weeks appeared similar for both sides. The patient preferred the gel due to its symptomatic relief, pleasing taste, and lack of tooth staining. See FIGS. 19A (gel, sutured baseline) and 19B (gel, after 3 weeks) vs. FIGS. 19C (chlorhexidine, sutured baseline) and 19D (chlorhexidine, after 3 weeks).

Although only exemplary embodiments of the invention are specifically described above, it will be appreciated that modifications and variations of these examples are possible without departing from the spirit and intended scope of the invention. For example, throughout the specification particular measurements are given. It would be understood by one of ordinary skill in the art that in many instances particularly outside of the examples other values similar to, but not exactly the same as the given measurements may be equivalent and may also be encompassed by the present invention.

The invention claimed is:

1. A method of increasing viability of gingival fibroblasts that have suffered oxidative damage by a metal released from a dental device in the mouth of a patient comprising applying topically to a soft oral tissue in the patient an oral antioxidant composition comprising:
   between 0.0001% and 5.0% total w/w of phloretin and ferulic acid and no additional antioxidants; and
   an orally pharmaceutically acceptable carrier,
   wherein the pH of the oral antioxidant composition is at least 5.0, and
   wherein the antioxidant composition increases viability of gingival fibroblasts that have suffered oxidative damage by a metal released from a dental device in the mouth of the patient by exhibiting a synergistic effect.

2. The method of claim 1, further comprising repeating the applying step after a selected time interval.

3. The method of claim 1, further comprising reducing the number of reactive oxygen species in the mouth of the patient.

4. The method of claim 1, further comprising repeating the applying step until the dental device is removed from the mouth of the patient.

5. The method of claim 1, wherein the orally pharmaceutically acceptable carrier is one of a spray, liquid, gel, or paste.

6. The method of claim 1, wherein the metal comprises at least one of zinc (Zn), copper (Cu), or nickel (Ni).

7. The method of claim 1, wherein the dental device comprises a permanent or semi-permanent dental device.

8. The method of claim 1, wherein the oral antioxidant composition remains in the mouth of the patient for at least five minutes.

9. The method of claim 1, wherein the oral antioxidant composition further comprises an antibacterial composition.

10. The method of claim 9, wherein the antibacterial composition comprises menthol.

11. The method of claim 9, wherein the antibacterial composition comprises xylitol.

12. The method of claim 9, wherein the antibacterial composition comprises thymol.

* * * * *